(12) United States Patent
Won

(10) Patent No.: US 12,076,336 B2
(45) Date of Patent: Sep. 3, 2024

(54) PHARMACEUTICAL COMPOSITION FOR PREVENTING OR TREATING LIVER CANCER

(71) Applicant: LEMONEX INC., Seoul (KR)

(72) Inventor: Cheolhee Won, Seoul (KR)

(73) Assignee: LEMONEX INC., Seoul (KR)

( * ) Notice: Subject to any disclaimer, the term of this patent is extended or adjusted under 35 U.S.C. 154(b) by 0 days.

(21) Appl. No.: 17/536,880

(22) Filed: Nov. 29, 2021

(65) Prior Publication Data

US 2022/0072027 A1    Mar. 10, 2022

Related U.S. Application Data

(62) Division of application No. 16/634,675, filed as application No. PCT/KR2018/008611 on Jul. 30, 2018, now abandoned.

(60) Provisional application No. 62/538,034, filed on Jul. 28, 2017.

(30) Foreign Application Priority Data

Jul. 30, 2018    (KR) ........................ 10-2018-0088375

(51) Int. Cl.
| | |
|---|---|
| *C07H 21/02* | (2006.01) |
| *A61K 31/713* | (2006.01) |
| *A61P 35/00* | (2006.01) |
| *C12N 15/113* | (2010.01) |

(52) U.S. Cl.
CPC ............ *A61K 31/713* (2013.01); *A61P 35/00* (2018.01); *C12N 15/113* (2013.01); *C12N 15/1135* (2013.01); *C12N 2310/14* (2013.01)

(58) Field of Classification Search
CPC .......................... C12N 15/113; C12N 2310/14
See application file for complete search history.

(56) References Cited

FOREIGN PATENT DOCUMENTS

| | | |
|---|---|---|
| CA | 2 852 064 A1 | 4/2013 |
| CN | 105722979 A | 6/2016 |
| CN | 105765069 A | 7/2016 |
| WO | WO 2019/146841 A1 | 8/2019 |

OTHER PUBLICATIONS

Office action issued on Jul. 28, 2021 from US Patent Office in a parent U.S. Appl. No. 16/634,675.
Qingyu Shen et al., "Barrier to autointegration factor 1, procollagen-lysine, 2-oxoglutarate 5-dioxygenase 3, and splicing factor 3b subunit 4 as early-stage cancer decision markers and drivers of hepatocellular carcinoma", Hepatology, vol. 67, No. 4, 2018, pp. 1360-1377, https://doi.org/10.1002/hep.29606.
Seongchan Kim et al., "In-depth study on the gene silencing capability of silica nanoparticles with different pore sizes: degree and duration of RNA interference", RSC Advances, Issue 32, 2016, pp. 27143-27150.

*Primary Examiner* — Amy Rose Hudson
(74) *Attorney, Agent, or Firm* — The PL Law Group, PLLC

(57) ABSTRACT

The present invention provides siRNA or dsRNA, which can effectively inhibit the expression of three highly expressed markers in liver cancer, and a pharmaceutical composition including the same can obtain excellent effects of preventing or treating liver cancer through RNAi. A pharmaceutical composition for preventing or treating liver cancer according to an embodiment of the present invention includes at least one of siRNA which includes a sense RNA having at least one sequence selected from the group consisting of sequences of SEQ ID NOs: 5 to 157, and an antisense RNA having a complementary sequence thereto and dsRNA having at least one sequence selected from the group consisting of sequences of SEQ ID NOs: 158 to 310.

9 Claims, 13 Drawing Sheets
Specification includes a Sequence Listing.

2 L scale    10 L scale 0 hr      120 hrs      360 hrs

| Samples | $t_{1/2}$ |
|---|---|
| MSN(200)$_2$ | 17.9 h |
| DDV(200)$_{10}$ | 57.4 h |
| DDV(200)$_{17}$ | 53.6 h |

DDV(300)₁₇

DDV(300)₁₇–NH₂

$t_{50\%}$ = about 2.5 days

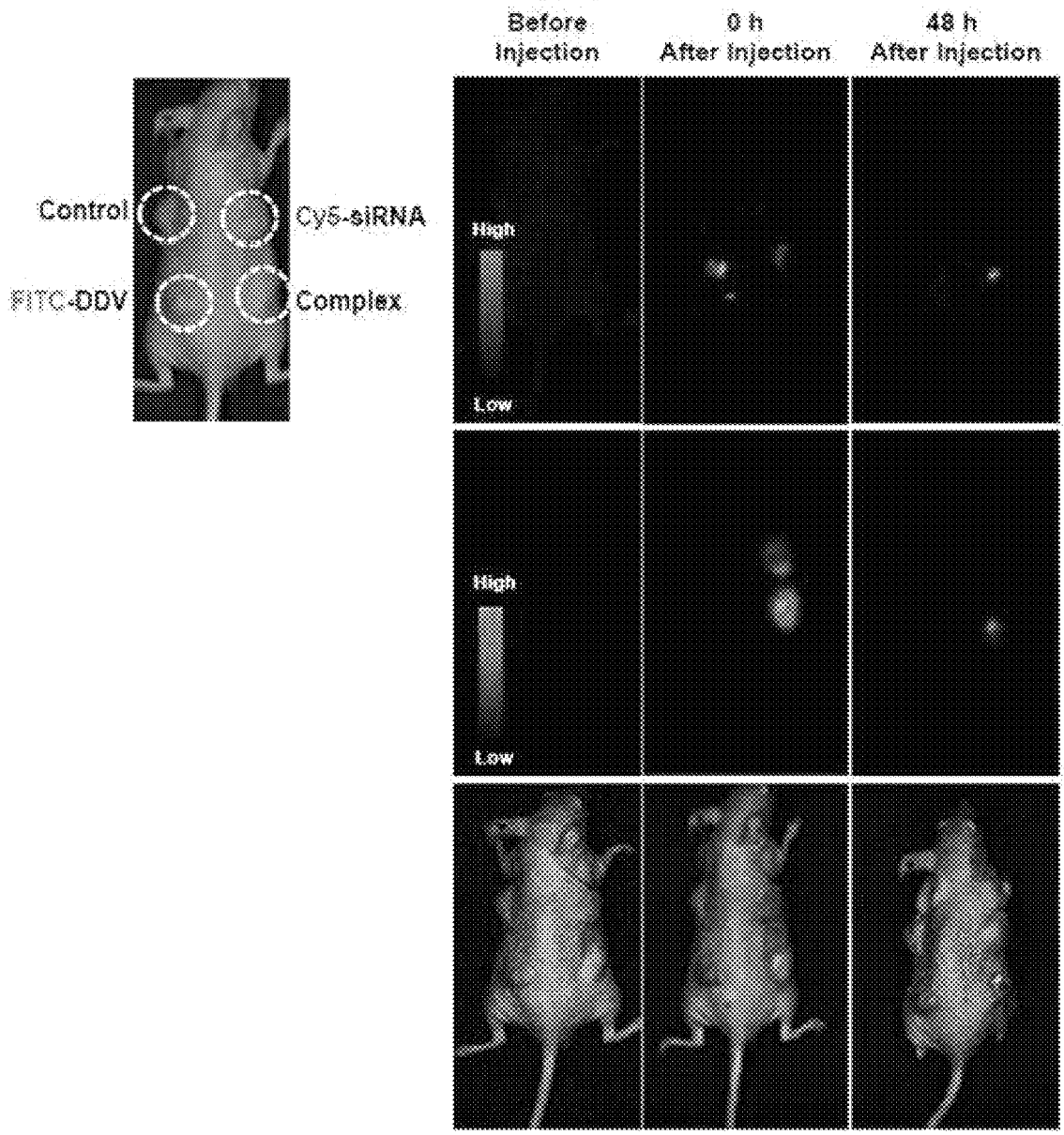

SEQUENCE LISTING

```
<160> NUMBER OF SEQ ID NOS: 640

<210> SEQ ID NO 1
<211> LENGTH: 270
<212> TYPE: DNA
<213> ORGANISM: Artificial Sequence
<220> FEATURE:
<223> OTHER INFORMATION: Human BANF1 gene variant1

<400> SEQUENCE: 1
atgacaacct cccaaaagca ccgagacttc gtggcagagc ccatggggga gaagccagtg      60
gggagcctgg ctgggattgg tgaagtcctg ggcaagaagc tggaggaaag gggtttttgac    120 aaggcctatg ttgtccttgg ccagtttctg gtgctaaaga aagatgaaga cctcttccgg     180
gaatggctga aagacacttg tggcgccaac gccaagcagt cccgggactg cttcggatgc     240
cttcgagagt ggtgcgacgc cttcttgtga                                      270
```

<210> SEQ ID NO 2
<211> LENGTH: 270
<212> TYPE: DNA
<213> ORGANISM: Artificial Sequence
<220> FEATURE:
<223> OTHER INFORMATION: Human BANF1 gene variant2

<400> SEQUENCE: 2

```
atgacaacct cccaaaagca ccgagacttc gtggcagagc ccatgggggga gaagccagtg      60 gggagcctgg ctgggattgg tgaagtcctg ggcaagaagc tggaggaaag gggttttgac     120
aaggcctatg ttgtccttgg ccagtttctg gtgctaaaga agatgaaga cctcttccgg      180 gaatggctga agacacttg tggcgccaac gccaagcagt cccgggactg cttcggatgc     240
cttcgagagt ggtgcgacgc cttcttgtga                                      270
```

<210> SEQ ID NO 3
<211> LENGTH: 2217
<212> TYPE: DNA
<213> ORGANISM: Artificial Sequence
<220> FEATURE:
<223> OTHER INFORMATION: Human PLOD3 gene

<400> SEQUENCE: 3

```
atgacctcct cggggcctgg accccggttc ctgctgctgc tgccgctgct gctgcccct      60 gcggcctcag cctccgaccg gccccggggc cgagacccgg tcaacccaga gaagctgctg    120
gtgatcactg tggccacagc tgaaaccgag gggtacctgc gtttcctgcg ctctgcggag    180
ttcttcaact acactgtgcg gaccctgggc ctgggagagg agtggcgagg gggtgatgtg    240
gctcgaacag ttggtggagg acagaaggtc cggtggttaa agaaggaaat ggagaaatac    300
gctgaccggg aggatatgat catcatgttt gtggatagct acgacgtgat tctggccggc    360
agccccacag agctgctgaa gaagttcgtc cagagtggca gccgcctgct cttctctgca    420
gagagcttct gctggcccga gtggggggctg gcggagcagt accctgaggt gggcacgggg    480
aagcgcttcc tcaattctgg tggattcatc ggttttgcca ccaccatcca ccaaatcgtg    540
cgccagtgga agtacaagga tgatgacgac gaccagctgt tctacacacg gctctacctg    600
gacccaggac tgagggagaa actcagcctt aatctggatc ataagtctcg gatctttcag    660
aacctcaacg gggctttaga tgaagtggtt ttaaagtttg atcggaaccg tgtgcgtatc    720
cggaacgtgg cctacgacac gctcccccatt gtggtccatg gaaacggtcc cactaagctg    780
cagctcaact acctgggaaa ctacgtcccc aatggctgga ctcctgaggg aggctgtggc    840
ttctgcaacc aggaccggag gacactcccg ggggggcagc ctcccccccg ggtgtttctg    900
gccgtgtttg tggaacagcc tactccgttt ctgccccgct tcctgcagcg gctgctactc    960
ctggactatc ccccgacag ggtcacccctt ttcctgcaca caacgaggt cttccatgaa    1020 ccccacatcg ctgactcctg gccgcagctc caggaccact tctcagctgt gaagctcgtg   1080
gggccggagg aggctctgag cccaggcgag gccagggaca tggccatgga cctgtgtcgg   1140
caggaccccg agtgtgagtt ctacttcagc ctggacgccg acgctgtcct caccaacctg   1200
cagaccctgc gtatcctcat tgaggagaac aggaaggtga tcgcccccat gctgtccccgc   1260 cacggcaagc tgtggtccaa cttctgggcc gccctgagcc ccgatgagta ctacgcccgc   1320
tccgaggact acgtggagct ggtgcagcgg aagcgagtgg tgtgtgggaa tgtaccatac   1380
atctcccagg cctatgtgat ccggggtgat acctgcgga tggagctgcc ccagagggat   1440
```

| | |
|---|---|
| gtgttctcgg gcagtgacac agacccggac atggccttct gtaagagctt cgagacaag | 1500 |
| ggcatcttcc tccatctgag caatcagcat gaatttggcc ggctcctggc cacttccaga | 1560 |
| tacgacacgg agcacctgca ccccgacctc tggcagatct tcgacaaccc cgtcgactgg | 1620 |
| aaggagcagt acatccacga gaactacagc cgggccctgg aaggggaagg aatcgtggag | 1680 |
| cagccatgcc cggacgtgta ctggttccca ctgctgtcag aacaaatgtg tgatgagctg | 1740 |
| gtggcagaga tggagcacta cggccagtgg tcaggcggcc ggcatgagga ttcaaggctg | 1800 |
| gctggaggct acgagaatgt gcccaccgtg gacatccaca tgaagcaggt ggggtacgag | 1860 |
| gaccagtggc tgcagctgct gcggacgtat gtgggcccca tgaccgagag cctgtttccc | 1920 |
| ggttaccaca ccaaggcgcg ggcggtgatg aactttgtgg ttcgctaccg gccagacgag | 1980 |
| cagccgtctc tgcggccaca ccacgactca tccaccttca ccctcaacgt tgccctcaac | 2040 |
| cacaagggcc tggactatga gggaggtggc tgccgcttcc tgcgctacga ctgtgtgatc | 2100 |
| tcctccccga ggaagggctg ggcactcctg caccccggcc gcctcaccca ctaccacgag | 2160 |
| gggctgccaa cgacctgggg cacacgctac atcatggtgt cctttgtcga cccctga | 2217 |

<210> SEQ ID NO 4
<211> LENGTH: 1275
<212> TYPE: DNA
<213> ORGANISM: Artificial Sequence
<220> FEATURE:
<223> OTHER INFORMATION: Human SF3B4 gene

<400> SEQUENCE: 4

| | |
|---|---|
| atggctgccg ggccgatctc cgagcggaat caggatgcca ctgtgtacgt gggggggcctg | 60 |
| gatgagaagg ttagtgaacc gctgctgtgg gaactgtttc tccaggctgg accagtagtc | 120 |
| aacacccaca tgccaaagga tagagtcact ggccagcacc aaggctatgg ctttgtggaa | 180 |
| ttcttgagtg aggaagatgc tgactatgcc attaagatca tgaacatgat caaactctat | 240 |
| gggaagccaa tacgggtgaa caaagcatca gctcacaaca aaaacctgga tgtaggggcc | 300 |
| aacattttca ttgggaacct ggaccctgag attgatgaga agttgctttta tgatactttc | 360 |
| agcgcctttg gggtcatctt acaaacccc aaaattatgc gggaccctga cacaggcaac | 420 |
| tccaaaggtt atgcctttat taattttgct tcatttgatg cttcggatgc agcaattgaa | 480 |
| gccatgaatg ggcagtacct ctgtaaccgt cctatcaccg tatcttatgc cttcaagaag | 540 |
| gactccaagg gtgagcgcca tggctcagca gccgaacgac ttctggcagc tcagaacccg | 600 |
| ctctcccagg ctgatcgccc tcatcagctg tttgcagatg cacctcctcc accctctgct | 660 |
| cccaatcctg tggtatcatc attggggtct gggcttcctc caccaggcat gcctcctcct | 720 |
| ggctccttcc caccccagt gccacctcct ggagccctcc cacctgggat ccccccagcc | 780 |
| atgccccac cacctatgcc tcctggggct gcaggacatg gcccccatc ggcaggaacc | 840 |
| ccaggggcag gacatcctgg tcatggacac tcacatcctc acccattccc accgggtggg | 900 |
| atgccccatc cagggatgtc tcagatgcag cttgcacacc atggccctca tggcttagga | 960 |
| catccccacg ctggaccccc aggctctggg ggccagccac cgcccgacc accacctgga | 1020 |
| atgcctcatc ctggacctcc tccaatgggc atgccccccc gagggcctcc attcggatct | 1080 |
| cccatgggtc acccaggtcc tatgcctccg catggtatgc gtggacctcc tccactgatg | 1140 |
| ccccccatg gatacactgg ccctccacga ccccaccct atggctacca gcgggggcct | 1200 |
| ctccctccac ccagacccac tccccggcca ccagttcccc ctcgaggccc acttcgaggc | 1260 |
| cctctcccctc agtaa | 1275 |

```
<210> SEQ ID NO 5
<211> LENGTH: 20
<212> TYPE: RNA
<213> ORGANISM: Artificial Sequence
<220> FEATURE:
<223> OTHER INFORMATION: siRNA sense strand

<400> SEQUENCE: 5
caagaagcug gaggaaaguu                                                     20

<210> SEQ ID NO 6
<211> LENGTH: 22
<212> TYPE: RNA
<213> ORGANISM: Artificial Sequence
<220> FEATURE:
<223> OTHER INFORMATION: siRNA sense strand

<400> SEQUENCE: 6
gaaagaugaa gaccucuucc uu                                                  22

<210> SEQ ID NO 7
<211> LENGTH: 22
<212> TYPE: RNA
<213> ORGANISM: Artificial Sequence
<220> FEATURE:
<223> OTHER INFORMATION: siRNA sense strand

<400> SEQUENCE: 7
ggaauggcug aaagacacuu uu                                                  22

<210> SEQ ID NO 8
<211> LENGTH: 20
<212> TYPE: RNA
<213> ORGANISM: Artificial Sequence
<220> FEATURE:
<223> OTHER INFORMATION: siRNA sense strand

<400> SEQUENCE: 8
ccaguguucc caguucccuu                                                     20

<210> SEQ ID NO 9
<211> LENGTH: 20
<212> TYPE: RNA
<213> ORGANISM: Artificial Sequence
<220> FEATURE:
<223> OTHER INFORMATION: siRNA sense strand

<400> SEQUENCE: 9
ccaguccaac ugcgaggauu                                                     20

<210> SEQ ID NO 10
<211> LENGTH: 20
<212> TYPE: RNA
<213> ORGANISM: Artificial Sequence
<220> FEATURE:
<223> OTHER INFORMATION: siRNA sense strand

<400> SEQUENCE: 10
cgacgugagu cugagucuuu                                                     20

<210> SEQ ID NO 11
<211> LENGTH: 20
<212> TYPE: RNA
<213> ORGANISM: Artificial Sequence
<220> FEATURE:
```

<223> OTHER INFORMATION: siRNA sense strand

<400> SEQUENCE: 11
guccgucuuc uaacucuuuu                                              20

<210> SEQ ID NO 12
<211> LENGTH: 20
<212> TYPE: RNA
<213> ORGANISM: Artificial Sequence
<220> FEATURE:
<223> OTHER INFORMATION: siRNA sense strand

<400> SEQUENCE: 12
cgucaagccu aaguccuuuu                                              20

<210> SEQ ID NO 13
<211> LENGTH: 20
<212> TYPE: RNA
<213> ORGANISM: Artificial Sequence
<220> FEATURE:
<223> OTHER INFORMATION: siRNA sense strand

<400> SEQUENCE: 13
gcagagaaag gaaguccuuu                                              20

<210> SEQ ID NO 14
<211> LENGTH: 20
<212> TYPE: RNA
<213> ORGANISM: Artificial Sequence
<220> FEATURE:
<223> OTHER INFORMATION: siRNA sense strand

<400> SEQUENCE: 14
cgagaagcga gaccuuaguu                                              20

<210> SEQ ID NO 15
<211> LENGTH: 20
<212> TYPE: RNA
<213> ORGANISM: Artificial Sequence
<220> FEATURE:
<223> OTHER INFORMATION: siRNA sense strand

<400> SEQUENCE: 15
ccucaacucu auagcucuuu                                              20

<210> SEQ ID NO 16
<211> LENGTH: 20
<212> TYPE: RNA
<213> ORGANISM: Artificial Sequence
<220> FEATURE:
<223> OTHER INFORMATION: siRNA sense strand

<400> SEQUENCE: 16
cuaguggcuu gagguaucuu                                              20

<210> SEQ ID NO 17
<211> LENGTH: 20
<212> TYPE: RNA
<213> ORGANISM: Artificial Sequence
<220> FEATURE:
<223> OTHER INFORMATION: siRNA sense strand

<400> SEQUENCE: 17
ggauuaagcc ugaucaaguu                                              20

```
<210> SEQ ID NO 18
<211> LENGTH: 20
<212> TYPE: RNA
<213> ORGANISM: Artificial Sequence
<220> FEATURE:
<223> OTHER INFORMATION: siRNA sense strand

<400> SEQUENCE: 18
gacugcuucg gaugccuuuu                                               20

<210> SEQ ID NO 19
<211> LENGTH: 20
<212> TYPE: RNA
<213> ORGANISM: Artificial Sequence
<220> FEATURE:
<223> OTHER INFORMATION: siRNA sense strand

<400> SEQUENCE: 19
ccuucuugug augcucucuu                                               20

<210> SEQ ID NO 20
<211> LENGTH: 20
<212> TYPE: RNA
<213> ORGANISM: Artificial Sequence
<220> FEATURE:
<223> OTHER INFORMATION: siRNA sense strand

<400> SEQUENCE: 20
ccucauccag aguuugcauu                                               20

<210> SEQ ID NO 21
<211> LENGTH: 20
<212> TYPE: RNA
<213> ORGANISM: Artificial Sequence
<220> FEATURE:
<223> OTHER INFORMATION: siRNA sense strand

<400> SEQUENCE: 21
ccuguccucu acgaaggauu                                               20

<210> SEQ ID NO 22
<211> LENGTH: 22
<212> TYPE: RNA
<213> ORGANISM: Artificial Sequence
<220> FEATURE:
<223> OTHER INFORMATION: siRNA sense strand

<400> SEQUENCE: 22
gauugcuauu gucguacuca uu                                            22

<210> SEQ ID NO 23
<211> LENGTH: 20
<212> TYPE: RNA
<213> ORGANISM: Artificial Sequence
<220> FEATURE:
<223> OTHER INFORMATION: siRNA sense strand

<400> SEQUENCE: 23
ggauucucgc ucuugcauuu                                               20

<210> SEQ ID NO 24
<211> LENGTH: 20
<212> TYPE: RNA
<213> ORGANISM: Artificial Sequence
<220> FEATURE:
<223> OTHER INFORMATION: siRNA sense strand
```

```
<400> SEQUENCE: 24
ggugacaguu accagcuuuu                                              20

<210> SEQ ID NO 25
<211> LENGTH: 20
<212> TYPE: RNA
<213> ORGANISM: Artificial Sequence
<220> FEATURE:
<223> OTHER INFORMATION: siRNA sense strand

<400> SEQUENCE: 25
ccucacuuuc aauccguuuu                                              20

<210> SEQ ID NO 26
<211> LENGTH: 20
<212> TYPE: RNA
<213> ORGANISM: Artificial Sequence
<220> FEATURE:
<223> OTHER INFORMATION: siRNA sense strand

<400> SEQUENCE: 26
gcagaacagu cacuguccuu                                              20

<210> SEQ ID NO 27
<211> LENGTH: 22
<212> TYPE: RNA
<213> ORGANISM: Artificial Sequence
<220> FEATURE:
<223> OTHER INFORMATION: siRNA sense strand

<400> SEQUENCE: 27
gaucaauaaa gucaguggcu uu                                           22

<210> SEQ ID NO 28
<211> LENGTH: 23
<212> TYPE: RNA
<213> ORGANISM: Artificial Sequence
<220> FEATURE:
<223> OTHER INFORMATION: siRNA sense strand

<400> SEQUENCE: 28
aagaagcugg aggaaagggg uuu                                          23

<210> SEQ ID NO 29
<211> LENGTH: 22
<212> TYPE: RNA
<213> ORGANISM: Artificial Sequence
<220> FEATURE:
<223> OTHER INFORMATION: siRNA sense strand

<400> SEQUENCE: 29
augacaaccu cccaaaagca uu                                           22

<210> SEQ ID NO 30
<211> LENGTH: 20
<212> TYPE: RNA
<213> ORGANISM: Artificial Sequence
<220> FEATURE:
<223> OTHER INFORMATION: siRNA sense strand

<400> SEQUENCE: 30
ccgagacuuc guggcagauu                                              20

<210> SEQ ID NO 31
<211> LENGTH: 17
```

```
<212> TYPE: RNA
<213> ORGANISM: Artificial Sequence
<220> FEATURE:
<223> OTHER INFORMATION: siRNA sense strand

<400> SEQUENCE: 31
agccuggcug ggauuuu                                                  17

<210> SEQ ID NO 32
<211> LENGTH: 19
<212> TYPE: RNA
<213> ORGANISM: Artificial Sequence
<220> FEATURE:
<223> OTHER INFORMATION: siRNA sense strand

<400> SEQUENCE: 32
caagaagcug gaggaaauu                                                19

<210> SEQ ID NO 33
<211> LENGTH: 22
<212> TYPE: RNA
<213> ORGANISM: Artificial Sequence
<220> FEATURE:
<223> OTHER INFORMATION: siRNA sense strand

<400> SEQUENCE: 33
ccaguuucug gugcuaaaga uu                                            22

<210> SEQ ID NO 34
<211> LENGTH: 20
<212> TYPE: RNA
<213> ORGANISM: Artificial Sequence
<220> FEATURE:
<223> OTHER INFORMATION: siRNA sense strand

<400> SEQUENCE: 34
aagaugaaga ccucuuccuu                                               20

<210> SEQ ID NO 35
<211> LENGTH: 21
<212> TYPE: RNA
<213> ORGANISM: Artificial Sequence
<220> FEATURE:
<223> OTHER INFORMATION: siRNA sense strand

<400> SEQUENCE: 35
ggacugcuuc ggaugccuuu u                                             21

<210> SEQ ID NO 36
<211> LENGTH: 21
<212> TYPE: RNA
<213> ORGANISM: Artificial Sequence
<220> FEATURE:
<223> OTHER INFORMATION: siRNA sense strand

<400> SEQUENCE: 36
aguggugcga cgccuucuuu u                                             21

<210> SEQ ID NO 37
<211> LENGTH: 21
<212> TYPE: RNA
<213> ORGANISM: Artificial Sequence
<220> FEATURE:
<223> OTHER INFORMATION: siRNA sense strand

<400> SEQUENCE: 37
```
aguggugcga cgccuucuuu u                                          21

<210> SEQ ID NO 38
<211> LENGTH: 22
<212> TYPE: RNA
<213> ORGANISM: Artificial Sequence
<220> FEATURE:
<223> OTHER INFORMATION: siRNA sense strand

<400> SEQUENCE: 38
uugcuauugu cguacucacc uu                                         22

<210> SEQ ID NO 39
<211> LENGTH: 20
<212> TYPE: RNA
<213> ORGANISM: Artificial Sequence
<220> FEATURE:
<223> OTHER INFORMATION: siRNA sense strand

<400> SEQUENCE: 39
gauucucgcu cuugcauguu                                            20

<210> SEQ ID NO 40
<211> LENGTH: 22
<212> TYPE: RNA
<213> ORGANISM: Artificial Sequence
<220> FEATURE:
<223> OTHER INFORMATION: siRNA sense strand

<400> SEQUENCE: 40
caguucccug gugacaguua uu                                         22

<210> SEQ ID NO 41
<211> LENGTH: 20
<212> TYPE: RNA
<213> ORGANISM: Artificial Sequence
<220> FEATURE:
<223> OTHER INFORMATION: siRNA sense strand

<400> SEQUENCE: 41
ccagcuuucc ugaauggauu                                            20

<210> SEQ ID NO 42
<211> LENGTH: 22
<212> TYPE: RNA
<213> ORGANISM: Artificial Sequence
<220> FEATURE:
<223> OTHER INFORMATION: siRNA sense strand

<400> SEQUENCE: 42
cucacuuuca auccguuuga uu                                         22

<210> SEQ ID NO 43
<211> LENGTH: 22
<212> TYPE: RNA
<213> ORGANISM: Artificial Sequence
<220> FEATURE:
<223> OTHER INFORMATION: siRNA sense strand

<400> SEQUENCE: 43
cagaacaguc acugccuug uu                                          22

<210> SEQ ID NO 44
<211> LENGTH: 20
<212> TYPE: RNA
<213> ORGANISM: Artificial Sequence

```
<220> FEATURE:
<223> OTHER INFORMATION: siRNA sense strand

<400> SEQUENCE: 44 caccaguccaa acugcgaguu                                                    20

<210> SEQ ID NO 45
<211> LENGTH: 22
<212> TYPE: RNA
<213> ORGANISM: Artificial Sequence
<220> FEATURE:
<223> OTHER INFORMATION: siRNA sense strand

<400> SEQUENCE: 45
ugcgacguga gucugagucu uu                                                  22

<210> SEQ ID NO 46
<211> LENGTH: 20
<212> TYPE: RNA
<213> ORGANISM: Artificial Sequence
<220> FEATURE:
<223> OTHER INFORMATION: siRNA sense strand

<400> SEQUENCE: 46
ccuccgaaaa ccguacuuuu                                                     20

<210> SEQ ID NO 47
<211> LENGTH: 22
<212> TYPE: RNA
<213> ORGANISM: Artificial Sequence
<220> FEATURE:
<223> OTHER INFORMATION: siRNA sense strand

<400> SEQUENCE: 47
ccuuguccgu cuucuaacuc uu                                                  22

<210> SEQ ID NO 48
<211> LENGTH: 21
<212> TYPE: RNA
<213> ORGANISM: Artificial Sequence
<220> FEATURE:
<223> OTHER INFORMATION: siRNA sense strand

<400> SEQUENCE: 48
ccagguccgu caagccuaau u                                                   21

<210> SEQ ID NO 49
<211> LENGTH: 20
<212> TYPE: RNA
<213> ORGANISM: Artificial Sequence
<220> FEATURE:
<223> OTHER INFORMATION: siRNA sense strand

<400> SEQUENCE: 49
gcagcagaga aaggaaguuu                                                     20

<210> SEQ ID NO 50
<211> LENGTH: 20
<212> TYPE: RNA
<213> ORGANISM: Artificial Sequence
<220> FEATURE:
<223> OTHER INFORMATION: siRNA sense strand

<400> SEQUENCE: 50
ccuaucuccc ucagaacuuu                                                     20
```

```
<210> SEQ ID NO 51
<211> LENGTH: 22
<212> TYPE: RNA
<213> ORGANISM: Artificial Sequence
<220> FEATURE:
<223> OTHER INFORMATION: siRNA sense strand

<400> SEQUENCE: 51
gagaagcgag accuuagaag uu                                                  22

<210> SEQ ID NO 52
<211> LENGTH: 22
<212> TYPE: RNA
<213> ORGANISM: Artificial Sequence
<220> FEATURE:
<223> OTHER INFORMATION: siRNA sense strand

<400> SEQUENCE: 52
gccucaacuc uauagcucua uu                                                  22

<210> SEQ ID NO 53
<211> LENGTH: 20
<212> TYPE: RNA
<213> ORGANISM: Artificial Sequence
<220> FEATURE:
<223> OTHER INFORMATION: siRNA sense strand

<400> SEQUENCE: 53
ccaacgugga auguuucuuu                                                     20

<210> SEQ ID NO 54
<211> LENGTH: 24
<212> TYPE: RNA
<213> ORGANISM: Artificial Sequence
<220> FEATURE:
<223> OTHER INFORMATION: siRNA sense strand

<400> SEQUENCE: 54
gaagcggaag uggaagaaag uuuu                                                24

<210> SEQ ID NO 55
<211> LENGTH: 22
<212> TYPE: RNA
<213> ORGANISM: Artificial Sequence
<220> FEATURE:
<223> OTHER INFORMATION: siRNA sense strand

<400> SEQUENCE: 55
cuaguggcuu gagauuaagc uu                                                  22

<210> SEQ ID NO 56
<211> LENGTH: 22
<212> TYPE: RNA
<213> ORGANISM: Artificial Sequence
<220> FEATURE:
<223> OTHER INFORMATION: siRNA sense strand

<400> SEQUENCE: 56
ccagagaagc ugcuggugau uu                                                  22

<210> SEQ ID NO 57
<211> LENGTH: 20
<212> TYPE: RNA
<213> ORGANISM: Artificial Sequence
<220> FEATURE:
<223> OTHER INFORMATION: siRNA sense strand
```

```
<400> SEQUENCE: 57
ccacagcuga aaccgagguu                                              20

<210> SEQ ID NO 58
<211> LENGTH: 18
<212> TYPE: RNA
<213> ORGANISM: Artificial Sequence
<220> FEATURE:
<223> OTHER INFORMATION: siRNA sense strand

<400> SEQUENCE: 58
cucugcggag uucuucuu                                                18

<210> SEQ ID NO 59
<211> LENGTH: 20
<212> TYPE: RNA
<213> ORGANISM: Artificial Sequence
<220> FEATURE:
<223> OTHER INFORMATION: siRNA sense strand

<400> SEQUENCE: 59
aacuacacug ugcggaccuu                                              20

<210> SEQ ID NO 60
<211> LENGTH: 20
<212> TYPE: RNA
<213> ORGANISM: Artificial Sequence
<220> FEATURE:
<223> OTHER INFORMATION: siRNA sense strand

<400> SEQUENCE: 60
gugauguggc ucgaacaguu                                              20

<210> SEQ ID NO 61
<211> LENGTH: 22
<212> TYPE: RNA
<213> ORGANISM: Artificial Sequence
<220> FEATURE:
<223> OTHER INFORMATION: siRNA sense strand

<400> SEQUENCE: 61
gguuaaagaa ggaaauggag uu                                           22

<210> SEQ ID NO 62
<211> LENGTH: 22
<212> TYPE: RNA
<213> ORGANISM: Artificial Sequence
<220> FEATURE:
<223> OTHER INFORMATION: siRNA sense strand

<400> SEQUENCE: 62
ggaggauaug aucaucaugu uu                                           22

<210> SEQ ID NO 63
<211> LENGTH: 20
<212> TYPE: RNA
<213> ORGANISM: Artificial Sequence
<220> FEATURE:
<223> OTHER INFORMATION: siRNA sense strand

<400> SEQUENCE: 63
ggauagcuac gacgugauuu                                              20

<210> SEQ ID NO 64
```

```
<211> LENGTH: 20
<212> TYPE: RNA
<213> ORGANISM: Artificial Sequence
<220> FEATURE:
<223> OTHER INFORMATION: siRNA sense strand

<400> SEQUENCE: 64
cacagagcug cugaagaauu                                           20

<210> SEQ ID NO 65
<211> LENGTH: 20
<212> TYPE: RNA
<213> ORGANISM: Artificial Sequence
<220> FEATURE:
<223> OTHER INFORMATION: siRNA sense strand

<400> SEQUENCE: 65
ugcucuucuc ugcagagauu                                           20

<210> SEQ ID NO 66
<211> LENGTH: 21
<212> TYPE: RNA
<213> ORGANISM: Artificial Sequence
<220> FEATURE:
<223> OTHER INFORMATION: siRNA sense strand

<400> SEQUENCE: 66 gcuccucaa uucgguggu u                                           21

<210> SEQ ID NO 67
<211> LENGTH: 22
<212> TYPE: RNA
<213> ORGANISM: Artificial Sequence
<220> FEATURE:
<223> OTHER INFORMATION: siRNA sense strand

<400> SEQUENCE: 67
auucaucggu uuugccacca uu                                        22

<210> SEQ ID NO 68
<211> LENGTH: 21
<212> TYPE: RNA
<213> ORGANISM: Artificial Sequence
<220> FEATURE:
<223> OTHER INFORMATION: siRNA sense strand

<400> SEQUENCE: 68
aguggaagua caaggaugau u                                         21

<210> SEQ ID NO 69
<211> LENGTH: 20
<212> TYPE: RNA
<213> ORGANISM: Artificial Sequence
<220> FEATURE:
<223> OTHER INFORMATION: siRNA sense strand

<400> SEQUENCE: 69
cagccuuaau cuggaucauu                                           20

<210> SEQ ID NO 70
<211> LENGTH: 22
<212> TYPE: RNA
<213> ORGANISM: Artificial Sequence
<220> FEATURE:
<223> OTHER INFORMATION: siRNA sense strand

<400> SEQUENCE: 70
```

```
gucucggauc uuucagaacc uu                                              22

<210> SEQ ID NO 71
<211> LENGTH: 20
<212> TYPE: RNA
<213> ORGANISM: Artificial Sequence
<220> FEATURE:
<223> OTHER INFORMATION: siRNA sense strand

<400> SEQUENCE: 71
ggcuuuagau gaagugguuu                                                 20

<210> SEQ ID NO 72
<211> LENGTH: 20
<212> TYPE: RNA
<213> ORGANISM: Artificial Sequence
<220> FEATURE:
<223> OTHER INFORMATION: siRNA sense strand

<400> SEQUENCE: 72 guugaucgg aaccguguuu                                                  20

<210> SEQ ID NO 73
<211> LENGTH: 20
<212> TYPE: RNA
<213> ORGANISM: Artificial Sequence
<220> FEATURE:
<223> OTHER INFORMATION: siRNA sense strand

<400> SEQUENCE: 73
uuguggucca uggaaacguu                                                 20

<210> SEQ ID NO 74
<211> LENGTH: 21
<212> TYPE: RNA
<213> ORGANISM: Artificial Sequence
<220> FEATURE:
<223> OTHER INFORMATION: siRNA sense strand

<400> SEQUENCE: 74
ccacuaagcu gcagcucaau u                                               21

<210> SEQ ID NO 75
<211> LENGTH: 21
<212> TYPE: RNA
<213> ORGANISM: Artificial Sequence
<220> FEATURE:
<223> OTHER INFORMATION: siRNA sense strand

<400> SEQUENCE: 75
ccaauggcug gacuccugau u                                               21

<210> SEQ ID NO 76
<211> LENGTH: 21
<212> TYPE: RNA
<213> ORGANISM: Artificial Sequence
<220> FEATURE:
<223> OTHER INFORMATION: siRNA sense strand

<400> SEQUENCE: 76
gcuguggcuu cugcaaccau u                                               21

<210> SEQ ID NO 77
<211> LENGTH: 20
<212> TYPE: RNA
```

```
<213> ORGANISM: Artificial Sequence
<220> FEATURE:
<223> OTHER INFORMATION: siRNA sense strand

<400> SEQUENCE: 77
guguuugugg aacagccuuu                                                    20

<210> SEQ ID NO 78
<211> LENGTH: 21
<212> TYPE: RNA
<213> ORGANISM: Artificial Sequence
<220> FEATURE:
<223> OTHER INFORMATION: siRNA sense strand

<400> SEQUENCE: 78
gcugcuacuc cuggacuauu u                                                  21

<210> SEQ ID NO 79
<211> LENGTH: 22
<212> TYPE: RNA
<213> ORGANISM: Artificial Sequence
<220> FEATURE:
<223> OTHER INFORMATION: siRNA sense strand

<400> SEQUENCE: 79
uuccugcaca caacgaggu uu                                                  22

<210> SEQ ID NO 80
<211> LENGTH: 20
<212> TYPE: RNA
<213> ORGANISM: Artificial Sequence
<220> FEATURE:
<223> OTHER INFORMATION: siRNA sense strand

<400> SEQUENCE: 80
ccacaucgcu gacuccuguu                                                    20

<210> SEQ ID NO 81
<211> LENGTH: 22
<212> TYPE: RNA
<213> ORGANISM: Artificial Sequence
<220> FEATURE:
<223> OTHER INFORMATION: siRNA sense strand

<400> SEQUENCE: 81
agcuccagga ccacuucuca uu                                                 22

<210> SEQ ID NO 82
<211> LENGTH: 20
<212> TYPE: RNA
<213> ORGANISM: Artificial Sequence
<220> FEATURE:
<223> OTHER INFORMATION: siRNA sense strand

<400> SEQUENCE: 82
auggccaugg accuguguuu                                                    20

<210> SEQ ID NO 83
<211> LENGTH: 22
<212> TYPE: RNA
<213> ORGANISM: Artificial Sequence
<220> FEATURE:
<223> OTHER INFORMATION: siRNA sense strand

<400> SEQUENCE: 83
cgagugugag uucuacuuca uu                                                 22
```

```
<210> SEQ ID NO 84
<211> LENGTH: 20
<212> TYPE: RNA
<213> ORGANISM: Artificial Sequence
<220> FEATURE:
<223> OTHER INFORMATION: siRNA sense strand

<400> SEQUENCE: 84
gcuguccuca ccaaccuguu                                                    20

<210> SEQ ID NO 85
<211> LENGTH: 20
<212> TYPE: RNA
<213> ORGANISM: Artificial Sequence
<220> FEATURE:
<223> OTHER INFORMATION: siRNA sense strand

<400> SEQUENCE: 85
cugcguaucc ucauugaguu                                                    20

<210> SEQ ID NO 86
<211> LENGTH: 20
<212> TYPE: RNA
<213> ORGANISM: Artificial Sequence
<220> FEATURE:
<223> OTHER INFORMATION: siRNA sense strand

<400> SEQUENCE: 86
gagaacagga aggugaucuu                                                    20

<210> SEQ ID NO 87
<211> LENGTH: 20
<212> TYPE: RNA
<213> ORGANISM: Artificial Sequence
<220> FEATURE:
<223> OTHER INFORMATION: siRNA sense strand

<400> SEQUENCE: 87
caagcugugg uccaacuuuu                                                    20

<210> SEQ ID NO 88
<211> LENGTH: 20
<212> TYPE: RNA
<213> ORGANISM: Artificial Sequence
<220> FEATURE:
<223> OTHER INFORMATION: siRNA sense strand

<400> SEQUENCE: 88
gaggacuacg uggagcuguu                                                    20

<210> SEQ ID NO 89
<211> LENGTH: 22
<212> TYPE: RNA
<213> ORGANISM: Artificial Sequence
<220> FEATURE:
<223> OTHER INFORMATION: siRNA sense strand

<400> SEQUENCE: 89
guguguggaa uguaccauac uu                                                 22

<210> SEQ ID NO 90
<211> LENGTH: 21
<212> TYPE: RNA
<213> ORGANISM: Artificial Sequence
<220> FEATURE:
```

<223> OTHER INFORMATION: siRNA sense strand

<400> SEQUENCE: 90
agagggaugu guucucgggu u                                     21

<210> SEQ ID NO 91
<211> LENGTH: 22
<212> TYPE: RNA
<213> ORGANISM: Artificial Sequence
<220> FEATURE:
<223> OTHER INFORMATION: siRNA sense strand

<400> SEQUENCE: 91
ccuucuguaa gagcuuucga uu                                    22

<210> SEQ ID NO 92
<211> LENGTH: 22
<212> TYPE: RNA
<213> ORGANISM: Artificial Sequence
<220> FEATURE:
<223> OTHER INFORMATION: siRNA sense strand

<400> SEQUENCE: 92
acaagggcau cuuccuccau uu                                    22

<210> SEQ ID NO 93
<211> LENGTH: 20
<212> TYPE: RNA
<213> ORGANISM: Artificial Sequence
<220> FEATURE:
<223> OTHER INFORMATION: siRNA sense strand

<400> SEQUENCE: 93
cugagcaauc agcaugaauu                                       20

<210> SEQ ID NO 94
<211> LENGTH: 20
<212> TYPE: RNA
<213> ORGANISM: Artificial Sequence
<220> FEATURE:
<223> OTHER INFORMATION: siRNA sense strand

<400> SEQUENCE: 94
ccacuuccag auacgacauu                                       20

<210> SEQ ID NO 95
<211> LENGTH: 21
<212> TYPE: RNA
<213> ORGANISM: Artificial Sequence
<220> FEATURE:
<223> OTHER INFORMATION: siRNA sense strand

<400> SEQUENCE: 95
accucuggca gaucuucgau u                                     21

<210> SEQ ID NO 96
<211> LENGTH: 20
<212> TYPE: RNA
<213> ORGANISM: Artificial Sequence
<220> FEATURE:
<223> OTHER INFORMATION: siRNA sense strand

<400> SEQUENCE: 96
cgucgacugg aaggagcauu                                       20

```
<210> SEQ ID NO 97
<211> LENGTH: 20
<212> TYPE: RNA
<213> ORGANISM: Artificial Sequence
<220> FEATURE:
<223> OTHER INFORMATION: siRNA sense strand

<400> SEQUENCE: 97
guacauccac gagaacuauu                                           20

<210> SEQ ID NO 98
<211> LENGTH: 22
<212> TYPE: RNA
<213> ORGANISM: Artificial Sequence
<220> FEATURE:
<223> OTHER INFORMATION: siRNA sense strand

<400> SEQUENCE: 98
aaggaaucgu ggagcagcca uu                                        22

<210> SEQ ID NO 99
<211> LENGTH: 20
<212> TYPE: RNA
<213> ORGANISM: Artificial Sequence
<220> FEATURE:
<223> OTHER INFORMATION: siRNA sense strand

<400> SEQUENCE: 99
cugcugucag aacaaauguu                                           20

<210> SEQ ID NO 100
<211> LENGTH: 22
<212> TYPE: RNA
<213> ORGANISM: Artificial Sequence
<220> FEATURE:
<223> OTHER INFORMATION: siRNA sense strand

<400> SEQUENCE: 100
ugugaugagc ugguggcaga uu                                        22

<210> SEQ ID NO 101
<211> LENGTH: 20
<212> TYPE: RNA
<213> ORGANISM: Artificial Sequence
<220> FEATURE:
<223> OTHER INFORMATION: siRNA sense strand

<400> SEQUENCE: 101
gcaugaggau ucaaggcuuu                                           20

<210> SEQ ID NO 102
<211> LENGTH: 21
<212> TYPE: RNA
<213> ORGANISM: Artificial Sequence
<220> FEATURE:
<223> OTHER INFORMATION: siRNA sense strand

<400> SEQUENCE: 102
cuggaggcua cgagaauguu u                                         21

<210> SEQ ID NO 103
<211> LENGTH: 20
<212> TYPE: RNA
<213> ORGANISM: Artificial Sequence
<220> FEATURE:
<223> OTHER INFORMATION: siRNA sense strand
```

```
<400> SEQUENCE: 103
uggacaucca caugaagcuu                                              20

<210> SEQ ID NO 104
<211> LENGTH: 22
<212> TYPE: RNA
<213> ORGANISM: Artificial Sequence
<220> FEATURE:
<223> OTHER INFORMATION: siRNA sense strand

<400> SEQUENCE: 104
uacgaggacc aguggcugca uu                                           22

<210> SEQ ID NO 105
<211> LENGTH: 21
<212> TYPE: RNA
<213> ORGANISM: Artificial Sequence
<220> FEATURE:
<223> OTHER INFORMATION: siRNA sense strand

<400> SEQUENCE: 105
caugaccgag agccuguuuu u                                            21

<210> SEQ ID NO 106
<211> LENGTH: 22
<212> TYPE: RNA
<213> ORGANISM: Artificial Sequence
<220> FEATURE:
<223> OTHER INFORMATION: siRNA sense strand

<400> SEQUENCE: 106
gugaugaacu uugugguucg uu                                           22

<210> SEQ ID NO 107
<211> LENGTH: 20
<212> TYPE: RNA
<213> ORGANISM: Artificial Sequence
<220> FEATURE:
<223> OTHER INFORMATION: siRNA sense strand

<400> SEQUENCE: 107
agacgagcag ccgucucuuu                                              20

<210> SEQ ID NO 108
<211> LENGTH: 22
<212> TYPE: RNA
<213> ORGANISM: Artificial Sequence
<220> FEATURE:
<223> OTHER INFORMATION: siRNA sense strand

<400> SEQUENCE: 108
gacucaucca ccuucacccu uu                                           22

<210> SEQ ID NO 109
<211> LENGTH: 22
<212> TYPE: RNA
<213> ORGANISM: Artificial Sequence
<220> FEATURE:
<223> OTHER INFORMATION: siRNA sense strand

<400> SEQUENCE: 109
uuccugcgcu acgacugugu uu                                           22

<210> SEQ ID NO 110
<211> LENGTH: 22
```

```
<212> TYPE: RNA
<213> ORGANISM: Artificial Sequence
<220> FEATURE:
<223> OTHER INFORMATION: siRNA sense strand

<400> SEQUENCE: 110
cacacgcuac aucauggugu uu                                              22

<210> SEQ ID NO 111
<211> LENGTH: 22
<212> TYPE: RNA
<213> ORGANISM: Artificial Sequence
<220> FEATURE:
<223> OTHER INFORMATION: siRNA sense strand

<400> SEQUENCE: 111
ugccauugug ccuuuuagg uu                                               22

<210> SEQ ID NO 112
<211> LENGTH: 22
<212> TYPE: RNA
<213> ORGANISM: Artificial Sequence
<220> FEATURE:
<223> OTHER INFORMATION: siRNA sense strand

<400> SEQUENCE: 112 cacuccuga guucauguuc uu                                               22

<210> SEQ ID NO 113
<211> LENGTH: 22
<212> TYPE: RNA
<213> ORGANISM: Artificial Sequence
<220> FEATURE:
<223> OTHER INFORMATION: siRNA sense strand

<400> SEQUENCE: 113
ccugaacuga auaugucacc uu                                              22

<210> SEQ ID NO 114
<211> LENGTH: 23
<212> TYPE: RNA
<213> ORGANISM: Artificial Sequence
<220> FEATURE:
<223> OTHER INFORMATION: siRNA sense strand

<400> SEQUENCE: 114
cgcagucuca cucugaauaa auu                                             23

<210> SEQ ID NO 115
<211> LENGTH: 21
<212> TYPE: RNA
<213> ORGANISM: Artificial Sequence
<220> FEATURE:
<223> OTHER INFORMATION: siRNA sense strand

<400> SEQUENCE: 115
ggacaguuug uaagucuugu u                                               21

<210> SEQ ID NO 116
<211> LENGTH: 22
<212> TYPE: RNA
<213> ORGANISM: Artificial Sequence
<220> FEATURE:
<223> OTHER INFORMATION: siRNA sense strand

<400> SEQUENCE: 116
```
ucacuucccc uguccagguu uu                                                    22

<210> SEQ ID NO 117
<211> LENGTH: 22
<212> TYPE: RNA
<213> ORGANISM: Artificial Sequence
<220> FEATURE:
<223> OTHER INFORMATION: siRNA sense strand

<400> SEQUENCE: 117
ucagcuucca caugugucaa uu                                                    22

<210> SEQ ID NO 118
<211> LENGTH: 21
<212> TYPE: RNA
<213> ORGANISM: Artificial Sequence
<220> FEATURE:
<223> OTHER INFORMATION: siRNA sense strand

<400> SEQUENCE: 118
gacaauccuc gccuugucuu u                                                     21

<210> SEQ ID NO 119
<211> LENGTH: 21
<212> TYPE: RNA
<213> ORGANISM: Artificial Sequence
<220> FEATURE:
<223> OTHER INFORMATION: siRNA sense strand

<400> SEQUENCE: 119
gcaucuggag cuuucuguau u                                                     21

<210> SEQ ID NO 120
<211> LENGTH: 20
<212> TYPE: RNA
<213> ORGANISM: Artificial Sequence
<220> FEATURE:
<223> OTHER INFORMATION: siRNA sense strand

<400> SEQUENCE: 120
gagaucccag gauccugguu                                                       20

<210> SEQ ID NO 121
<211> LENGTH: 22
<212> TYPE: RNA
<213> ORGANISM: Artificial Sequence
<220> FEATURE:
<223> OTHER INFORMATION: siRNA sense strand

<400> SEQUENCE: 121
aaucaggaug ccacugugua uu                                                    22

<210> SEQ ID NO 122
<211> LENGTH: 22
<212> TYPE: RNA
<213> ORGANISM: Artificial Sequence
<220> FEATURE:
<223> OTHER INFORMATION: siRNA sense strand

<400> SEQUENCE: 122
cuggaugaga agguuaguga uu                                                    22

<210> SEQ ID NO 123
<211> LENGTH: 22
<212> TYPE: RNA
<213> ORGANISM: Artificial Sequence

```
<220> FEATURE:
<223> OTHER INFORMATION: siRNA sense strand

<400> SEQUENCE: 123
ugugggaacu guuucuccag uu                                    22

<210> SEQ ID NO 124
<211> LENGTH: 20
<212> TYPE: RNA
<213> ORGANISM: Artificial Sequence
<220> FEATURE:
<223> OTHER INFORMATION: siRNA sense strand

<400> SEQUENCE: 124
cuggaccagu agucaacauu                                       20

<210> SEQ ID NO 125
<211> LENGTH: 21
<212> TYPE: RNA
<213> ORGANISM: Artificial Sequence
<220> FEATURE:
<223> OTHER INFORMATION: siRNA sense strand

<400> SEQUENCE: 125
ccaaaggaua gagucacugu u                                     21

<210> SEQ ID NO 126
<211> LENGTH: 23
<212> TYPE: RNA
<213> ORGANISM: Artificial Sequence
<220> FEATURE:
<223> OTHER INFORMATION: siRNA sense strand

<400> SEQUENCE: 126
cagcaccaag gcuauggcuu uuu                                   23

<210> SEQ ID NO 127
<211> LENGTH: 22
<212> TYPE: RNA
<213> ORGANISM: Artificial Sequence
<220> FEATURE:
<223> OTHER INFORMATION: siRNA sense strand

<400> SEQUENCE: 127
guggaauucu ugagugagga uu                                    22

<210> SEQ ID NO 128
<211> LENGTH: 22
<212> TYPE: RNA
<213> ORGANISM: Artificial Sequence
<220> FEATURE:
<223> OTHER INFORMATION: siRNA sense strand

<400> SEQUENCE: 128
gcugacuaug ccauuaagau uu                                    22

<210> SEQ ID NO 129
<211> LENGTH: 21
<212> TYPE: RNA
<213> ORGANISM: Artificial Sequence
<220> FEATURE:
<223> OTHER INFORMATION: siRNA sense strand

<400> SEQUENCE: 129
acaugaucaa acucuauggu u                                     21
```

<210> SEQ ID NO 130
<211> LENGTH: 20
<212> TYPE: RNA
<213> ORGANISM: Artificial Sequence
<220> FEATURE:
<223> OTHER INFORMATION: siRNA sense strand

<400> SEQUENCE: 130
ggugaacaaa gcaucagcuu                                               20

<210> SEQ ID NO 131
<211> LENGTH: 20
<212> TYPE: RNA
<213> ORGANISM: Artificial Sequence
<220> FEATURE:
<223> OTHER INFORMATION: siRNA sense strand

<400> SEQUENCE: 131
ccugagauug augagaaguu                                               20

<210> SEQ ID NO 132
<211> LENGTH: 19
<212> TYPE: RNA
<213> ORGANISM: Artificial Sequence
<220> FEATURE:
<223> OTHER INFORMATION: siRNA sense strand

<400> SEQUENCE: 132
ggucaucuua caaacccuu                                                19

<210> SEQ ID NO 133
<211> LENGTH: 20
<212> TYPE: RNA
<213> ORGANISM: Artificial Sequence
<220> FEATURE:
<223> OTHER INFORMATION: siRNA sense strand

<400> SEQUENCE: 133
ccugacacag gcaacuccuu                                               20

<210> SEQ ID NO 134
<211> LENGTH: 22
<212> TYPE: RNA
<213> ORGANISM: Artificial Sequence
<220> FEATURE:
<223> OTHER INFORMATION: siRNA sense strand

<400> SEQUENCE: 134
gcuucauuug augcuucgga uu                                            22

<210> SEQ ID NO 135
<211> LENGTH: 22
<212> TYPE: RNA
<213> ORGANISM: Artificial Sequence
<220> FEATURE:
<223> OTHER INFORMATION: siRNA sense strand

<400> SEQUENCE: 135
ugcagcaauu gaagccauga uu                                            22

<210> SEQ ID NO 136
<211> LENGTH: 21
<212> TYPE: RNA
<213> ORGANISM: Artificial Sequence
<220> FEATURE:
<223> OTHER INFORMATION: siRNA sense strand

```
<400> SEQUENCE: 136
gcaguaccuc uguaaccguu u                                         21

<210> SEQ ID NO 137
<211> LENGTH: 22
<212> TYPE: RNA
<213> ORGANISM: Artificial Sequence
<220> FEATURE:
<223> OTHER INFORMATION: siRNA sense strand

<400> SEQUENCE: 137
caccguaucu uaugccuuca uu                                        22

<210> SEQ ID NO 138
<211> LENGTH: 22
<212> TYPE: RNA
<213> ORGANISM: Artificial Sequence
<220> FEATURE:
<223> OTHER INFORMATION: siRNA sense strand

<400> SEQUENCE: 138
gaacgacuuc uggcagcuca uu                                        22

<210> SEQ ID NO 139
<211> LENGTH: 22
<212> TYPE: RNA
<213> ORGANISM: Artificial Sequence
<220> FEATURE:
<223> OTHER INFORMATION: siRNA sense strand

<400> SEQUENCE: 139
ccucaucagc uguuugcaga uu                                        22

<210> SEQ ID NO 140
<211> LENGTH: 22
<212> TYPE: RNA
<213> ORGANISM: Artificial Sequence
<220> FEATURE:
<223> OTHER INFORMATION: siRNA sense strand

<400> SEQUENCE: 140
uggucaugga cacucacauc uu                                        22

<210> SEQ ID NO 141
<211> LENGTH: 20
<212> TYPE: RNA
<213> ORGANISM: Artificial Sequence
<220> FEATURE:
<223> OTHER INFORMATION: siRNA sense strand

<400> SEQUENCE: 141
gaugucucag augcagcuuu                                           20

<210> SEQ ID NO 142
<211> LENGTH: 20
<212> TYPE: RNA
<213> ORGANISM: Artificial Sequence
<220> FEATURE:
<223> OTHER INFORMATION: siRNA sense strand

<400> SEQUENCE: 142
ccucauggcu uaggacauuu                                           20

<210> SEQ ID NO 143
```

<210> SEQ ID NO 143
<211> LENGTH: 22
<212> TYPE: RNA
<213> ORGANISM: Artificial Sequence
<220> FEATURE:
<223> OTHER INFORMATION: siRNA sense strand

<400> SEQUENCE: 143
ucacauuuuc cuuccuccug uu                                            22

<210> SEQ ID NO 144
<211> LENGTH: 22
<212> TYPE: RNA
<213> ORGANISM: Artificial Sequence
<220> FEATURE:
<223> OTHER INFORMATION: siRNA sense strand

<400> SEQUENCE: 144
ccuuggacca aucagagaug uu                                            22

<210> SEQ ID NO 145
<211> LENGTH: 22
<212> TYPE: RNA
<213> ORGANISM: Artificial Sequence
<220> FEATURE:
<223> OTHER INFORMATION: siRNA sense strand

<400> SEQUENCE: 145
ggcaaaggua cuaaucccuu uu                                            22

<210> SEQ ID NO 146
<211> LENGTH: 20
<212> TYPE: RNA
<213> ORGANISM: Artificial Sequence
<220> FEATURE:
<223> OTHER INFORMATION: siRNA sense strand

<400> SEQUENCE: 146
uuccacagga gguauuucuu                                               20

<210> SEQ ID NO 147
<211> LENGTH: 20
<212> TYPE: RNA
<213> ORGANISM: Artificial Sequence
<220> FEATURE:
<223> OTHER INFORMATION: siRNA sense strand

<400> SEQUENCE: 147
gguccugagu auuuugcauu                                               20

<210> SEQ ID NO 148
<211> LENGTH: 21
<212> TYPE: RNA
<213> ORGANISM: Artificial Sequence
<220> FEATURE:
<223> OTHER INFORMATION: siRNA sense strand

<400> SEQUENCE: 148
ccaaaucugc aagaaggcuu u                                             21

<210> SEQ ID NO 149
<211> LENGTH: 23
<212> TYPE: RNA
<213> ORGANISM: Artificial Sequence
<220> FEATURE:
<223> OTHER INFORMATION: siRNA sense strand

<400> SEQUENCE: 149

```
ggaacucuuc agcacauccu uuu                                              23

<210> SEQ ID NO 150
<211> LENGTH: 22
<212> TYPE: RNA
<213> ORGANISM: Artificial Sequence
<220> FEATURE:
<223> OTHER INFORMATION: siRNA sense strand

<400> SEQUENCE: 150
cucuggacaa cagaagaaga uu                                               22

<210> SEQ ID NO 151
<211> LENGTH: 20
<212> TYPE: RNA
<213> ORGANISM: Artificial Sequence
<220> FEATURE:
<223> OTHER INFORMATION: siRNA sense strand

<400> SEQUENCE: 151
ugagagcagu gugauucuuu                                                  20

<210> SEQ ID NO 152
<211> LENGTH: 19
<212> TYPE: RNA
<213> ORGANISM: Artificial Sequence
<220> FEATURE:
<223> OTHER INFORMATION: siRNA sense strand

<400> SEQUENCE: 152
caagucuagc agugcauuu                                                   19

<210> SEQ ID NO 153
<211> LENGTH: 21
<212> TYPE: RNA
<213> ORGANISM: Artificial Sequence
<220> FEATURE:
<223> OTHER INFORMATION: siRNA sense strand

<400> SEQUENCE: 153
cucgcuaaga caacuagcau u                                                21

<210> SEQ ID NO 154
<211> LENGTH: 22
<212> TYPE: RNA
<213> ORGANISM: Artificial Sequence
<220> FEATURE:
<223> OTHER INFORMATION: siRNA sense strand

<400> SEQUENCE: 154
cagguuaagu uucggaggcu uu                                               22

<210> SEQ ID NO 155
<211> LENGTH: 22
<212> TYPE: RNA
<213> ORGANISM: Artificial Sequence
<220> FEATURE:
<223> OTHER INFORMATION: siRNA sense strand

<400> SEQUENCE: 155
gcuuccaggc accuccucuu uu                                               22

<210> SEQ ID NO 156
<211> LENGTH: 22
<212> TYPE: RNA
```

```
<213> ORGANISM: Artificial Sequence
<220> FEATURE:
<223> OTHER INFORMATION: siRNA sense strand

<400> SEQUENCE: 156
gaaguggaag ucgugcugag uu                                              22

<210> SEQ ID NO 157
<211> LENGTH: 22
<212> TYPE: RNA
<213> ORGANISM: Artificial Sequence
<220> FEATURE:
<223> OTHER INFORMATION: siRNA sense strand

<400> SEQUENCE: 157
gaucucuuuc gccauggcug uu                                              22

<210> SEQ ID NO 158
<211> LENGTH: 27
<212> TYPE: RNA
<213> ORGANISM: Artificial Sequence
<220> FEATURE:
<223> OTHER INFORMATION: dsRNA

<400> SEQUENCE: 158
caagaagcug gaggaaaguu ucuaaag                                         27

<210> SEQ ID NO 159
<211> LENGTH: 29
<212> TYPE: RNA
<213> ORGANISM: Artificial Sequence
<220> FEATURE:
<223> OTHER INFORMATION: dsRNA

<400> SEQUENCE: 159
gaaagaugaa gaccucuucc uuucuaaag                                       29

<210> SEQ ID NO 160
<211> LENGTH: 29
<212> TYPE: RNA
<213> ORGANISM: Artificial Sequence
<220> FEATURE:
<223> OTHER INFORMATION: dsRNA

<400> SEQUENCE: 160
ggaauggcug aaagacacuu uuucuaaag                                       29

<210> SEQ ID NO 161
<211> LENGTH: 27
<212> TYPE: RNA
<213> ORGANISM: Artificial Sequence
<220> FEATURE:
<223> OTHER INFORMATION: dsRNA

<400> SEQUENCE: 161
ccaguguucc caguucccuu ucuaaag                                         27

<210> SEQ ID NO 162
<211> LENGTH: 27
<212> TYPE: RNA
<213> ORGANISM: Artificial Sequence
<220> FEATURE:
<223> OTHER INFORMATION: dsRNA

<400> SEQUENCE: 162
ccaguccaac ugcgaggauu ucuaaag                                         27
```

<210> SEQ ID NO 163
<211> LENGTH: 27
<212> TYPE: RNA
<213> ORGANISM: Artificial Sequence
<220> FEATURE:
<223> OTHER INFORMATION: dsRNA

<400> SEQUENCE: 163
cgacgugagu cugagucuuu ucuaaag                                          27

<210> SEQ ID NO 164
<211> LENGTH: 27
<212> TYPE: RNA
<213> ORGANISM: Artificial Sequence
<220> FEATURE:
<223> OTHER INFORMATION: dsRNA

<400> SEQUENCE: 164
guccgucuuc uaacucuuuu ucuaaag                                          27

<210> SEQ ID NO 165
<211> LENGTH: 27
<212> TYPE: RNA
<213> ORGANISM: Artificial Sequence
<220> FEATURE:
<223> OTHER INFORMATION: dsRNA

<400> SEQUENCE: 165
cgucaagccu aaguccuuuu ucuaaag                                          27

<210> SEQ ID NO 166
<211> LENGTH: 27
<212> TYPE: RNA
<213> ORGANISM: Artificial Sequence
<220> FEATURE:
<223> OTHER INFORMATION: dsRNA

<400> SEQUENCE: 166
gcagagaaag gaaguccuuu ucuaaag                                          27

<210> SEQ ID NO 167
<211> LENGTH: 27
<212> TYPE: RNA
<213> ORGANISM: Artificial Sequence
<220> FEATURE:
<223> OTHER INFORMATION: dsRNA

<400> SEQUENCE: 167
cgagaagcga gaccuuaguu ucuaaag                                          27

<210> SEQ ID NO 168
<211> LENGTH: 27
<212> TYPE: RNA
<213> ORGANISM: Artificial Sequence
<220> FEATURE:
<223> OTHER INFORMATION: dsRNA

<400> SEQUENCE: 168
ccucaacucu auagcucuuu ucuaaag                                          27

<210> SEQ ID NO 169
<211> LENGTH: 27
<212> TYPE: RNA
<213> ORGANISM: Artificial Sequence
<220> FEATURE:

-continued

<223> OTHER INFORMATION: dsRNA

<400> SEQUENCE: 169
cuaguggcuu gagguaucuu ucuaaag                                               27

<210> SEQ ID NO 170
<211> LENGTH: 27
<212> TYPE: RNA
<213> ORGANISM: Artificial Sequence
<220> FEATURE:
<223> OTHER INFORMATION: dsRNA

<400> SEQUENCE: 170
ggauuaagcc ugaucaaguu ucuaaag                                               27

<210> SEQ ID NO 171
<211> LENGTH: 27
<212> TYPE: RNA
<213> ORGANISM: Artificial Sequence
<220> FEATURE:
<223> OTHER INFORMATION: dsRNA

<400> SEQUENCE: 171
gacugcuucg gaugccuuuu ucuaaag                                               27

<210> SEQ ID NO 172
<211> LENGTH: 27
<212> TYPE: RNA
<213> ORGANISM: Artificial Sequence
<220> FEATURE:
<223> OTHER INFORMATION: dsRNA

<400> SEQUENCE: 172
ccuucuugug augcucucuu ucuaaag                                               27

<210> SEQ ID NO 173
<211> LENGTH: 27
<212> TYPE: RNA
<213> ORGANISM: Artificial Sequence
<220> FEATURE:
<223> OTHER INFORMATION: dsRNA

<400> SEQUENCE: 173
ccucauccag aguuugcauu ucuaaag                                               27

<210> SEQ ID NO 174
<211> LENGTH: 27
<212> TYPE: RNA
<213> ORGANISM: Artificial Sequence
<220> FEATURE:
<223> OTHER INFORMATION: dsRNA

<400> SEQUENCE: 174
ccuguccucu acgaaggauu ucuaaag                                               27

<210> SEQ ID NO 175
<211> LENGTH: 29
<212> TYPE: RNA
<213> ORGANISM: Artificial Sequence
<220> FEATURE:
<223> OTHER INFORMATION: dsRNA

<400> SEQUENCE: 175
gauugcuauu gucguacuca uuucuaaag                                             29

```
<210> SEQ ID NO 176
<211> LENGTH: 27
<212> TYPE: RNA
<213> ORGANISM: Artificial Sequence
<220> FEATURE:
<223> OTHER INFORMATION: dsRNA

<400> SEQUENCE: 176
ggauucucgc ucuugcauuu ucuaaag                                            27

<210> SEQ ID NO 177
<211> LENGTH: 27
<212> TYPE: RNA
<213> ORGANISM: Artificial Sequence
<220> FEATURE:
<223> OTHER INFORMATION: dsRNA

<400> SEQUENCE: 177
ggugacaguu accagcuuuu ucuaaag                                            27

<210> SEQ ID NO 178
<211> LENGTH: 27
<212> TYPE: RNA
<213> ORGANISM: Artificial Sequence
<220> FEATURE:
<223> OTHER INFORMATION: dsRNA

<400> SEQUENCE: 178
ccucacuuuc aauccguuuu ucuaaag                                            27

<210> SEQ ID NO 179
<211> LENGTH: 27
<212> TYPE: RNA
<213> ORGANISM: Artificial Sequence
<220> FEATURE:
<223> OTHER INFORMATION: dsRNA

<400> SEQUENCE: 179
gcagaacagu cacuguccuu ucuaaag                                            27

<210> SEQ ID NO 180
<211> LENGTH: 29
<212> TYPE: RNA
<213> ORGANISM: Artificial Sequence
<220> FEATURE:
<223> OTHER INFORMATION: dsRNA

<400> SEQUENCE: 180
gaucaauaaa gucaguggcu uuucuaaag                                          29

<210> SEQ ID NO 181
<211> LENGTH: 30
<212> TYPE: RNA
<213> ORGANISM: Artificial Sequence
<220> FEATURE:
<223> OTHER INFORMATION: dsRNA

<400> SEQUENCE: 181
aagaagcugg aggaaagggg uuuucuaaag                                         30

<210> SEQ ID NO 182
<211> LENGTH: 29
<212> TYPE: RNA
<213> ORGANISM: Artificial Sequence
<220> FEATURE:
<223> OTHER INFORMATION: dsRNA
```

```
<400> SEQUENCE: 182
augacaaccu cccaaaagca uucuaaag                                29

<210> SEQ ID NO 183
<211> LENGTH: 27
<212> TYPE: RNA
<213> ORGANISM: Artificial Sequence
<220> FEATURE:
<223> OTHER INFORMATION: dsRNA

<400> SEQUENCE: 183
ccgagacuuc guggcagauu ucuaaag                                 27

<210> SEQ ID NO 184
<211> LENGTH: 24
<212> TYPE: RNA
<213> ORGANISM: Artificial Sequence
<220> FEATURE:
<223> OTHER INFORMATION: dsRNA

<400> SEQUENCE: 184
agccuggcug ggauuuuucu aaag                                    24

<210> SEQ ID NO 185
<211> LENGTH: 26
<212> TYPE: RNA
<213> ORGANISM: Artificial Sequence
<220> FEATURE:
<223> OTHER INFORMATION: dsRNA

<400> SEQUENCE: 185
caagaagcug gaggaaauuu cuaaag                                  26

<210> SEQ ID NO 186
<211> LENGTH: 29
<212> TYPE: RNA
<213> ORGANISM: Artificial Sequence
<220> FEATURE:
<223> OTHER INFORMATION: dsRNA

<400> SEQUENCE: 186
ccaguuucug gugcuaaaga uucuaaag                                29

<210> SEQ ID NO 187
<211> LENGTH: 27
<212> TYPE: RNA
<213> ORGANISM: Artificial Sequence
<220> FEATURE:
<223> OTHER INFORMATION: dsRNA

<400> SEQUENCE: 187
aagaugaaga ccucuuccuu ucuaaag                                 27

<210> SEQ ID NO 188
<211> LENGTH: 28
<212> TYPE: RNA
<213> ORGANISM: Artificial Sequence
<220> FEATURE:
<223> OTHER INFORMATION: dsRNA

<400> SEQUENCE: 188
ggacugcuuc ggaugccuuu uucuaaag                                28

<210> SEQ ID NO 189
<211> LENGTH: 30
```

-continued

```
<212> TYPE: RNA
<213> ORGANISM: Artificial Sequence
<220> FEATURE:
<223> OTHER INFORMATION: dsRNA

<400> SEQUENCE: 189
aguggugcga cgccuucuuu uuucuaaag                                           30

<210> SEQ ID NO 190
<211> LENGTH: 28
<212> TYPE: RNA
<213> ORGANISM: Artificial Sequence
<220> FEATURE:
<223> OTHER INFORMATION: dsRNA

<400> SEQUENCE: 190
aguggugcga cgccuucuuu uucuaaag                                            28

<210> SEQ ID NO 191
<211> LENGTH: 29
<212> TYPE: RNA
<213> ORGANISM: Artificial Sequence
<220> FEATURE:
<223> OTHER INFORMATION: dsRNA

<400> SEQUENCE: 191
uugcuauugu cguacucacc uuucuaaag                                           29

<210> SEQ ID NO 192
<211> LENGTH: 27
<212> TYPE: RNA
<213> ORGANISM: Artificial Sequence
<220> FEATURE:
<223> OTHER INFORMATION: dsRNA

<400> SEQUENCE: 192
gauucucgcu cuugcauguu ucuaaag                                             27

<210> SEQ ID NO 193
<211> LENGTH: 29
<212> TYPE: RNA
<213> ORGANISM: Artificial Sequence
<220> FEATURE:
<223> OTHER INFORMATION: dsRNA

<400> SEQUENCE: 193
caguucccug gugacaguua uuucuaaag                                           29

<210> SEQ ID NO 194
<211> LENGTH: 27
<212> TYPE: RNA
<213> ORGANISM: Artificial Sequence
<220> FEATURE:
<223> OTHER INFORMATION: dsRNA

<400> SEQUENCE: 194
ccagcuuucc ugaauggauu ucuaaag                                             27

<210> SEQ ID NO 195
<211> LENGTH: 29
<212> TYPE: RNA
<213> ORGANISM: Artificial Sequence
<220> FEATURE:
<223> OTHER INFORMATION: dsRNA

<400> SEQUENCE: 195
```
cucacuuuca auccguuuga uuucuaaag                                                29

<210> SEQ ID NO 196
<211> LENGTH: 29
<212> TYPE: RNA
<213> ORGANISM: Artificial Sequence
<220> FEATURE:
<223> OTHER INFORMATION: dsRNA

<400> SEQUENCE: 196
cagaacaguc acguccuug uuucuaaag                                                 29

<210> SEQ ID NO 197
<211> LENGTH: 27
<212> TYPE: RNA
<213> ORGANISM: Artificial Sequence
<220> FEATURE:
<223> OTHER INFORMATION: dsRNA

<400> SEQUENCE: 197
caccagucca acugcgaguu ucuaaag                                                  27

<210> SEQ ID NO 198
<211> LENGTH: 29
<212> TYPE: RNA
<213> ORGANISM: Artificial Sequence
<220> FEATURE:
<223> OTHER INFORMATION: dsRNA

<400> SEQUENCE: 198
ugcgacguga gucugagucu uuucuaaag                                                29

<210> SEQ ID NO 199
<211> LENGTH: 27
<212> TYPE: RNA
<213> ORGANISM: Artificial Sequence
<220> FEATURE:
<223> OTHER INFORMATION: dsRNA

<400> SEQUENCE: 199
ccuccgaaaa ccguacuuuu ucuaaag                                                  27

<210> SEQ ID NO 200
<211> LENGTH: 29
<212> TYPE: RNA
<213> ORGANISM: Artificial Sequence
<220> FEATURE:
<223> OTHER INFORMATION: dsRNA

<400> SEQUENCE: 200
ccuuguccgu cuucuaacuc uuucuaaag                                                29

<210> SEQ ID NO 201
<211> LENGTH: 28
<212> TYPE: RNA
<213> ORGANISM: Artificial Sequence
<220> FEATURE:
<223> OTHER INFORMATION: dsRNA

<400> SEQUENCE: 201
ccagguccgu caagccuaau uucuaaag                                                 28

<210> SEQ ID NO 202
<211> LENGTH: 27
<212> TYPE: RNA
<213> ORGANISM: Artificial Sequence

```
<220> FEATURE:
<223> OTHER INFORMATION: dsRNA

<400> SEQUENCE: 202
gcagcagaga aaggaaguuu ucuaaag                                              27

<210> SEQ ID NO 203
<211> LENGTH: 27
<212> TYPE: RNA
<213> ORGANISM: Artificial Sequence
<220> FEATURE:
<223> OTHER INFORMATION: dsRNA

<400> SEQUENCE: 203
ccuaucuccc ucagaacuuu ucuaaag                                              27

<210> SEQ ID NO 204
<211> LENGTH: 29
<212> TYPE: RNA
<213> ORGANISM: Artificial Sequence
<220> FEATURE:
<223> OTHER INFORMATION: dsRNA

<400> SEQUENCE: 204
gagaagcgag accuuagaag uuucuaaag                                            29

<210> SEQ ID NO 205
<211> LENGTH: 29
<212> TYPE: RNA
<213> ORGANISM: Artificial Sequence
<220> FEATURE:
<223> OTHER INFORMATION: dsRNA

<400> SEQUENCE: 205
gccucaacuc uauagcucua uuucuaaag                                            29

<210> SEQ ID NO 206
<211> LENGTH: 27
<212> TYPE: RNA
<213> ORGANISM: Artificial Sequence
<220> FEATURE:
<223> OTHER INFORMATION: dsRNA

<400> SEQUENCE: 206
ccaacgugga auguuucuuu ucuaaag                                              27

<210> SEQ ID NO 207
<211> LENGTH: 31
<212> TYPE: RNA
<213> ORGANISM: Artificial Sequence
<220> FEATURE:
<223> OTHER INFORMATION: dsRNA

<400> SEQUENCE: 207
gaagcggaag uggaagaaag uuuuucuaaa g                                         31

<210> SEQ ID NO 208
<211> LENGTH: 29
<212> TYPE: RNA
<213> ORGANISM: Artificial Sequence
<220> FEATURE:
<223> OTHER INFORMATION: dsRNA

<400> SEQUENCE: 208
cuaguggcuu gagauuaagc uuucuaaag                                            29
```

<210> SEQ ID NO 209
<211> LENGTH: 29
<212> TYPE: RNA
<213> ORGANISM: Artificial Sequence
<220> FEATURE:
<223> OTHER INFORMATION: dsRNA

<400> SEQUENCE: 209
ccagagaagc ugcuggugau uuucuaaag                    29

<210> SEQ ID NO 210
<211> LENGTH: 27
<212> TYPE: RNA
<213> ORGANISM: Artificial Sequence
<220> FEATURE:
<223> OTHER INFORMATION: dsRNA

<400> SEQUENCE: 210
ccacagcuga aaccgagguu ucuaaag                      27

<210> SEQ ID NO 211
<211> LENGTH: 25
<212> TYPE: RNA
<213> ORGANISM: Artificial Sequence
<220> FEATURE:
<223> OTHER INFORMATION: dsRNA

<400> SEQUENCE: 211
cucugcggag uucuucuuuc uaaag                        25

<210> SEQ ID NO 212
<211> LENGTH: 27
<212> TYPE: RNA
<213> ORGANISM: Artificial Sequence
<220> FEATURE:
<223> OTHER INFORMATION: dsRNA

<400> SEQUENCE: 212
aacuacacug ugcggaccuu ucuaaag                      27

<210> SEQ ID NO 213
<211> LENGTH: 27
<212> TYPE: RNA
<213> ORGANISM: Artificial Sequence
<220> FEATURE:
<223> OTHER INFORMATION: dsRNA

<400> SEQUENCE: 213
gugauguggc ucgaacaguu ucuaaag                      27

<210> SEQ ID NO 214
<211> LENGTH: 29
<212> TYPE: RNA
<213> ORGANISM: Artificial Sequence
<220> FEATURE:
<223> OTHER INFORMATION: dsRNA

<400> SEQUENCE: 214
gguuaaagaa ggaaauggag uuucuaaag                    29

<210> SEQ ID NO 215
<211> LENGTH: 29
<212> TYPE: RNA
<213> ORGANISM: Artificial Sequence
<220> FEATURE:
<223> OTHER INFORMATION: dsRNA

```
<400> SEQUENCE: 215
ggaggauaug aucaucaugu uuucuaaag                                          29

<210> SEQ ID NO 216
<211> LENGTH: 27
<212> TYPE: RNA
<213> ORGANISM: Artificial Sequence
<220> FEATURE:
<223> OTHER INFORMATION: dsRNA

<400> SEQUENCE: 216
ggauagcuac gacgugauuu ucuaaag                                            27

<210> SEQ ID NO 217
<211> LENGTH: 27
<212> TYPE: RNA
<213> ORGANISM: Artificial Sequence
<220> FEATURE:
<223> OTHER INFORMATION: dsRNA

<400> SEQUENCE: 217
cacagagcug cugaagaauu ucuaaag                                            27

<210> SEQ ID NO 218
<211> LENGTH: 27
<212> TYPE: RNA
<213> ORGANISM: Artificial Sequence
<220> FEATURE:
<223> OTHER INFORMATION: dsRNA

<400> SEQUENCE: 218
ugcucuucuc ugcagagauu ucuaaag                                            27

<210> SEQ ID NO 219
<211> LENGTH: 28
<212> TYPE: RNA
<213> ORGANISM: Artificial Sequence
<220> FEATURE:
<223> OTHER INFORMATION: dsRNA

<400> SEQUENCE: 219
gcuuccucaa uucggguggu uucuaaag                                           28

<210> SEQ ID NO 220
<211> LENGTH: 29
<212> TYPE: RNA
<213> ORGANISM: Artificial Sequence
<220> FEATURE:
<223> OTHER INFORMATION: dsRNA

<400> SEQUENCE: 220
auucaucggu uuugccacca uuucuaaag                                          29

<210> SEQ ID NO 221
<211> LENGTH: 28
<212> TYPE: RNA
<213> ORGANISM: Artificial Sequence
<220> FEATURE:
<223> OTHER INFORMATION: dsRNA

<400> SEQUENCE: 221
aguggaagua caaggaugau uucuaaag                                           28

<210> SEQ ID NO 222
```

```
<211> LENGTH: 27
<212> TYPE: RNA
<213> ORGANISM: Artificial Sequence
<220> FEATURE:
<223> OTHER INFORMATION: dsRNA

<400> SEQUENCE: 222
cagccuuaau cuggaucauu ucuaaag                                          27

<210> SEQ ID NO 223
<211> LENGTH: 29
<212> TYPE: RNA
<213> ORGANISM: Artificial Sequence
<220> FEATURE:
<223> OTHER INFORMATION: dsRNA

<400> SEQUENCE: 223
gucucggauc uuucagaacc uuucuaaag                                        29

<210> SEQ ID NO 224
<211> LENGTH: 27
<212> TYPE: RNA
<213> ORGANISM: Artificial Sequence
<220> FEATURE:
<223> OTHER INFORMATION: dsRNA

<400> SEQUENCE: 224
ggcuuuagau gaagugguuu ucuaaag                                          27

<210> SEQ ID NO 225
<211> LENGTH: 27
<212> TYPE: RNA
<213> ORGANISM: Artificial Sequence
<220> FEATURE:
<223> OTHER INFORMATION: dsRNA

<400> SEQUENCE: 225
guuugaucgg aaccguguuu ucuaaag                                          27

<210> SEQ ID NO 226
<211> LENGTH: 27
<212> TYPE: RNA
<213> ORGANISM: Artificial Sequence
<220> FEATURE:
<223> OTHER INFORMATION: dsRNA

<400> SEQUENCE: 226
uuguggucca uggaaacguu ucuaaag                                          27

<210> SEQ ID NO 227
<211> LENGTH: 28
<212> TYPE: RNA
<213> ORGANISM: Artificial Sequence
<220> FEATURE:
<223> OTHER INFORMATION: dsRNA

<400> SEQUENCE: 227
ccacuaagcu gcagcucaau uucuaaag                                         28

<210> SEQ ID NO 228
<211> LENGTH: 28
<212> TYPE: RNA
<213> ORGANISM: Artificial Sequence
<220> FEATURE:
<223> OTHER INFORMATION: dsRNA

<400> SEQUENCE: 228
```
ccaauggcug gacuccugau uucuaaag                                               28

<210> SEQ ID NO 229
<211> LENGTH: 28
<212> TYPE: RNA
<213> ORGANISM: Artificial Sequence
<220> FEATURE:
<223> OTHER INFORMATION: dsRNA

<400> SEQUENCE: 229
gcuguggcuu cugcaaccau uucuaaag                                               28

<210> SEQ ID NO 230
<211> LENGTH: 27
<212> TYPE: RNA
<213> ORGANISM: Artificial Sequence
<220> FEATURE:
<223> OTHER INFORMATION: dsRNA

<400> SEQUENCE: 230
guguuugugg aacagccuuu ucuaaag                                                27

<210> SEQ ID NO 231
<211> LENGTH: 28
<212> TYPE: RNA
<213> ORGANISM: Artificial Sequence
<220> FEATURE:
<223> OTHER INFORMATION: dsRNA

<400> SEQUENCE: 231
gcugcuacuc cuggacuauu uucuaaag                                               28

<210> SEQ ID NO 232
<211> LENGTH: 29
<212> TYPE: RNA
<213> ORGANISM: Artificial Sequence
<220> FEATURE:
<223> OTHER INFORMATION: dsRNA

<400> SEQUENCE: 232
uuccugcaca acaacgaggu uuucuaaag                                              29

<210> SEQ ID NO 233
<211> LENGTH: 27
<212> TYPE: RNA
<213> ORGANISM: Artificial Sequence
<220> FEATURE:
<223> OTHER INFORMATION: dsRNA

<400> SEQUENCE: 233
ccacaucgcu gacuccuguu ucuaaag                                                27

<210> SEQ ID NO 234
<211> LENGTH: 29
<212> TYPE: RNA
<213> ORGANISM: Artificial Sequence
<220> FEATURE:
<223> OTHER INFORMATION: dsRNA

<400> SEQUENCE: 234
agcuccagga ccacuucuca uuucuaaag                                              29

<210> SEQ ID NO 235
<211> LENGTH: 27
<212> TYPE: RNA

```
<213> ORGANISM: Artificial Sequence
<220> FEATURE:
<223> OTHER INFORMATION: dsRNA

<400> SEQUENCE: 235
auggccaugg accuguguuu ucuaaag                                              27

<210> SEQ ID NO 236
<211> LENGTH: 29
<212> TYPE: RNA
<213> ORGANISM: Artificial Sequence
<220> FEATURE:
<223> OTHER INFORMATION: dsRNA

<400> SEQUENCE: 236
cgagugugag uucuacuuca uuucuaaag                                            29

<210> SEQ ID NO 237
<211> LENGTH: 27
<212> TYPE: RNA
<213> ORGANISM: Artificial Sequence
<220> FEATURE:
<223> OTHER INFORMATION: dsRNA

<400> SEQUENCE: 237
gcuguccuca ccaaccuguu ucuaaag                                              27

<210> SEQ ID NO 238
<211> LENGTH: 27
<212> TYPE: RNA
<213> ORGANISM: Artificial Sequence
<220> FEATURE:
<223> OTHER INFORMATION: dsRNA

<400> SEQUENCE: 238
cugcguaucc ucauugaguu ucuaaag                                              27

<210> SEQ ID NO 239
<211> LENGTH: 27
<212> TYPE: RNA
<213> ORGANISM: Artificial Sequence
<220> FEATURE:
<223> OTHER INFORMATION: dsRNA

<400> SEQUENCE: 239
gagaacagga aggugaucuu ucuaaag                                              27

<210> SEQ ID NO 240
<211> LENGTH: 27
<212> TYPE: RNA
<213> ORGANISM: Artificial Sequence
<220> FEATURE:
<223> OTHER INFORMATION: dsRNA

<400> SEQUENCE: 240
caagcugugg uccaacuuuu ucuaaag                                              27

<210> SEQ ID NO 241
<211> LENGTH: 27
<212> TYPE: RNA
<213> ORGANISM: Artificial Sequence
<220> FEATURE:
<223> OTHER INFORMATION: dsRNA

<400> SEQUENCE: 241
gaggacuacg uggagcuguu ucuaaag                                              27
```

<210> SEQ ID NO 242
<211> LENGTH: 29
<212> TYPE: RNA
<213> ORGANISM: Artificial Sequence
<220> FEATURE:
<223> OTHER INFORMATION: dsRNA

<400> SEQUENCE: 242
guguguggaa uguaccauac uuucuaaag                                29

<210> SEQ ID NO 243
<211> LENGTH: 28
<212> TYPE: RNA
<213> ORGANISM: Artificial Sequence
<220> FEATURE:
<223> OTHER INFORMATION: dsRNA

<400> SEQUENCE: 243
agagggaugu guucucgggu uucuaaag                                 28

<210> SEQ ID NO 244
<211> LENGTH: 29
<212> TYPE: RNA
<213> ORGANISM: Artificial Sequence
<220> FEATURE:
<223> OTHER INFORMATION: dsRNA

<400> SEQUENCE: 244
ccuucuguaa gagcuuucga uuucuaaag                                29

<210> SEQ ID NO 245
<211> LENGTH: 29
<212> TYPE: RNA
<213> ORGANISM: Artificial Sequence
<220> FEATURE:
<223> OTHER INFORMATION: dsRNA

<400> SEQUENCE: 245
acaagggcau cuuccuccau uuucuaaag                                29

<210> SEQ ID NO 246
<211> LENGTH: 27
<212> TYPE: RNA
<213> ORGANISM: Artificial Sequence
<220> FEATURE:
<223> OTHER INFORMATION: dsRNA

<400> SEQUENCE: 246
cugagcaauc agcaugaauu ucuaaag                                  27

<210> SEQ ID NO 247
<211> LENGTH: 27
<212> TYPE: RNA
<213> ORGANISM: Artificial Sequence
<220> FEATURE:
<223> OTHER INFORMATION: dsRNA

<400> SEQUENCE: 247
ccacuuccag auacgacauu ucuaaag                                  27

<210> SEQ ID NO 248
<211> LENGTH: 28
<212> TYPE: RNA
<213> ORGANISM: Artificial Sequence
<220> FEATURE:

```
<223> OTHER INFORMATION: dsRNA

<400> SEQUENCE: 248
accucuggca gaucuucgau uucuaaag                                              28

<210> SEQ ID NO 249
<211> LENGTH: 27
<212> TYPE: RNA
<213> ORGANISM: Artificial Sequence
<220> FEATURE:
<223> OTHER INFORMATION: dsRNA

<400> SEQUENCE: 249
cgucgacugg aaggagcauu ucuaaag                                               27

<210> SEQ ID NO 250
<211> LENGTH: 27
<212> TYPE: RNA
<213> ORGANISM: Artificial Sequence
<220> FEATURE:
<223> OTHER INFORMATION: dsRNA

<400> SEQUENCE: 250
guacauccac gagaacuauu ucuaaag                                               27

<210> SEQ ID NO 251
<211> LENGTH: 29
<212> TYPE: RNA
<213> ORGANISM: Artificial Sequence
<220> FEATURE:
<223> OTHER INFORMATION: dsRNA

<400> SEQUENCE: 251
aaggaaucgu ggagcagcca uuucuaaag                                             29

<210> SEQ ID NO 252
<211> LENGTH: 27
<212> TYPE: RNA
<213> ORGANISM: Artificial Sequence
<220> FEATURE:
<223> OTHER INFORMATION: dsRNA

<400> SEQUENCE: 252
cugcugucag aacaaauguu ucuaaag                                               27

<210> SEQ ID NO 253
<211> LENGTH: 29
<212> TYPE: RNA
<213> ORGANISM: Artificial Sequence
<220> FEATURE:
<223> OTHER INFORMATION: dsRNA

<400> SEQUENCE: 253
ugugaugagc ugguggcaga uuucuaaag                                             29

<210> SEQ ID NO 254
<211> LENGTH: 27
<212> TYPE: RNA
<213> ORGANISM: Artificial Sequence
<220> FEATURE:
<223> OTHER INFORMATION: dsRNA

<400> SEQUENCE: 254
gcaugaggau ucaaggcuuu ucuaaag                                               27
```

```
<210> SEQ ID NO 255
<211> LENGTH: 28
<212> TYPE: RNA
<213> ORGANISM: Artificial Sequence
<220> FEATURE:
<223> OTHER INFORMATION: dsRNA

<400> SEQUENCE: 255
cuggaggcua cgagaauguu uucuaaag                                          28

<210> SEQ ID NO 256
<211> LENGTH: 27
<212> TYPE: RNA
<213> ORGANISM: Artificial Sequence
<220> FEATURE:
<223> OTHER INFORMATION: dsRNA

<400> SEQUENCE: 256
uggacaucca caugaagcuu ucuaaag                                           27

<210> SEQ ID NO 257
<211> LENGTH: 29
<212> TYPE: RNA
<213> ORGANISM: Artificial Sequence
<220> FEATURE:
<223> OTHER INFORMATION: dsRNA

<400> SEQUENCE: 257
uacgaggacc aguggcugca uuucuaaag                                         29

<210> SEQ ID NO 258
<211> LENGTH: 28
<212> TYPE: RNA
<213> ORGANISM: Artificial Sequence
<220> FEATURE:
<223> OTHER INFORMATION: dsRNA

<400> SEQUENCE: 258
caugaccgag agccuguuuu uucuaaag                                          28

<210> SEQ ID NO 259
<211> LENGTH: 29
<212> TYPE: RNA
<213> ORGANISM: Artificial Sequence
<220> FEATURE:
<223> OTHER INFORMATION: dsRNA

<400> SEQUENCE: 259
gugaugaacu uugugguucg uuucuaaag                                         29

<210> SEQ ID NO 260
<211> LENGTH: 27
<212> TYPE: RNA
<213> ORGANISM: Artificial Sequence
<220> FEATURE:
<223> OTHER INFORMATION: dsRNA

<400> SEQUENCE: 260
agacgagcag ccgucucuuu ucuaaag                                           27

<210> SEQ ID NO 261
<211> LENGTH: 29
<212> TYPE: RNA
<213> ORGANISM: Artificial Sequence
<220> FEATURE:
<223> OTHER INFORMATION: dsRNA
```

```
<400> SEQUENCE: 261
gacucaucca ccuucacccu uuucuaaag                                29

<210> SEQ ID NO 262
<211> LENGTH: 29
<212> TYPE: RNA
<213> ORGANISM: Artificial Sequence
<220> FEATURE:
<223> OTHER INFORMATION: dsRNA

<400> SEQUENCE: 262
uuccugcgcu acgacugugu uuucuaaag                                29

<210> SEQ ID NO 263
<211> LENGTH: 29
<212> TYPE: RNA
<213> ORGANISM: Artificial Sequence
<220> FEATURE:
<223> OTHER INFORMATION: dsRNA

<400> SEQUENCE: 263
cacacgcuac aucauggugu uuucuaaag                                29

<210> SEQ ID NO 264
<211> LENGTH: 29
<212> TYPE: RNA
<213> ORGANISM: Artificial Sequence
<220> FEATURE:
<223> OTHER INFORMATION: dsRNA

<400> SEQUENCE: 264
ugccauugug ccuuuuuagg uuucuaaag                                29

<210> SEQ ID NO 265
<211> LENGTH: 29
<212> TYPE: RNA
<213> ORGANISM: Artificial Sequence
<220> FEATURE:
<223> OTHER INFORMATION: dsRNA

<400> SEQUENCE: 265
cacuuccuga guucauguuc uuucuaaag                                29

<210> SEQ ID NO 266
<211> LENGTH: 29
<212> TYPE: RNA
<213> ORGANISM: Artificial Sequence
<220> FEATURE:
<223> OTHER INFORMATION: dsRNA

<400> SEQUENCE: 266
ccugaacuga auaugucacc uuucuaaag                                29

<210> SEQ ID NO 267
<211> LENGTH: 30
<212> TYPE: RNA
<213> ORGANISM: Artificial Sequence
<220> FEATURE:
<223> OTHER INFORMATION: dsRNA

<400> SEQUENCE: 267
cgcagucuca cucugaauaa auuucuaaag                               30

<210> SEQ ID NO 268
<211> LENGTH: 28
```

-continued

```
<212> TYPE: RNA
<213> ORGANISM: Artificial Sequence
<220> FEATURE:
<223> OTHER INFORMATION: dsRNA

<400> SEQUENCE: 268
ggacaguuug uaagucuugu uucuaaag                                          28

<210> SEQ ID NO 269
<211> LENGTH: 29
<212> TYPE: RNA
<213> ORGANISM: Artificial Sequence
<220> FEATURE:
<223> OTHER INFORMATION: dsRNA

<400> SEQUENCE: 269
ucacuucccc uguccagguu uuucuaaag                                         29

<210> SEQ ID NO 270
<211> LENGTH: 29
<212> TYPE: RNA
<213> ORGANISM: Artificial Sequence
<220> FEATURE:
<223> OTHER INFORMATION: dsRNA

<400> SEQUENCE: 270
ucagcuucca caugugucaa uuucuaaag                                         29

<210> SEQ ID NO 271
<211> LENGTH: 28
<212> TYPE: RNA
<213> ORGANISM: Artificial Sequence
<220> FEATURE:
<223> OTHER INFORMATION: dsRNA

<400> SEQUENCE: 271
gacaauccuc gccuugucuu uucuaaag                                          28

<210> SEQ ID NO 272
<211> LENGTH: 28
<212> TYPE: RNA
<213> ORGANISM: Artificial Sequence
<220> FEATURE:
<223> OTHER INFORMATION: dsRNA

<400> SEQUENCE: 272
gcaucuggag cuuucuguau uucuaaag                                          28

<210> SEQ ID NO 273
<211> LENGTH: 27
<212> TYPE: RNA
<213> ORGANISM: Artificial Sequence
<220> FEATURE:
<223> OTHER INFORMATION: dsRNA

<400> SEQUENCE: 273
gagaucccag gauccugguu ucuaaag                                           27

<210> SEQ ID NO 274
<211> LENGTH: 29
<212> TYPE: RNA
<213> ORGANISM: Artificial Sequence
<220> FEATURE:
<223> OTHER INFORMATION: dsRNA

<400> SEQUENCE: 274
```
aaucaggaug ccacugugua uuucuaaag                              29

<210> SEQ ID NO 275
<211> LENGTH: 29
<212> TYPE: RNA
<213> ORGANISM: Artificial Sequence
<220> FEATURE:
<223> OTHER INFORMATION: dsRNA

<400> SEQUENCE: 275
cuggaugaga agguuaguga uuucuaaag                              29

<210> SEQ ID NO 276
<211> LENGTH: 29
<212> TYPE: RNA
<213> ORGANISM: Artificial Sequence
<220> FEATURE:
<223> OTHER INFORMATION: dsRNA

<400> SEQUENCE: 276
ugugggaacu guuucuccag uuucuaaag                              29

<210> SEQ ID NO 277
<211> LENGTH: 27
<212> TYPE: RNA
<213> ORGANISM: Artificial Sequence
<220> FEATURE:
<223> OTHER INFORMATION: dsRNA

<400> SEQUENCE: 277
cuggaccagu agucaacauu ucuaaag                                27

<210> SEQ ID NO 278
<211> LENGTH: 28
<212> TYPE: RNA
<213> ORGANISM: Artificial Sequence
<220> FEATURE:
<223> OTHER INFORMATION: dsRNA

<400> SEQUENCE: 278
ccaaaggaua gagucacugu uucuaaag                               28

<210> SEQ ID NO 279
<211> LENGTH: 30
<212> TYPE: RNA
<213> ORGANISM: Artificial Sequence
<220> FEATURE:
<223> OTHER INFORMATION: dsRNA

<400> SEQUENCE: 279
cagcaccaag gcuauggcuu uuuucuaaag                             30

<210> SEQ ID NO 280
<211> LENGTH: 29
<212> TYPE: RNA
<213> ORGANISM: Artificial Sequence
<220> FEATURE:
<223> OTHER INFORMATION: dsRNA

<400> SEQUENCE: 280
guggaauucu ugagugagga uuucuaaag                              29

<210> SEQ ID NO 281
<211> LENGTH: 29
<212> TYPE: RNA
<213> ORGANISM: Artificial Sequence

```
<220> FEATURE:
<223> OTHER INFORMATION: dsRNA

<400> SEQUENCE: 281
gcugacuaug ccauuaagau uuucuaaag                                    29

<210> SEQ ID NO 282
<211> LENGTH: 28
<212> TYPE: RNA
<213> ORGANISM: Artificial Sequence
<220> FEATURE:
<223> OTHER INFORMATION: dsRNA

<400> SEQUENCE: 282
acaugaucaa acucuauggu uucuaaag                                     28

<210> SEQ ID NO 283
<211> LENGTH: 27
<212> TYPE: RNA
<213> ORGANISM: Artificial Sequence
<220> FEATURE:
<223> OTHER INFORMATION: dsRNA

<400> SEQUENCE: 283
ggugaacaaa gcaucagcuu ucuaaag                                      27

<210> SEQ ID NO 284
<211> LENGTH: 27
<212> TYPE: RNA
<213> ORGANISM: Artificial Sequence
<220> FEATURE:
<223> OTHER INFORMATION: dsRNA

<400> SEQUENCE: 284
ccugagauug augagaaguu ucuaaag                                      27

<210> SEQ ID NO 285
<211> LENGTH: 26
<212> TYPE: RNA
<213> ORGANISM: Artificial Sequence
<220> FEATURE:
<223> OTHER INFORMATION: dsRNA

<400> SEQUENCE: 285
ggucaucuua caaacccuuu cuaaag                                       26

<210> SEQ ID NO 286
<211> LENGTH: 27
<212> TYPE: RNA
<213> ORGANISM: Artificial Sequence
<220> FEATURE:
<223> OTHER INFORMATION: dsRNA

<400> SEQUENCE: 286
ccugacacag gcaacuccuu ucuaaag                                      27

<210> SEQ ID NO 287
<211> LENGTH: 29
<212> TYPE: RNA
<213> ORGANISM: Artificial Sequence
<220> FEATURE:
<223> OTHER INFORMATION: dsRNA

<400> SEQUENCE: 287
gcuucauuug augcuucgga uuucuaaag                                    29
```

```
<210> SEQ ID NO 288
<211> LENGTH: 29
<212> TYPE: RNA
<213> ORGANISM: Artificial Sequence
<220> FEATURE:
<223> OTHER INFORMATION: dsRNA

<400> SEQUENCE: 288
ugcagcaauu gaagccauga uuucuaaag                                   29

<210> SEQ ID NO 289
<211> LENGTH: 28
<212> TYPE: RNA
<213> ORGANISM: Artificial Sequence
<220> FEATURE:
<223> OTHER INFORMATION: dsRNA

<400> SEQUENCE: 289
gcaguaccuc uguaaccguu uucuaaag                                    28

<210> SEQ ID NO 290
<211> LENGTH: 29
<212> TYPE: RNA
<213> ORGANISM: Artificial Sequence
<220> FEATURE:
<223> OTHER INFORMATION: dsRNA

<400> SEQUENCE: 290
caccguaucu uaugccuuca uuucuaaag                                   29

<210> SEQ ID NO 291
<211> LENGTH: 29
<212> TYPE: RNA
<213> ORGANISM: Artificial Sequence
<220> FEATURE:
<223> OTHER INFORMATION: dsRNA

<400> SEQUENCE: 291
gaacgacuuc uggcagcuca uuucuaaag                                   29

<210> SEQ ID NO 292
<211> LENGTH: 29
<212> TYPE: RNA
<213> ORGANISM: Artificial Sequence
<220> FEATURE:
<223> OTHER INFORMATION: dsRNA

<400> SEQUENCE: 292
ccucaucagc uguuugcaga uuucuaaag                                   29

<210> SEQ ID NO 293
<211> LENGTH: 29
<212> TYPE: RNA
<213> ORGANISM: Artificial Sequence
<220> FEATURE:
<223> OTHER INFORMATION: dsRNA

<400> SEQUENCE: 293
uggucaugga cacucacauc uuucuaaag                                   29

<210> SEQ ID NO 294
<211> LENGTH: 27
<212> TYPE: RNA
<213> ORGANISM: Artificial Sequence
<220> FEATURE:
<223> OTHER INFORMATION: dsRNA
```

```
<400> SEQUENCE: 294
gaugucucag augcagcuuu ucuaaag                                27

<210> SEQ ID NO 295
<211> LENGTH: 27
<212> TYPE: RNA
<213> ORGANISM: Artificial Sequence
<220> FEATURE:
<223> OTHER INFORMATION: dsRNA

<400> SEQUENCE: 295
ccucauggcu uaggacauuu ucuaaag                                27

<210> SEQ ID NO 296
<211> LENGTH: 29
<212> TYPE: RNA
<213> ORGANISM: Artificial Sequence
<220> FEATURE:
<223> OTHER INFORMATION: dsRNA

<400> SEQUENCE: 296
ucacauuuuc cuuccuccug uuucuaaag                              29

<210> SEQ ID NO 297
<211> LENGTH: 29
<212> TYPE: RNA
<213> ORGANISM: Artificial Sequence
<220> FEATURE:
<223> OTHER INFORMATION: dsRNA

<400> SEQUENCE: 297
ccuuggacca aucagagaug uuucuaaag                              29

<210> SEQ ID NO 298
<211> LENGTH: 29
<212> TYPE: RNA
<213> ORGANISM: Artificial Sequence
<220> FEATURE:
<223> OTHER INFORMATION: dsRNA

<400> SEQUENCE: 298
ggcaaaggua cuaaucccuu uuucuaaag                              29

<210> SEQ ID NO 299
<211> LENGTH: 27
<212> TYPE: RNA
<213> ORGANISM: Artificial Sequence
<220> FEATURE:
<223> OTHER INFORMATION: dsRNA

<400> SEQUENCE: 299
uuccacagga gguauuucuu ucuaaag                                27

<210> SEQ ID NO 300
<211> LENGTH: 27
<212> TYPE: RNA
<213> ORGANISM: Artificial Sequence
<220> FEATURE:
<223> OTHER INFORMATION: dsRNA

<400> SEQUENCE: 300
gguccugagu auuuugcauu ucuaaag                                27

<210> SEQ ID NO 301
```

```
<210> SEQ ID NO 301
<211> LENGTH: 28
<212> TYPE: RNA
<213> ORGANISM: Artificial Sequence
<220> FEATURE:
<223> OTHER INFORMATION: dsRNA

<400> SEQUENCE: 301
ccaaaucugc aagaaggcuu uucuaaag                                    28

<210> SEQ ID NO 302
<211> LENGTH: 30
<212> TYPE: RNA
<213> ORGANISM: Artificial Sequence
<220> FEATURE:
<223> OTHER INFORMATION: dsRNA

<400> SEQUENCE: 302
ggaacucuuc agcacauccu uuucuaaag                                   30

<210> SEQ ID NO 303
<211> LENGTH: 29
<212> TYPE: RNA
<213> ORGANISM: Artificial Sequence
<220> FEATURE:
<223> OTHER INFORMATION: dsRNA

<400> SEQUENCE: 303
cucuggacaa cagaagaaga uuucuaaag                                   29

<210> SEQ ID NO 304
<211> LENGTH: 27
<212> TYPE: RNA
<213> ORGANISM: Artificial Sequence
<220> FEATURE:
<223> OTHER INFORMATION: dsRNA

<400> SEQUENCE: 304
ugagagcagu gugauucuuu ucuaaag                                     27

<210> SEQ ID NO 305
<211> LENGTH: 26
<212> TYPE: RNA
<213> ORGANISM: Artificial Sequence
<220> FEATURE:
<223> OTHER INFORMATION: dsRNA

<400> SEQUENCE: 305 caagcuagc agugcauuuu cuaaag                                       26

<210> SEQ ID NO 306
<211> LENGTH: 28
<212> TYPE: RNA
<213> ORGANISM: Artificial Sequence
<220> FEATURE:
<223> OTHER INFORMATION: dsRNA

<400> SEQUENCE: 306
cucgcuaaga caacuagcau uucuaaag                                    28

<210> SEQ ID NO 307
<211> LENGTH: 29
<212> TYPE: RNA
<213> ORGANISM: Artificial Sequence
<220> FEATURE:
<223> OTHER INFORMATION: dsRNA

<400> SEQUENCE: 307
```
cagguuaagu uucggaggcu uuucuaaag                                29

<210> SEQ ID NO 308
<211> LENGTH: 29
<212> TYPE: RNA
<213> ORGANISM: Artificial Sequence
<220> FEATURE:
<223> OTHER INFORMATION: dsRNA

<400> SEQUENCE: 308
gcuuccaggc accuccucuu uuucuaaag                                29

<210> SEQ ID NO 309
<211> LENGTH: 29
<212> TYPE: RNA
<213> ORGANISM: Artificial Sequence
<220> FEATURE:
<223> OTHER INFORMATION: dsRNA

<400> SEQUENCE: 309
gaaguggaag ucgugcugag uuucuaaag                                29

<210> SEQ ID NO 310
<211> LENGTH: 29
<212> TYPE: RNA
<213> ORGANISM: Artificial Sequence
<220> FEATURE:
<223> OTHER INFORMATION: dsRNA

<400> SEQUENCE: 310
gaucucuuuc gccauggcug uuucuaaag                                29

<210> SEQ ID NO 311
<211> LENGTH: 21
<212> TYPE: RNA
<213> ORGANISM: Artificial Sequence
<220> FEATURE:
<223> OTHER INFORMATION: Mouse siRNA sense strand

<400> SEQUENCE: 311
ccucagcguu ucaaucuuuu u                                        21

<210> SEQ ID NO 312
<211> LENGTH: 21
<212> TYPE: RNA
<213> ORGANISM: Artificial Sequence
<220> FEATURE:
<223> OTHER INFORMATION: Mouse siRNA sense strand

<400> SEQUENCE: 312
cgacugcaga aucuccucuu u                                        21

<210> SEQ ID NO 313
<211> LENGTH: 21
<212> TYPE: RNA
<213> ORGANISM: Artificial Sequence
<220> FEATURE:
<223> OTHER INFORMATION: Mouse siRNA sense strand

<400> SEQUENCE: 313
cugcuuuacg auacuuucau u                                        21

<210> SEQ ID NO 314
<211> LENGTH: 19
<212> TYPE: RNA

```
<213> ORGANISM: Artificial Sequence
<220> FEATURE:
<223> OTHER INFORMATION: Control siRNA sense strand

<400> SEQUENCE: 314
ccuacgccac caauuucgu                                                        19

<210> SEQ ID NO 315
<211> LENGTH: 19
<212> TYPE: RNA
<213> ORGANISM: Artificial Sequence
<220> FEATURE:
<223> OTHER INFORMATION: Control siRNA antisense strand

<400> SEQUENCE: 315
acgaaauugg uggcguagg                                                        19

<210> SEQ ID NO 316
<211> LENGTH: 20
<212> TYPE: DNA
<213> ORGANISM: Artificial Sequence
<220> FEATURE:
<223> OTHER INFORMATION: Human BANF1 primer forward strand

<400> SEQUENCE: 316
gaaccgttac gggaactgaa                                                       20

<210> SEQ ID NO 317
<211> LENGTH: 20
<212> TYPE: DNA
<213> ORGANISM: Artificial Sequence
<220> FEATURE:
<223> OTHER INFORMATION: Human BANF1 primer reverse strand

<400> SEQUENCE: 317
cccggaagag gtcttcatct                                                       20

<210> SEQ ID NO 318
<211> LENGTH: 20
<212> TYPE: DNA
<213> ORGANISM: Artificial Sequence
<220> FEATURE:
<223> OTHER INFORMATION: Human PLOD3 primer forward strand

<400> SEQUENCE: 318
cagctccagg accacttctc                                                       20

<210> SEQ ID NO 319
<211> LENGTH: 20
<212> TYPE: DNA
<213> ORGANISM: Artificial Sequence
<220> FEATURE:
<223> OTHER INFORMATION: Human PLOD3 primer reverse strand

<400> SEQUENCE: 319
gagcgggcgt agtactcatc                                                       20

<210> SEQ ID NO 320
<211> LENGTH: 20
<212> TYPE: DNA
<213> ORGANISM: Artificial Sequence
<220> FEATURE:
<223> OTHER INFORMATION: Human SF3B4 primer forward strand

<400> SEQUENCE: 320
ctcagatgca gcttgcacac                                                       20
```

<210> SEQ ID NO 321
<211> LENGTH: 19
<212> TYPE: DNA
<213> ORGANISM: Artificial Sequence
<220> FEATURE:
<223> OTHER INFORMATION: Human SF3B4 primer reverse strand

<400> SEQUENCE: 321
ggagggccag tgtatccat                                            19

<210> SEQ ID NO 322
<211> LENGTH: 20
<212> TYPE: DNA
<213> ORGANISM: Artificial Sequence
<220> FEATURE:
<223> OTHER INFORMATION: Human GAPDH primer forward strand

<400> SEQUENCE: 322
accaggtggt ctcctctgac                                           20

<210> SEQ ID NO 323
<211> LENGTH: 20
<212> TYPE: DNA
<213> ORGANISM: Artificial Sequence
<220> FEATURE:
<223> OTHER INFORMATION: Human GAPDH primer reverse strand

<400> SEQUENCE: 323
tgctgtagcc aaattcgttg                                           20

<210> SEQ ID NO 324
<211> LENGTH: 21
<212> TYPE: RNA
<213> ORGANISM: Artificial Sequence
<220> FEATURE:
<223> OTHER INFORMATION: GFP siRNA sense strand

<400> SEQUENCE: 324
ggcuacgucc aggagcgcac c                                         21

<210> SEQ ID NO 325
<211> LENGTH: 21
<212> TYPE: RNA
<213> ORGANISM: Artificial Sequence
<220> FEATURE:
<223> OTHER INFORMATION: GFP siRNA antisense strand

<400> SEQUENCE: 325
ugcgcuccug gacguagccu u                                         21

<210> SEQ ID NO 326
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 326 cuuccucca gcuucuuguu                                            20

<210> SEQ ID NO 327
<211> LENGTH: 21
<212> TYPE: RNA
<213> ORGANISM: Artificial Sequence
<220> FEATURE:

```
<223> OTHER INFORMATION: siRNA antisense strand

<400> SEQUENCE: 327
ggaagagguc uucaucuucu u                                              21

<210> SEQ ID NO 328
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 328
aagugucuuu cagccauucc uu                                             22

<210> SEQ ID NO 329
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 329
gggaacuggg aacacugguu                                                20

<210> SEQ ID NO 330
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 330
uccucgcagu uggacugguu                                                20

<210> SEQ ID NO 331
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 331
agacucagac ucacgucguu                                                20

<210> SEQ ID NO 332
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 332
aagaguuaga agacggacuu                                                20

<210> SEQ ID NO 333
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 333
aaggacuuag gcuugacguu                                                20
```

```
<210> SEQ ID NO 334
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 334
aggacuuccu uucucugcuu                                               20

<210> SEQ ID NO 335
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 335
cuaaggucuc gcuucucguu                                               20

<210> SEQ ID NO 336
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 336
agagcuauag aguugagguu                                               20

<210> SEQ ID NO 337
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 337
gauaccucaa gccacuaguu                                               20

<210> SEQ ID NO 338
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 338
cuugaucagg cuuaauccuu                                               20

<210> SEQ ID NO 339
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 339
aaggcauccg aagcagucuu                                               20

<210> SEQ ID NO 340
<211> LENGTH: 20
<212> TYPE: RNA
<213> ORGANISM: Artificial Sequence
<220> FEATURE:
<223> OTHER INFORMATION: siRNA antisense strand
```

<400> SEQUENCE: 340
gagagcauca caagaagguu                                               20

<210> SEQ ID NO 341
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 341
ugcaaacucu ggaugagguu                                               20

<210> SEQ ID NO 342
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 342
uccuucguag aggacagguu                                               20

<210> SEQ ID NO 343
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 343
ugaguacgac aauagcaauc uu                                            22

<210> SEQ ID NO 344
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 344
augcaagagc gagaauccuu                                               20

<210> SEQ ID NO 345
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 345
aagcugguaa cugucaccuu                                               20

<210> SEQ ID NO 346
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 346
aacggauuga aagugagguu                                               20

<210> SEQ ID NO 347
<211> LENGTH: 20

```
<212> TYPE: RNA
<213> ORGANISM: Artificial Sequence
<220> FEATURE:
<223> OTHER INFORMATION: siRNA antisense strand

<400> SEQUENCE: 347
ggacagugac uguucugcuu                                                    20

<210> SEQ ID NO 348
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 348
agccacugac uuuauugauc uu                                                 22

<210> SEQ ID NO 349
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 349
ccccuuuccu ccgcuucuuu u                                                  21

<210> SEQ ID NO 350
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 350
ugcuuuuggg agguugucau uu                                                 22

<210> SEQ ID NO 351
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 351
ucugccacga agucucgguu                                                    20

<210> SEQ ID NO 352
<211> LENGTH: 17
<212> TYPE: RNA
<213> ORGANISM: Artificial Sequence
<220> FEATURE:
<223> OTHER INFORMATION: siRNA antisense strand

<400> SEQUENCE: 352
aaucccagcc aggcuuu                                                       17

<210> SEQ ID NO 353
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 353
``` uuccuccag cuucuuguu                19

<210> SEQ ID NO 354
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 354
ucuuuagcac cagaaacugg uu          22

<210> SEQ ID NO 355
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 355
ggaagagguc uucaucuuuu             20

<210> SEQ ID NO 356
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 356
aaggcauccg aagcaguccu u           21

<210> SEQ ID NO 357
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 357
aagaaggcgu cgcaccacuu u           21

<210> SEQ ID NO 358
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 358
aagaaggcgu cgcaccacuu u           21

<210> SEQ ID NO 359
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 359
ggugaguacg acaauagcaa uu          22

<210> SEQ ID NO 360
<211> LENGTH: 20
<212> TYPE: RNA
<213> ORGANISM: Artificial Sequence

```
<220> FEATURE:
<223> OTHER INFORMATION: siRNA antisense strand

<400> SEQUENCE: 360
caugcaagag cgagaaucuu                                                   20

<210> SEQ ID NO 361
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 361
uaacugucac cagggaacug uu                                                22

<210> SEQ ID NO 362
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 362
uccauucagg aaagcugguu                                                   20

<210> SEQ ID NO 363
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 363
ucaaacggau ugaaagugag uu                                                22

<210> SEQ ID NO 364
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 364
caaggacagu gacuguucug uu                                                22

<210> SEQ ID NO 365
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 365
cucgcaguug gacugguguu                                                   20

<210> SEQ ID NO 366
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 366
agacucagac ucacgucgca uu                                                22
```

```
<210> SEQ ID NO 367
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 367
aaguacgguu uucggagguu                                                   20

<210> SEQ ID NO 368
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 368
gaguuagaag acggacaagg uu                                                22

<210> SEQ ID NO 369
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 369
uuaggcuuga cggaccuggu u                                                 21

<210> SEQ ID NO 370
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 370
uacuuccuuu cucugcugcu u                                                 21

<210> SEQ ID NO 371
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 371
aguucugagg gagauagguu                                                   20

<210> SEQ ID NO 372
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 372
cuucuaaggu cucgcuucuc uu                                                22

<210> SEQ ID NO 373
<211> LENGTH: 22
<212> TYPE: RNA
<213> ORGANISM: Artificial Sequence
<220> FEATURE:
<223> OTHER INFORMATION: siRNA antisense strand
```

```
<400> SEQUENCE: 373
uagagcuaua gaguugaggc uu                                          22

<210> SEQ ID NO 374
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 374
agaaacauuc cacguugguu                                             20

<210> SEQ ID NO 375
<211> LENGTH: 24
<212> TYPE: RNA
<213> ORGANISM: Artificial Sequence
<220> FEATURE:
<223> OTHER INFORMATION: siRNA antisense strand

<400> SEQUENCE: 375
aacuuucuuc cacuuccgcu ucuu                                        24

<210> SEQ ID NO 376
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 376
gcuuaaucuc aagccacuag uu                                          22

<210> SEQ ID NO 377
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 377
aucaccagca gcuucucugg uu                                          22

<210> SEQ ID NO 378
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 378
ccucgguuuc agcugugguu                                             20

<210> SEQ ID NO 379
<211> LENGTH: 18
<212> TYPE: RNA
<213> ORGANISM: Artificial Sequence
<220> FEATURE:
<223> OTHER INFORMATION: siRNA antisense strand

<400> SEQUENCE: 379
gaagaacucc gcagaguu                                               18

<210> SEQ ID NO 380
```

```
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 380
gguccgcaca guguaguuuu                                                      20

<210> SEQ ID NO 381
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 381
cuguucgagc cacaucacuu                                                      20

<210> SEQ ID NO 382
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 382
cuccauuucc uucuuuaacc uu                                                   22

<210> SEQ ID NO 383
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 383
acaugaugau cauauccucc uu                                                   22

<210> SEQ ID NO 384
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 384
aucacgucgu agcuauccuu                                                      20

<210> SEQ ID NO 385
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 385
uucuucagca gcucuguguu                                                      20

<210> SEQ ID NO 386
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 386
```
ucucugcaga gaagagcauu                                                20

<210> SEQ ID NO 387
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 387
ccaccagaau ugaggaagcu u                                              21

<210> SEQ ID NO 388
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 388
ugguggcaaa accgaugaau uu                                             22

<210> SEQ ID NO 389
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 389
ucauccuugu acuuccacuu u                                              21

<210> SEQ ID NO 390
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 390
ugauccagau uaaggcuguu                                                20

<210> SEQ ID NO 391
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 391
gguucugaaa gauccgagac uu                                             22

<210> SEQ ID NO 392
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 392
accacuucau cuaaagccuu                                                20

<210> SEQ ID NO 393
<211> LENGTH: 20
<212> TYPE: RNA

```
<213> ORGANISM: Artificial Sequence
<220> FEATURE:
<223> OTHER INFORMATION: siRNA antisense strand

<400> SEQUENCE: 393
acacgguucc gaucaaacuu                                              20

<210> SEQ ID NO 394
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 394 cguuccaug gaccacaauu                                               20

<210> SEQ ID NO 395
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 395
uugagcugca gcuuaguggu u                                            21

<210> SEQ ID NO 396
<211> LENGTH: 21
<212> TYPE: DNA
<213> ORGANISM: Artificial Sequence
<220> FEATURE:
<223> OTHER INFORMATION: siRNA antisense strand

<400> SEQUENCE: 396
tcaggagtcc agccattggu u                                            21

<210> SEQ ID NO 397
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 397
ugguugcaga agccacagcu u                                            21

<210> SEQ ID NO 398
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 398
aggcuguucc acaaacacuu                                              20

<210> SEQ ID NO 399
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 399
auaguccagg aguagcagcu u                                            21
```

<210> SEQ ID NO 400
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 400
accucguugu ugugcaggaa uu                                              22

<210> SEQ ID NO 401
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 401
caggagucag cgaugugguu                                                 20

<210> SEQ ID NO 402
<211> LENGTH: 22
<212> TYPE: DNA
<213> ORGANISM: Artificial Sequence
<220> FEATURE:
<223> OTHER INFORMATION: siRNA antisense strand

<400> SEQUENCE: 402
tgagaagtgg tcctggagct uu                                              22

<210> SEQ ID NO 403
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 403
acacaggucc auggccauuu                                                 20

<210> SEQ ID NO 404
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 404
ugaaguagaa cucacacucg uu                                              22

<210> SEQ ID NO 405
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 405
cagguuggug aggacagcuu                                                 20

<210> SEQ ID NO 406
<211> LENGTH: 20
<212> TYPE: RNA
<213> ORGANISM: Artificial Sequence
<220> FEATURE:

<223> OTHER INFORMATION: siRNA antisense strand

<400> SEQUENCE: 406
cucaaugagg auacgcaguu                                              20

<210> SEQ ID NO 407
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 407
gaucaccuuc cguucucuu                                               20

<210> SEQ ID NO 408
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 408
aaguuggacc acagcuuguu                                              20

<210> SEQ ID NO 409
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 409
cagcuccacg uaguccucuu                                              20

<210> SEQ ID NO 410
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 410
guaugguaca uuccacacac uu                                           22

<210> SEQ ID NO 411
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 411
cccgagaaca caucccucuu u                                            21

<210> SEQ ID NO 412
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 412
ucgaaagcuc uuacagaagg uu                                           22

<210> SEQ ID NO 413
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 413
auggaggaag augcccuugu uu                                            22

<210> SEQ ID NO 414
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 414
uucaugcuga uugcucaguu                                               20

<210> SEQ ID NO 415
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 415
ugucguaucu ggaagugguu                                               20

<210> SEQ ID NO 416
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 416
ucgaagaucu gccagagguu u                                             21

<210> SEQ ID NO 417
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 417
ugcuccuucc agucgacguu                                               20

<210> SEQ ID NO 418
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 418
uaguucucgu ggauguacuu                                               20

<210> SEQ ID NO 419
<211> LENGTH: 22
<212> TYPE: RNA
<213> ORGANISM: Artificial Sequence
<220> FEATURE:
<223> OTHER INFORMATION: siRNA antisense strand

```
<400> SEQUENCE: 419
uggcugcucc acgauuccuu uu                                              22

<210> SEQ ID NO 420
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 420
cauuuguucu gacagcaguu                                                 20

<210> SEQ ID NO 421
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 421
ucugccacca gcucaucaca uu                                              22

<210> SEQ ID NO 422
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 422
agccuugaau ccucaugcuu                                                 20

<210> SEQ ID NO 423
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 423
acauucucgu agccuccagu u                                               21

<210> SEQ ID NO 424
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 424
gcuucaugug gauguccauu                                                 20

<210> SEQ ID NO 425
<211> LENGTH: 22
<212> TYPE: DNA
<213> ORGANISM: Artificial Sequence
<220> FEATURE:
<223> OTHER INFORMATION: siRNA antisense strand

<400> SEQUENCE: 425
tgcagccact ggtcctcgta uu                                              22

<210> SEQ ID NO 426
<211> LENGTH: 21
```

```
<212> TYPE: RNA
<213> ORGANISM: Artificial Sequence
<220> FEATURE:
<223> OTHER INFORMATION: siRNA antisense strand

<400> SEQUENCE: 426
aaacaggcuc ucggucaugu u                                      21

<210> SEQ ID NO 427
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 427
cgaaccacaa aguucaucac uu                                     22

<210> SEQ ID NO 428
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 428
agagacggcu gcucgucuuu                                        20

<210> SEQ ID NO 429
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 429
agggugaagg uggaugaguc uu                                     22

<210> SEQ ID NO 430
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 430
acacagucgu agcgcaggaa uu                                     22

<210> SEQ ID NO 431
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 431
acaccaugau guagcgugug uu                                     22

<210> SEQ ID NO 432
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 432
```
ccuaaaaagg cacaauggca uu                                                22

<210> SEQ ID NO 433
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 433
gaacaugaac ucaggaagug uu                                                22

<210> SEQ ID NO 434
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 434
ggugacauau ucaguucagg uu                                                22

<210> SEQ ID NO 435
<211> LENGTH: 23
<212> TYPE: RNA
<213> ORGANISM: Artificial Sequence
<220> FEATURE:
<223> OTHER INFORMATION: siRNA antisense strand

<400> SEQUENCE: 435
uuuauucaga gugagacugc guu                                               23

<210> SEQ ID NO 436
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 436
caagacuuac aaacuguccu u                                                 21

<210> SEQ ID NO 437
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 437
aaccuggaca ggggaaguga uu                                                22

<210> SEQ ID NO 438
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 438
uugacacaug uggaagcuga uu                                                22

<210> SEQ ID NO 439
<211> LENGTH: 21
<212> TYPE: RNA
<213> ORGANISM: Artificial Sequence

```
<220> FEATURE:
<223> OTHER INFORMATION: siRNA antisense strand

<400> SEQUENCE: 439
agacaaggcg aggauugucu u                                              21

<210> SEQ ID NO 440
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 440
uacagaaagc uccagaugcu u                                              21

<210> SEQ ID NO 441
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 441
ccaggauccu gggaucucuu                                                20

<210> SEQ ID NO 442
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 442
uacacagugg cauccugauu uu                                             22

<210> SEQ ID NO 443
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 443
ucacuaaccu ucucauccag uu                                             22

<210> SEQ ID NO 444
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 444
cuggagaaac aguucccaca uu                                             22

<210> SEQ ID NO 445
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 445
uguugacuac ugguccaguu                                                20
```

```
<210> SEQ ID NO 446
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 446
cagugacucu auccuuuggu u                                              21

<210> SEQ ID NO 447
<211> LENGTH: 23
<212> TYPE: RNA
<213> ORGANISM: Artificial Sequence
<220> FEATURE:
<223> OTHER INFORMATION: siRNA antisense strand

<400> SEQUENCE: 447
aaagccauag ccuuggugcu guu                                            23

<210> SEQ ID NO 448
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 448
uccucacuca agaauuccac uu                                             22

<210> SEQ ID NO 449
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 449
aucuuaaugg cauagucagc uu                                             22

<210> SEQ ID NO 450
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 450
ccauagaguu ugaucauguu u                                              21

<210> SEQ ID NO 451
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 451
gcugaugcuu uguucaccuu                                                20

<210> SEQ ID NO 452
<211> LENGTH: 20
<212> TYPE: RNA
<213> ORGANISM: Artificial Sequence
<220> FEATURE:
<223> OTHER INFORMATION: siRNA antisense strand
```

<400> SEQUENCE: 452
cuucucauca aucucagguu                                              20

<210> SEQ ID NO 453
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 453
ggguuuguaa gaugaccuu                                               19

<210> SEQ ID NO 454
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 454
ggaguugccu gugucagguu                                              20

<210> SEQ ID NO 455
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 455
uccgaagcau caaaugaagc uu                                           22

<210> SEQ ID NO 456
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 456
ucauggcuuc aauugcugca uu                                           22

<210> SEQ ID NO 457
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 457
acgguuacag agguacugcu u                                            21

<210> SEQ ID NO 458
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 458
ugaaggcaua agauacggug uu                                           22

<210> SEQ ID NO 459

```
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 459
ugagcugcca gaagucguuc uu                                                  22

<210> SEQ ID NO 460
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 460
ucugcaaaca gcugaugagg uu                                                  22

<210> SEQ ID NO 461
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 461
gaugugagug uccaugacca uu                                                  22

<210> SEQ ID NO 462
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 462
agcugcaucu gagacaucuu                                                     20

<210> SEQ ID NO 463
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 463
auguccuaag ccaugagguu                                                     20

<210> SEQ ID NO 464
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 464
caggaggaag gaaaauguga uu                                                  22

<210> SEQ ID NO 465
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 465
```
caucucugau ugguccaagg uu                                        22

<210> SEQ ID NO 466
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 466
aagggauuag uaccuuugcc uu                                        22

<210> SEQ ID NO 467
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 467
gaaauaccuc cuguggaauu                                           20

<210> SEQ ID NO 468
<211> LENGTH: 20
<212> TYPE: RNA
<213> ORGANISM: Artificial Sequence
<220> FEATURE:
<223> OTHER INFORMATION: siRNA antisense strand

<400> SEQUENCE: 468
ugcaaaauac ucaggaccuu                                           20

<210> SEQ ID NO 469
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 469
agccuucuug cagauuuggu u                                         21

<210> SEQ ID NO 470
<211> LENGTH: 23
<212> TYPE: RNA
<213> ORGANISM: Artificial Sequence
<220> FEATURE:
<223> OTHER INFORMATION: siRNA antisense strand

<400> SEQUENCE: 470
aaggaugugc ugaagaguuc cuu                                       23

<210> SEQ ID NO 471
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 471
ucuucuucug uuguccagag uu                                        22

<210> SEQ ID NO 472
<211> LENGTH: 20
<212> TYPE: RNA

```
<213> ORGANISM: Artificial Sequence
<220> FEATURE:
<223> OTHER INFORMATION: siRNA antisense strand

<400> SEQUENCE: 472
agaaucacac ugcucucauu                                               20

<210> SEQ ID NO 473
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 473
augcacugcu agacuuguu                                                19

<210> SEQ ID NO 474
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 474
ugcuaguugu cuuagcgaga uu                                            22

<210> SEQ ID NO 475
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 475
agccuccgaa acuuaaccug uu                                            22

<210> SEQ ID NO 476
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 476
aagaggaggu gccuggaagc uu                                            22

<210> SEQ ID NO 477
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 477
cucagcacga cuuccacuuc uu                                            22

<210> SEQ ID NO 478
<211> LENGTH: 22
<212> TYPE: RNA
<213> ORGANISM: Artificial Sequence
<220> FEATURE:
<223> OTHER INFORMATION: siRNA antisense strand

<400> SEQUENCE: 478
cagccauggc gaaagagauc uu                                            22
```

<210> SEQ ID NO 479
<211> LENGTH: 19
<212> TYPE: RNA
<213> ORGANISM: Artificial Sequence
<220> FEATURE:
<223> OTHER INFORMATION: Mouse siRNA antisense strand

<400> SEQUENCE: 479
aaagauugaa acgcugagg                                                19

<210> SEQ ID NO 480
<211> LENGTH: 19
<212> TYPE: RNA
<213> ORGANISM: Artificial Sequence
<220> FEATURE:
<223> OTHER INFORMATION: Mouse siRNA antisense strand

<400> SEQUENCE: 480
agaggagauu cugcagucg                                                19

<210> SEQ ID NO 481
<211> LENGTH: 19
<212> TYPE: RNA
<213> ORGANISM: Artificial Sequence
<220> FEATURE:
<223> OTHER INFORMATION: Mouse siRNA antisense strand

<400> SEQUENCE: 481
ugaaaguauc guaaagcag                                                19

<210> SEQ ID NO 482
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 482
caagaagctg gaggaaag                                                 18

<210> SEQ ID NO 483
<211> LENGTH: 20
<212> TYPE: DNA
<213> ORGANISM: Artificial Sequence
<220> FEATURE:
<223> OTHER INFORMATION: Human BANF1 gene variant1

<400> SEQUENCE: 483
gaaagatgaa gacctcttcc                                               20

<210> SEQ ID NO 484
<211> LENGTH: 20
<212> TYPE: DNA
<213> ORGANISM: Artificial Sequence
<220> FEATURE:
<223> OTHER INFORMATION: Human BANF1 gene variant1

<400> SEQUENCE: 484
ggaatggctg aaagacactt                                               20

<210> SEQ ID NO 485
<211> LENGTH: 18
<212> TYPE: DNA
<213> ORGANISM: Artificial Sequence
<220> FEATURE:

<223> OTHER INFORMATION: Human BANF1 gene variant1

<400> SEQUENCE: 485
ccagtgttcc cagttccc                                                18

<210> SEQ ID NO 486
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 486
ccagtccaac tgcgagga                                                18

<210> SEQ ID NO 487
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 487
cgacgtgagt ctgagtct                                                18

<210> SEQ ID NO 488
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 488
gtccgtcttc taactctt                                                18

<210> SEQ ID NO 489
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 489
cgtcaagcct aagtcctt                                                18

<210> SEQ ID NO 490
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 490
gcagagaaag gaagtcct                                                18

<210> SEQ ID NO 491
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 491
cgagaagcga gaccttag                                                18

```
<210> SEQ ID NO 492
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 492
cctcaactct atagctct                                                 18

<210> SEQ ID NO 493
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 493
ctagtggctt gaggtatc                                                 18

<210> SEQ ID NO 494
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 494
ggattaagcc tgatcaag                                                 18

<210> SEQ ID NO 495
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 495
gactgcttcg gatgcctt                                                 18

<210> SEQ ID NO 496
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 496
ccttcttgtg atgctctc                                                 18

<210> SEQ ID NO 497
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 497
cctcatccag agtttgca                                                 18

<210> SEQ ID NO 498
<211> LENGTH: 18
<212> TYPE: DNA
<213> ORGANISM: Artificial Sequence
<220> FEATURE:
<223> OTHER INFORMATION: Human BANF1 gene variant1
```

```
<400> SEQUENCE: 498
cctgtcctct acgaagga                                                 18

<210> SEQ ID NO 499
<211> LENGTH: 20
<212> TYPE: DNA
<213> ORGANISM: Artificial Sequence
<220> FEATURE:
<223> OTHER INFORMATION: Human BANF1 gene variant1

<400> SEQUENCE: 499
gattgctatt gtcgtactca                                               20

<210> SEQ ID NO 500
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 500
ggattctcgc tcttgcat                                                 18

<210> SEQ ID NO 501
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 501
ggtgacagtt accagctt                                                 18

<210> SEQ ID NO 502
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 502
cctcactttc aatccgtt                                                 18

<210> SEQ ID NO 503
<211> LENGTH: 18
<212> TYPE: DNA
<213> ORGANISM: Artificial Sequence
<220> FEATURE:
<223> OTHER INFORMATION: Human BANF1 gene variant1

<400> SEQUENCE: 503
gcagaacagt cactgtcc                                                 18

<210> SEQ ID NO 504
<211> LENGTH: 20
<212> TYPE: DNA
<213> ORGANISM: Artificial Sequence
<220> FEATURE:
<223> OTHER INFORMATION: Human BANF1 gene variant1

<400> SEQUENCE: 504
gatcaataaa gtcagtggct                                               20

<210> SEQ ID NO 505
<211> LENGTH: 21
```

<212> TYPE: DNA
<213> ORGANISM: Artificial Sequence
<220> FEATURE:
<223> OTHER INFORMATION: Human BANF1 gene variant1

<400> SEQUENCE: 505
aagaagctgg aggaaagggg t                                              21

<210> SEQ ID NO 506
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 506
atgacaacct cccaaaagca                                                20

<210> SEQ ID NO 507
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 507
ccgagacttc gtggcaga                                                  18

<210> SEQ ID NO 508
<211> LENGTH: 15
<212> TYPE: DNA
<213> ORGANISM: Artificial Sequence
<220> FEATURE:
<223> OTHER INFORMATION: Human BANF1 gene variant2

<400> SEQUENCE: 508
agcctggctg ggatt                                                     15

<210> SEQ ID NO 509
<211> LENGTH: 17
<212> TYPE: DNA
<213> ORGANISM: Artificial Sequence
<220> FEATURE:
<223> OTHER INFORMATION: Human BANF1 gene variant2

<400> SEQUENCE: 509
caagaagctg gaggaaa                                                   17

<210> SEQ ID NO 510
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 510
ccagtttctg gtgctaaaga                                                20

<210> SEQ ID NO 511
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 511

-continued aagatgaaga cctcttcc                                                18

<210> SEQ ID NO 512
<211> LENGTH: 19
<212> TYPE: DNA
<213> ORGANISM: Artificial Sequence
<220> FEATURE:
<223> OTHER INFORMATION: Human BANF1 gene variant2

<400> SEQUENCE: 512
ggactgcttc ggatgcctt                                               19

<210> SEQ ID NO 513
<211> LENGTH: 19
<212> TYPE: DNA
<213> ORGANISM: Artificial Sequence
<220> FEATURE:
<223> OTHER INFORMATION: Human BANF1 gene variant2

<400> SEQUENCE: 513
agtggtgcga cgccttctt                                               19

<210> SEQ ID NO 514
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 514
ctctctggga agctctcaat                                              20

<210> SEQ ID NO 515
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 515
ttgctattgt cgtactcacc                                              20

<210> SEQ ID NO 516
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 516
gattctcgct cttgcatg                                                18

<210> SEQ ID NO 517
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 517
cagttccctg gtgacagtta                                              20

<210> SEQ ID NO 518
<211> LENGTH: 18
<212> TYPE: DNA
<213> ORGANISM: Artificial Sequence

```
<220> FEATURE:
<223> OTHER INFORMATION: Human BANF1 gene variant2

<400> SEQUENCE: 518
ccagctttcc tgaatgga                                                 18

<210> SEQ ID NO 519
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 519
ctcactttca atccgtttga                                               20

<210> SEQ ID NO 520
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 520
cagaacagtc actgtccttg                                               20

<210> SEQ ID NO 521
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 521
caccagtcca actgcgag                                                 18

<210> SEQ ID NO 522
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 522
tgcgacgtga gtctgagtct                                               20

<210> SEQ ID NO 523
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 523
cctccgaaaa ccgtactt                                                 18

<210> SEQ ID NO 524
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 524
ccttgtccgt cttctaactc                                               20
```

<210> SEQ ID NO 525
<211> LENGTH: 19
<212> TYPE: DNA
<213> ORGANISM: Artificial Sequence
<220> FEATURE:
<223> OTHER INFORMATION: Human BANF1 gene variant2

<400> SEQUENCE: 525
ccaggtccgt caagcctaa                                                19

<210> SEQ ID NO 526
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 526
gcagcagaga aaggaagt                                                 18

<210> SEQ ID NO 527
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 527
cctatctccc tcagaact                                                 18

<210> SEQ ID NO 528
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 528
gagaagcgag accttagaag                                               20

<210> SEQ ID NO 529
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 529
gcctcaactc tatagctcta                                               20

<210> SEQ ID NO 530
<211> LENGTH: 18
<212> TYPE: DNA
<213> ORGANISM: Artificial Sequence
<220> FEATURE:
<223> OTHER INFORMATION: Human BANF1 gene variant2

<400> SEQUENCE: 530
ccaacgtgga atgtttct                                                 18

<210> SEQ ID NO 531
<211> LENGTH: 22
<212> TYPE: DNA
<213> ORGANISM: Artificial Sequence
<220> FEATURE:
<223> OTHER INFORMATION: Human BANF1 gene variant2

<400> SEQUENCE: 531
gaagcggaag tggaagaaag tt                                          22

<210> SEQ ID NO 532
<211> LENGTH: 20
<212> TYPE: DNA
<213> ORGANISM: Artificial Sequence
<220> FEATURE:
<223> OTHER INFORMATION: Human BANF1 gene variant2

<400> SEQUENCE: 532
ctagtggctt gagattaagc                                             20

<210> SEQ ID NO 533
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 533
ccagagaagc tgctggtgat                                             20

<210> SEQ ID NO 534
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 534
ccacagctga aaccgagg                                               18

<210> SEQ ID NO 535
<211> LENGTH: 16
<212> TYPE: DNA
<213> ORGANISM: Artificial Sequence
<220> FEATURE:
<223> OTHER INFORMATION: Human PLOD3 gene

<400> SEQUENCE: 535
ctctgcggag ttcttc                                                 16

<210> SEQ ID NO 536
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 536
aactacactg tgcggacc                                               18

<210> SEQ ID NO 537
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 537
gtgatgtggc tcgaacag                                               18

<210> SEQ ID NO 538

```
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 538
ggttaaagaa ggaaatggag                                              20

<210> SEQ ID NO 539
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 539
ggaggatatg atcatcatgt                                              20

<210> SEQ ID NO 540
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 540
ggatagctac gacgtgat                                                18

<210> SEQ ID NO 541
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 541
cacagagctg ctgaagaa                                                18

<210> SEQ ID NO 542
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 542
tgctcttctc tgcagaga                                                18

<210> SEQ ID NO 543
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 543
gcttcctcaa ttctggtgg                                               19

<210> SEQ ID NO 544
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 544
```
attcatcggt tttgccacca                               20

<210> SEQ ID NO 545
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 545
agtggaagta caaggatga                                19

<210> SEQ ID NO 546
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 546
cagccttaat ctggatca                                 18

<210> SEQ ID NO 547
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 547
gtctcggatc tttcagaacc                               20

<210> SEQ ID NO 548
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 548
ggctttagat gaagtggt                                 18

<210> SEQ ID NO 549
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 549
gtttgatcgg aaccgtgt                                 18

<210> SEQ ID NO 550
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 550
ttgtggtcca tggaaacg                                 18

<210> SEQ ID NO 551
<211> LENGTH: 19
<212> TYPE: DNA

```
<213> ORGANISM: Artificial Sequence
<220> FEATURE:
<223> OTHER INFORMATION: Human PLOD3 gene

<400> SEQUENCE: 551
ccactaagct gcagctcaa                                                19

<210> SEQ ID NO 552
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 552
ccaatggctg gactcctga                                                19

<210> SEQ ID NO 553
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 553
gctgtggctt ctgcaacca                                                19

<210> SEQ ID NO 554
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 554
gtgtttgtgg aacagcct                                                 18

<210> SEQ ID NO 555
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 555
gctgctactc ctggactat                                                19

<210> SEQ ID NO 556
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 556
ttcctgcaca caacgaggt                                                20

<210> SEQ ID NO 557
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 557
ccacatcgct gactcctg                                                 18
```

<210> SEQ ID NO 558
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 558
agctccagga ccacttctca                                          20

<210> SEQ ID NO 559
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 559
atggccatgg acctgtgt                                            18

<210> SEQ ID NO 560
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 560
cgagtgtgag ttctacttca                                          20

<210> SEQ ID NO 561
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 561
gctgtcctca ccaacctg                                            18

<210> SEQ ID NO 562
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 562
ctgcgtatcc tcattgag                                            18

<210> SEQ ID NO 563
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 563
gagaacagga aggtgatc                                            18

<210> SEQ ID NO 564
<211> LENGTH: 18
<212> TYPE: DNA
<213> ORGANISM: Artificial Sequence
<220> FEATURE:

<223> OTHER INFORMATION: Human PLOD3 gene

<400> SEQUENCE: 564
caagctgtgg tccaactt                                    18

<210> SEQ ID NO 565
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 565
gaggactacg tggagctg                                    18

<210> SEQ ID NO 566
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 566
gtgtgtggaa tgtaccatac                                  20

<210> SEQ ID NO 567
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 567
agagggatgt gttctcggg                                   19

<210> SEQ ID NO 568
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 568
ccttctgtaa gagctttcga                                  20

<210> SEQ ID NO 569
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 569
acaagggcat cttcctccat                                  20

<210> SEQ ID NO 570
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 570
ctgagcaatc agcatgaa                                    18

<210> SEQ ID NO 571
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 571
ccacttccag atacgaca                                                 18

<210> SEQ ID NO 572
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 572
acctctggca gatcttcga                                                19

<210> SEQ ID NO 573
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 573
cgtcgactgg aaggagca                                                 18

<210> SEQ ID NO 574
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 574
gtacatccac gagaacta                                                 18

<210> SEQ ID NO 575
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 575
aaggaatcgt ggagcagcca                                               20

<210> SEQ ID NO 576
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 576
ctgctgtcag aacaaatg                                                 18

<210> SEQ ID NO 577
<211> LENGTH: 20
<212> TYPE: DNA
<213> ORGANISM: Artificial Sequence
<220> FEATURE:
<223> OTHER INFORMATION: Human PLOD3 gene

```
<400> SEQUENCE: 577
tgtgatgagc tggtggcaga                                              20

<210> SEQ ID NO 578
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 578
gcatgaggat tcaaggct                                                18

<210> SEQ ID NO 579
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 579
ctggaggcta cgagaatgt                                               19

<210> SEQ ID NO 580
<211> LENGTH: 18
<212> TYPE: DNA
<213> ORGANISM: Artificial Sequence
<220> FEATURE:
<223> OTHER INFORMATION: Human PLOD3 gene

<400> SEQUENCE: 580
tggacatcca catgaagc                                                18

<210> SEQ ID NO 581
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 581
tacgaggacc agtggctgca                                              20

<210> SEQ ID NO 582
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 582
catgaccgag agcctgttt                                               19

<210> SEQ ID NO 583
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 583
gtgatgaact tgtggttcg                                               20

<210> SEQ ID NO 584
<211> LENGTH: 18
```

```
<212> TYPE: DNA
<213> ORGANISM: Artificial Sequence
<220> FEATURE:
<223> OTHER INFORMATION: Human PLOD3 gene

<400> SEQUENCE: 584
agacgagcag ccgtctct                                               18

<210> SEQ ID NO 585
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 585
gactcatcca ccttcaccct                                             20

<210> SEQ ID NO 586
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 586
ttcctgcgct acgactgtgt                                             20

<210> SEQ ID NO 587
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 587
cacacgctac atcatggtgt                                             20

<210> SEQ ID NO 588
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 588
tgccattgtg cctttttagg                                             20

<210> SEQ ID NO 589
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 589
cacttcctga gttcatgttc                                             20

<210> SEQ ID NO 590
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 590
```

|   |   |
|---|---|
| cctgaactga atatgtcacc | 20 |

<210> SEQ ID NO 591
<211> LENGTH: 21
<212> TYPE: DNA
<213> ORGANISM: Artificial Sequence
<220> FEATURE:
<223> OTHER INFORMATION: Human PLOD3 gene

<400> SEQUENCE: 591

|   |   |
|---|---|
| cgcagtctca ctctgaataa a | 21 |

<210> SEQ ID NO 592
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 592

|   |   |
|---|---|
| ggacagtttg taagtcttg | 19 |

<210> SEQ ID NO 593
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 593

|   |   |
|---|---|
| tcacttcccc tgtccaggtt | 20 |

<210> SEQ ID NO 594
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 594

|   |   |
|---|---|
| tcagcttcca catgtgtcaa | 20 |

<210> SEQ ID NO 595
<211> LENGTH: 19
<212> TYPE: DNA
<213> ORGANISM: Artificial Sequence
<220> FEATURE:
<223> OTHER INFORMATION: Human PLOD3 gene

<400> SEQUENCE: 595

|   |   |
|---|---|
| gacaatcctc gccttgtct | 19 |

<210> SEQ ID NO 596
<211> LENGTH: 20
<212> TYPE: DNA
<213> ORGANISM: Artificial Sequence
<220> FEATURE:
<223> OTHER INFORMATION: Human PLOD3 gene

<400> SEQUENCE: 596

|   |   |
|---|---|
| catctggagc tttctgtagc | 20 |

<210> SEQ ID NO 597
<211> LENGTH: 18
<212> TYPE: DNA
<213> ORGANISM: Artificial Sequence

```
<220> FEATURE:
<223> OTHER INFORMATION: Human PLOD3 gene

<400> SEQUENCE: 597
gagatcccag gatcctgg                                               18

<210> SEQ ID NO 598
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 598
aatcaggatg ccactgtgta                                             20

<210> SEQ ID NO 599
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 599
ctggatgaga aggttagtga                                             20

<210> SEQ ID NO 600
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 600
tgtgggaact gtttctccag                                             20

<210> SEQ ID NO 601
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 601
ctggaccagt agtcaaca                                               18

<210> SEQ ID NO 602
<211> LENGTH: 19
<212> TYPE: DNA
<213> ORGANISM: Artificial Sequence
<220> FEATURE:
<223> OTHER INFORMATION: Human SF3B4 gene

<400> SEQUENCE: 602
ccaaaggata gagtcactg                                              19

<210> SEQ ID NO 603
<211> LENGTH: 21
<212> TYPE: DNA
<213> ORGANISM: Artificial Sequence
<220> FEATURE:
<223> OTHER INFORMATION: Human SF3B4 gene

<400> SEQUENCE: 603
cagcaccaag gctatggctt t                                           21
```

<210> SEQ ID NO 604
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 604
gtggaattct tgagtgagga					20

<210> SEQ ID NO 605
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 605
gctgactatg ccattaagat					20

<210> SEQ ID NO 606
<211> LENGTH: 19
<212> TYPE: DNA
<213> ORGANISM: Artificial Sequence
<220> FEATURE:
<223> OTHER INFORMATION: Human SF3B4 gene

<400> SEQUENCE: 606
acatgatcaa actctatgg					19

<210> SEQ ID NO 607
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 607
ggtgaacaaa gcatcagc					18

<210> SEQ ID NO 608
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 608
cctgagattg atgagaag					18

<210> SEQ ID NO 609
<211> LENGTH: 17
<212> TYPE: DNA
<213> ORGANISM: Artificial Sequence
<220> FEATURE:
<223> OTHER INFORMATION: Human SF3B4 gene

<400> SEQUENCE: 609
ggtcatctta caaaccc					17

<210> SEQ ID NO 610
<211> LENGTH: 18
<212> TYPE: DNA
<213> ORGANISM: Artificial Sequence
<220> FEATURE:
<223> OTHER INFORMATION: Human SF3B4 gene

```
<400> SEQUENCE: 610
cctgacacag gcaactcc                                                        18

<210> SEQ ID NO 611
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 611
gcttcatttg atgcttcgga                                                      20

<210> SEQ ID NO 612
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 612
tgcagcaatt gaagccatga                                                      20

<210> SEQ ID NO 613
<211> LENGTH: 19
<212> TYPE: DNA
<213> ORGANISM: Artificial Sequence
<220> FEATURE:
<223> OTHER INFORMATION: Human SF3B4 gene

<400> SEQUENCE: 613
gcagtacctc tgtaaccgt                                                       19

<210> SEQ ID NO 614
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 614
caccgtatct tatgccttca                                                      20

<210> SEQ ID NO 615
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 615
gaacgacttc tggcagctca                                                      20

<210> SEQ ID NO 616
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 616
cctcatcagc tgtttgcaga                                                      20

<210> SEQ ID NO 617
```

```
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 617
tggtcatgga cactcacatc                                                    20

<210> SEQ ID NO 618
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 618
gatgtctcag atgcagct                                                      18

<210> SEQ ID NO 619
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 619
cctcatggct taggacat                                                      18

<210> SEQ ID NO 620
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 620
tcacattttc cttcctcctg                                                    20

<210> SEQ ID NO 621
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 621
ccttggacca atcagagatg                                                    20

<210> SEQ ID NO 622
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 622
ggcaaaggta ctaatccctt                                                    20

<210> SEQ ID NO 623
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 623
```
ttccacagga ggtatttc                                            18

<210> SEQ ID NO 624
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 624
ggtcctgagt attttgca                                            18

<210> SEQ ID NO 625
<211> LENGTH: 19
<212> TYPE: DNA
<213> ORGANISM: Artificial Sequence
<220> FEATURE:
<223> OTHER INFORMATION: Human SF3B4 gene

<400> SEQUENCE: 625
ccaaatctgc aagaaggct                                           19

<210> SEQ ID NO 626
<211> LENGTH: 21
<212> TYPE: DNA
<213> ORGANISM: Artificial Sequence
<220> FEATURE:
<223> OTHER INFORMATION: Human SF3B4 gene

<400> SEQUENCE: 626
ggaactcttc agcacatcct t                                        21

<210> SEQ ID NO 627
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 627
ctctggacaa cagaagaaga                                          20

<210> SEQ ID NO 628
<211> LENGTH: 18
<212> TYPE: DNA
<213> ORGANISM: Artificial Sequence
<220> FEATURE:
<223> OTHER INFORMATION: Human SF3B4 gene

<400> SEQUENCE: 628
tgagagcagt gtgattct                                            18

<210> SEQ ID NO 629
<211> LENGTH: 17
<212> TYPE: DNA
<213> ORGANISM: Artificial Sequence
<220> FEATURE:
<223> OTHER INFORMATION: Human SF3B4 gene

<400> SEQUENCE: 629
caagtctagc agtgcat                                             17

<210> SEQ ID NO 630
<211> LENGTH: 19
<212> TYPE: DNA

<213> ORGANISM: Artificial Sequence
<220> FEATURE:
<223> OTHER INFORMATION: Human SF3B4 gene

<400> SEQUENCE: 630
ctcgctaaga caactagca                                                19

<210> SEQ ID NO 631
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 631
caggttaagt ttcggaggct                                               20

<210> SEQ ID NO 632
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 632
gcttccaggc acctcctctt                                               20

<210> SEQ ID NO 633
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 633
gaagtggaag tcgtgctgag                                               20

<210> SEQ ID NO 634
<211> LENGTH: 20
<212> TYPE: DNA
<213> ORGANISM: Artificial Sequence
<220> FEATURE:
<223> OTHER INFORMATION: Human SF3B4 gene

<400> SEQUENCE: 634
gatctctttc gccatggctg                                               20

<210> SEQ ID NO 635
<211> LENGTH: 19
<212> TYPE: RNA
<213> ORGANISM: Artificial Sequence
<220> FEATURE:
<223> OTHER INFORMATION: siRNA sense strand

<400> SEQUENCE: 635
gcaguaccuc uguaaccgu                                                19

<210> SEQ ID NO 636
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 636
acgguuacag agguacugc                                                19

```
<210> SEQ ID NO 637
<211> LENGTH: 21
<212> TYPE: RNA
<213> ORGANISM: Artificial Sequence
<220> FEATURE:
<223> OTHER INFORMATION: siRNA sense strand

<400> SEQUENCE: 637
aagaagcugg aggaaagggg u                                           21

<210> SEQ ID NO 638
<211> LENGTH: 21
<212> TYPE: RNA
<213> ORGANISM: Artificial Sequence
<220> FEATURE:
<223> OTHER INFORMATION: siRNA antisense strand

<400> SEQUENCE: 638
accccuuucc uccagcuucu u                                           21

<210> SEQ ID NO 639
<211> LENGTH: 19
<212> TYPE: RNA
<213> ORGANISM: Artificial Sequence
<220> FEATURE:
<223> OTHER INFORMATION: siRNA sense strand

<400> SEQUENCE: 639
gcaucuggag cuuucugua                                              19

<210> SEQ ID NO 640
<211> LENGTH: 19
<212> TYPE: RNA
<213> ORGANISM: Artificial Sequence
<220> FEATURE:
<223> OTHER INFORMATION: siRNA antisense strand

<400> SEQUENCE: 640
uacagaaagc uccagaugc                                              19
```

PHARMACEUTICAL COMPOSITION FOR PREVENTING OR TREATING LIVER CANCER

CROSS REFERENCE TO RELATED APPLICATIONS AND CLAIM OF PRIORITY

This application is a divisional application of application Ser. No. 16/634,675, filed on Jan. 28, 2020, which is a National Stage entry from International Application No. PCT/KR2018/008611, filed on Jul. 30, 2018, which claims priority to the benefit of U.S. Patent Application No. 62/538,034 filed in the US Patent Office on Jul. 28, 2017 and Korean Patent Application No. 10-2018-0088375 filed in the Korean Intellectual Property Office on Jul. 30, 2018, the entire contents of which are incorporated herein by reference.

BACKGROUND

1. Technical Field

The present invention relates to a pharmaceutical composition for preventing or treating liver cancer.

2. Background Art

Hepatocellular carcinoma (HCC) is the second leading cause of cancer-related deaths worldwide. HCC is one of few cancers that have been recently increased in incidence.

The primary treatment of HCC is surgical resection, and most of patients are not eligible for curative treatment at the initial treatment stage. Resection and transdermal ablation involve a recurrence rate of 70% after 5 years and thus are closely related to the survival rate.

Like other cancers, HCC is also characterized by multiple tumor progression. The damaged liver tissues in the early stage evolve to small nodular hypercellular lesions called dysplastic nodules (DNs). Such pre-cancerous lesion develops into small, well-differentiated hepatocytes with an ambiguous nodular pattern and then progresses to early hepatocellular carcinoma (eHCC), which is defined as progressive HCC characterized by an epileptic appearance and frequent microvascular invasion. Based on current knowledge of an occurrence of multilevel HCC, high-critical patients are closely followed up, and diagnostic images show that a specific lesion with a small size and unknown cause was increased in number. Ultrasound-guided needle biopsy is performed on such lesions. The lesion would be subjected to treatment if it is determined as a cancer by histological diagnosis. However, eHCC generally exhibits minimal dysplasia and lacks clear invasive or destructive growth. Therefore, even for hepatopathologists, it is often difficult to distinguish recurrent nodules, precancerous lesions and early lesions. Due to such reasons, discovery of objective molecular markers that standardize histological diagnosis of eHCC and induce appropriate therapy is eagerly required. In addition, the discovery of biomarkers related to accurate HCC diagnosis may facilitate identification of precancerous lesions possibly progressing to HCC and to determine surgically resectable lesions, thereby supporting a surgeon to design a surgical range in HCC patients. Identifying additional molecular markers that predict possible occurrence of HCC in precancerous lesions may be helpful for identifying patients at risk for recurrence following surgical resection.

The present study is intended to establish a gene selection strategy to identify potential causative genes by combining clinicopathological and gene expression data of staged hepatocarcinoma tissues defined by hepatopathologists. As a result, 10 genes expected to be the cause of early stage HCC could be selected.

Clinical and experimental studies have demonstrated that barriers to procollagen-lysine, 2-oxoglutarate 5-dioxygenase 3 and splicing factor 3b subunit 4 among the 10 presumptive driving genes could indicate HCC in precancerous lesions, and also could diagnose eHCC in a large scale of HCC patients, compared to glypican 3, glutamine synthetase and heat shock protein 70 which are current HCC diagnostic marker trio.

In vivo experiments and in vitro tumor formation analysis demonstrated that target destruction of BANF1, PLOD3 and SF3B4 genes inhibits tumor and metastatic characteristics of HCC cells. Excessive response of SFB4 could increase slug in p27 and HCC cells to inhibit epithelial-mesenchymal transition (EMT), which contributes to transformation and proliferation of malignant cells, hence interfering with a cell cycle checkpoint and thus causing over-activation of spliceosome. Further, it could be seen that production of selective splicing variants inhibiting the growth of KLF4 tumor was accelerated.

The results described above suggest that novel HCC diagnostic markers, that is, BANF1, PLOD3 and SF3B contribute to early malignant transformation of hepatocytes in formation of hepatic tumor and are also targets for molecular therapy of liver malignancy.

SUMMARY

It is an object of the present invention to provide a pharmaceutical composition for preventing or treating liver cancer that knockdown a specific gene highly expressed in early stage liver cancer cells.

1. A pharmaceutical composition for preventing or treating liver cancer, including: siRNA which includes a sense RNA having at least one sequence selected from the group consisting of sequences of SEQ ID NOs: 5 to 157 and 635, and an antisense RNA having a complementary sequence thereto; or dsRNA having at least one sequence selected from the group consisting of sequences of SEQ ID NOs: 158 to 310.

2. The composition according to the above 1, wherein the composition includes:

siRNA which includes a sense RNA having at least one sequence selected from the group consisting of sequences of SEQ ID NOs: 5 to 12, 14 to 19, 21, 23, 24, 26, 28 to 34, 35 to 37, 39 to 41, 43, 45 to 47, 49 to 53, 55 to 60, 62 to 73, 75 to 81, 84 to 87, 89 to 98, 100 to 102, 105 to 116, 118 to 128, 130 to 154, 156 to 157, 635, 637 and 639 and an antisense RNA having a complementary sequence thereto; or dsRNA having at least one sequence selected from the group consisting of sequences of SEQ ID NOs: 158 to 165, 167 to 172, 174, 176, 177, 179, 181 to 187, 188 to 190, 192 to 194, 196, 198 to 200, 202 to 206, 208 to 213, 215 to 226, 228 to 234, 237 to 240, 242 to 251, 253 to 255, 258 to 269, 271 to 281, 283 to 307, 309 and 310.

3. The composition according to the above 1, wherein the composition includes:

siRNA which includes a sense RNA having at least one sequence selected from the group consisting of sequences of SEQ ID NOs: 5 to 28 and 637, and an antisense RNA having a complementary sequence thereto; or dsRNA having at least one sequence selected from the group consisting of sequences of SEQ ID NOs: 158 to 181.

4. The composition according to the above 1, wherein the composition includes:
siRNA which includes a sense RNA having at least one sequence selected from the group consisting of sequences of SEQ ID NOs: 29 to 55, and an antisense RNA having a complementary sequence thereto; or
dsRNA having at least one sequence selected from the group consisting of sequences of SEQ ID NOs: 182 to 208.

5. The composition according to the above 1, wherein the composition includes:
siRNA which includes a sense RNA having at least one sequence selected from the group consisting of sequences of SEQ ID NOs: 56 to 120 and 639, and an antisense RNA having a complementary sequence thereto; or
dsRNA having at least one sequence selected from the group consisting of sequences of SEQ ID NOs: 209 to 273.

6. The composition according to the above 1, wherein the composition includes:
siRNA which includes a sense RNA having at least one sequence selected from the group consisting of sequences of SEQ ID NOs: 121 to 157 and 635, and an antisense RNA having a complementary sequence thereto; or
dsRNA having at least one sequence selected from the group consisting of sequences of SEQ ID NOs: 274 to 310.

7. The composition according to any one of the above 1 to 6,
wherein the siRNA or dsRNA is loaded on at least one carrier selected from the group consisting of liposomes, lipofectamines, dendrimers, micelles, porous silica particles, amino clay, gold nanoparticles, magnetic nanoparticles, graphene, oxidized graphene, chitosan, dextran, pectin, manganese dioxide two-dimensional sheet, PVA, gelatin, silica, glass particles, protamine, exosome, polyethyleneimine, N-butyl cyanoacrylate, gel foam, ethanol, nanocrystals, nanotubes, carbon nanoparticles, hyaluronic acid, iron oxide, polylactic acid, polybutyl cyanoacrylate, albumin, lipid particles, polyethylene glycol, poly-L-guluronic alginate, polyglycolic-polylactic acid, polydioxanone, polyglycolic acid-co-caprolactone, polypropylene and hydrogel.

8. The composition according to the above 7,
wherein the carrier is a porous silica particle characterized in that t when a ratio of absorbance in the following Equation 1 becomes 1/2 is 20 or more:

$$A_t/A_0 \quad \text{[Equation 1]}$$

(wherein $A_0$ is absorbance of the porous silica particle measured by placing 5 ml of a suspension including 1 mg/ml of the porous silica particle into a cylindrical dialysis membrane having pores with a diameter of 50 kDa,
15 ml of the same solvent as the suspension is placed outside the dialysis membrane while being in contact with the dialysis membrane, followed by horizontal agitation at 60 rpm and 37° C. inside and outside the dialysis membrane, and
$A_t$ is absorbance of the porous silica particle measured after t hours elapses from the measurement of $A_0$).

9. The composition according to the above 8, wherein the t is 40 or more.

10. The composition according to the above 8,
wherein the siRNA includes a sense RNA having at least one sequence selected from the group consisting of sequences of SEQ ID NOs: 28, 119 and 136, and an antisense RNA having a complementary sequence thereto, and
the dsRNA has at least one sequence selected from the group consisting of sequences of SEQ ID NOs: 181, 272 and 289.

11. The composition according to the above 8,
wherein the porous silica particle has a hydrophilic substituent or a hydrophobic substituent.

12. The composition according to the above 8,
wherein the porous silica particle has at least one hydrophilic substituent selected from the group consisting of aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, ether, indene, sulfonyl, methylphosphonate, polyethylene glycol, substituted or unsubstituted $C_1$ to $C_{30}$ alkyl, substituted or unsubstituted $C_3$ to $C_{30}$ cycloalkyl, substituted or unsubstituted $C_6$ to $C_{30}$ aryl, and $C_1$ to $C_{30}$ ester groups.

13. The composition of claim 8,
wherein the porous silica particle is positively or negatively charged on an outer surface of the particle or an inside of a pore thereof at neutral pH.

14. The composition of claim 8,
wherein the porous silica particle is positively charged on an outer surface of the particle or an inside of a pore thereof at neutral pH.

15. The composition of claim 8,
wherein the porous silica particle has an average particle diameter of 100 to 400 nm and a pore diameter of 4 to 30 nm.

The pharmaceutical composition of the present invention provides preventive and therapeutic effects of liver cancer by specifically knocking down the genes expressed in early stage liver cancer cells, so as to prevent the development of liver cancer and inhibit the metastasis and proliferation of liver cancer cells.

Figure 3:
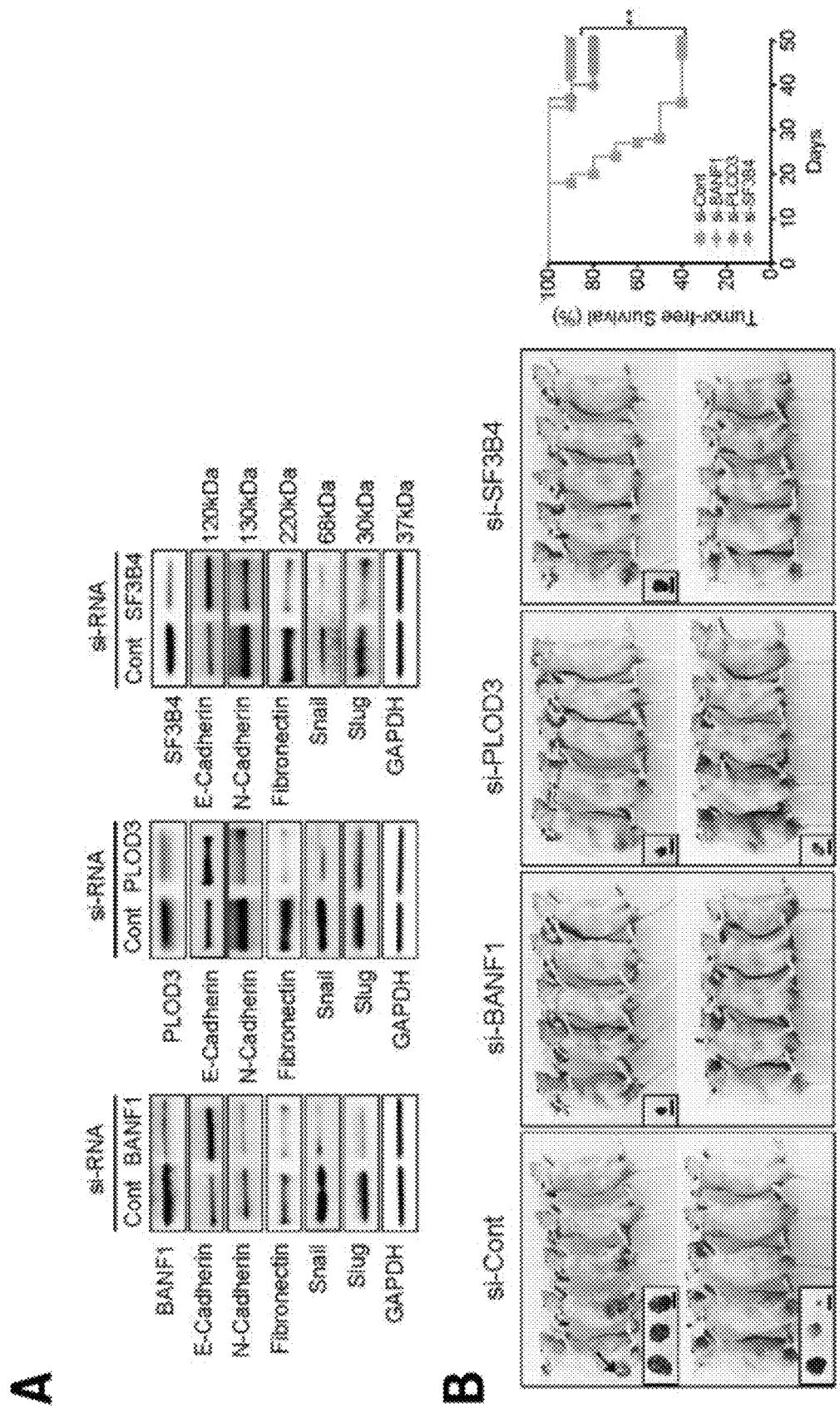

A of FIG. 3 is views illustrating results of analyzing expression levels of markers corresponding to siRNAs and EMT regulatory proteins by a method described in Example 1-9, respectively, after in vitro transfection of siRNAs to SNU-449 cell line in Example 1 by the method described in Example 1-2, wherein each siRNA includes a sense RNA having a sequence in Table 12 and an antisense RNA having a complementary sequence to the sequence of the sense RNA; and B of FIG. 3 is views illustrating the analyzed results of hepatic tumor sizes and survival rates of mice, after subcutaneous injection of transfected cells in the above (A) into athymic nude mice.

Figure 4:
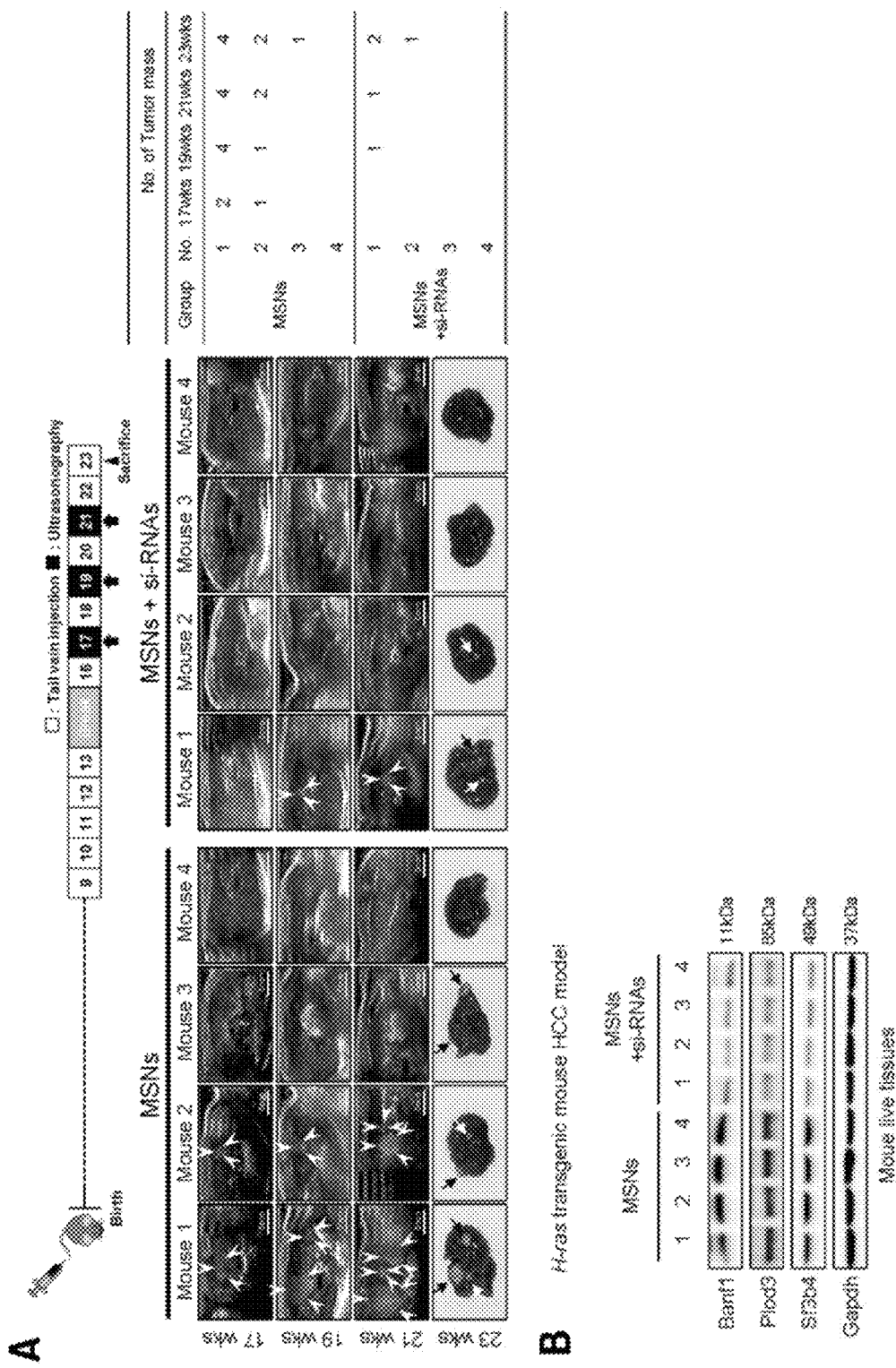

A of FIG. 4 is views illustrating processes of in vivo transfection of siRNAs by a method described in Example 1-8, ultrasonic images and the number of tumors over time, wherein each siRNA includes a sense RNA having a sequence in Table 13 and an antisense RNA having a complementary sequence to the sequence of the sense RNA; and B of FIG. 4 is a view illustrating results of analyzing expression inhibitory levels of siRNAs loaded on porous nanoparticles to indicator genes corresponding to the siR-NAs by the method described in Example 1-9.

Figure 5:
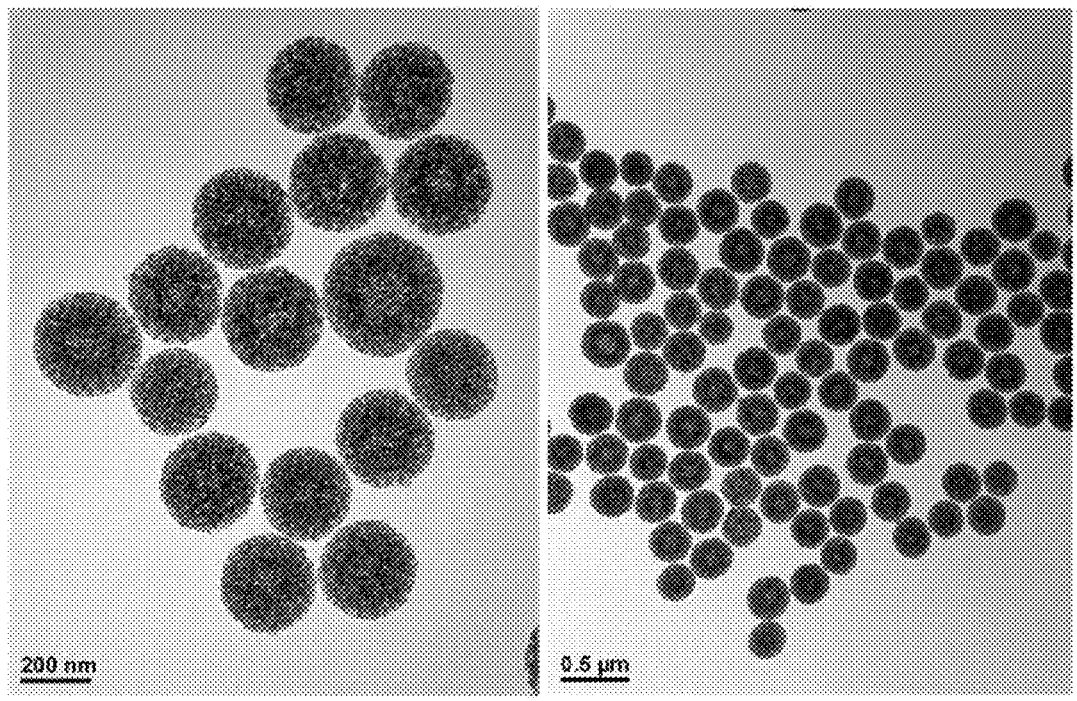

FIG. 5 is micrographs illustrating porous silica particles.

Figure 6:
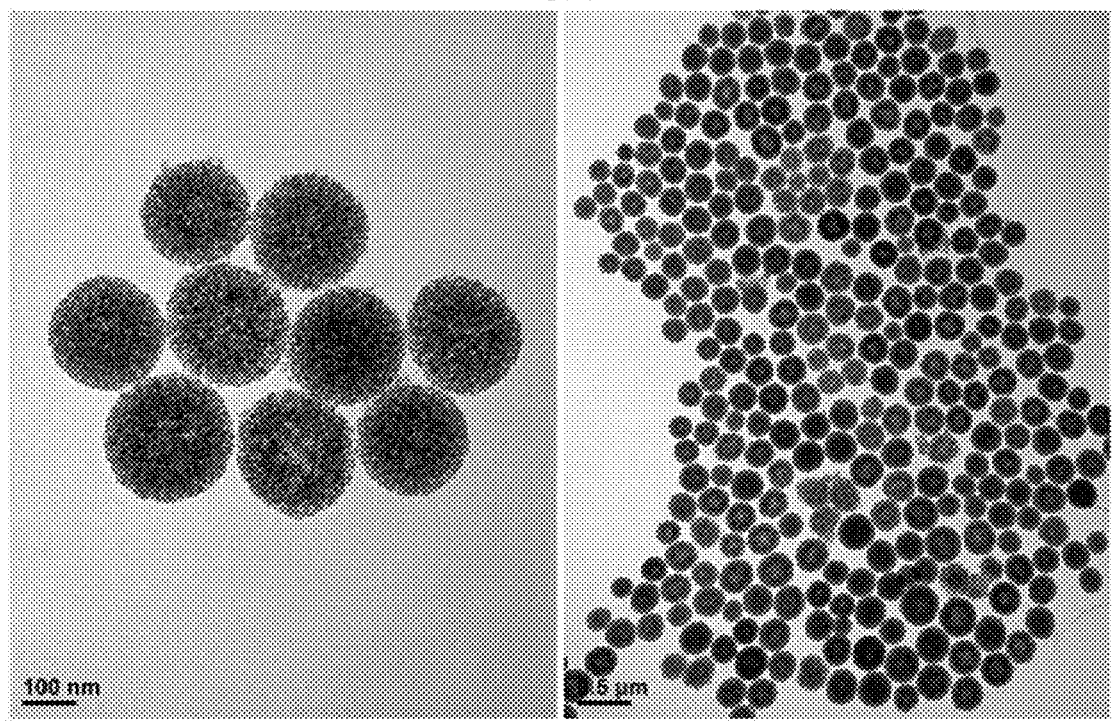

FIG. 6 is micrographs illustrating porous silica particles.

Figure 7:
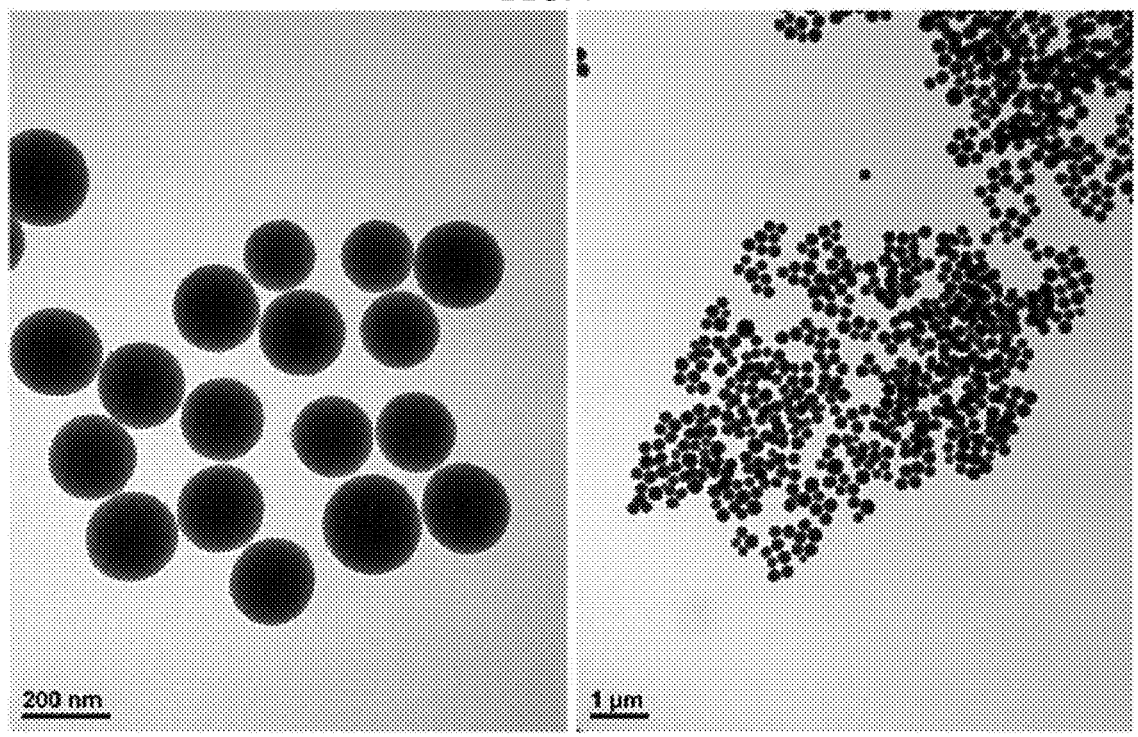

FIG. 7 is micrographs illustrating small pore particles during production of the porous silica particles.

Figure 8:
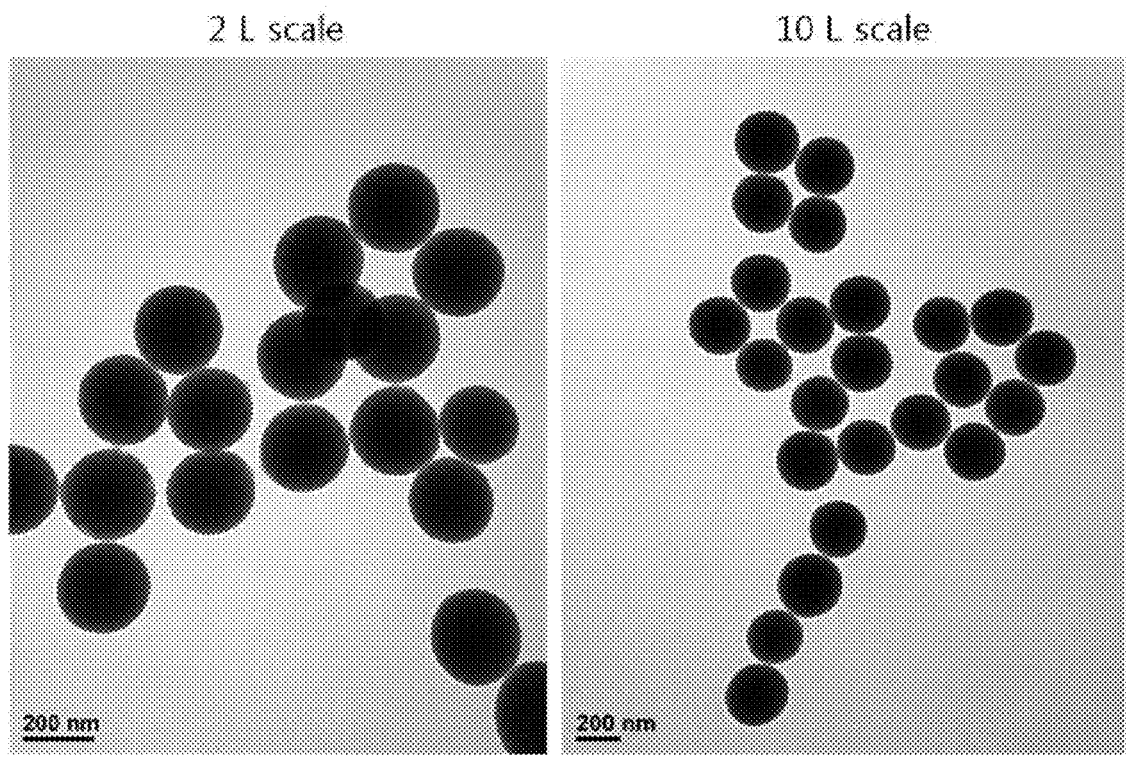

FIG. 8 is micrographs illustrating small pore particles.

Figure 9:
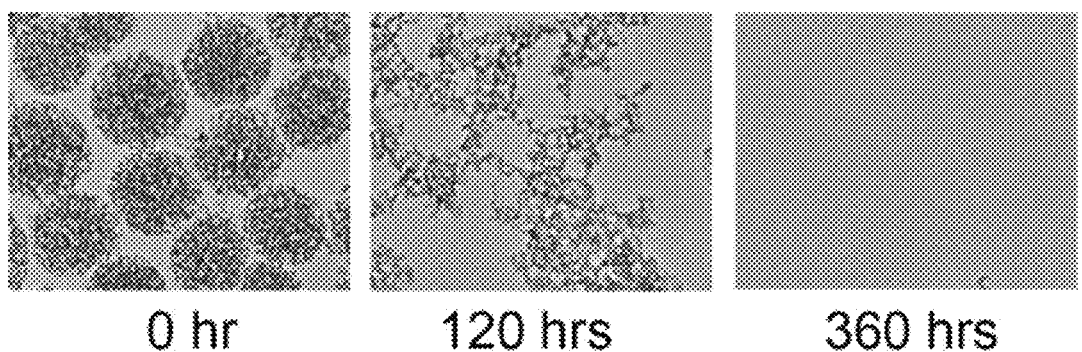

FIG. 9 is micrographs demonstrating biodegradability of porous silica particles.

Figure 10:
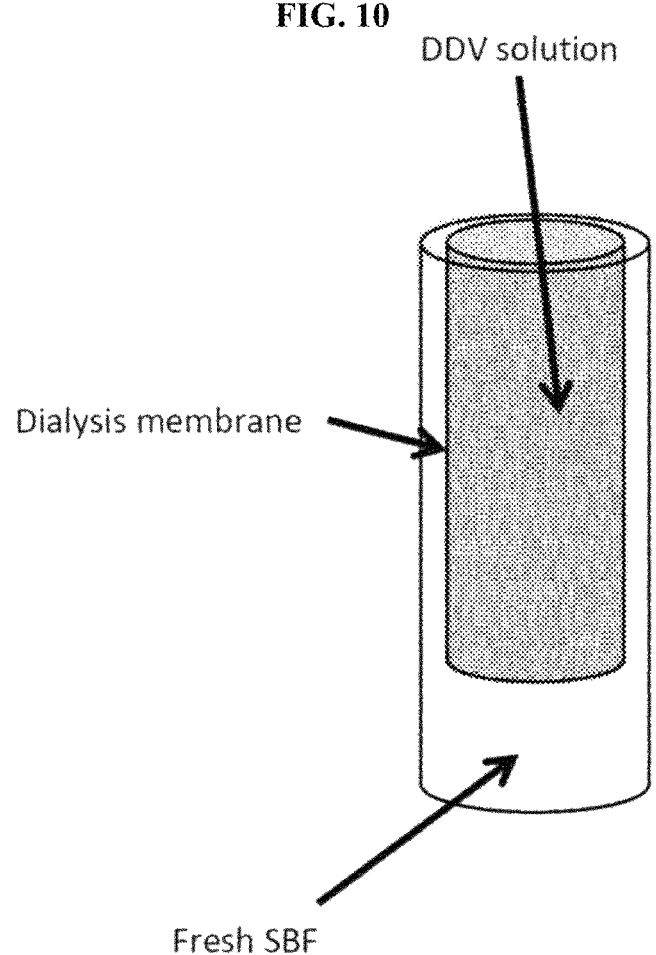

FIG. 10 is a view illustrating a tube having a cylindrical dialysis membrane.

Figure 11:
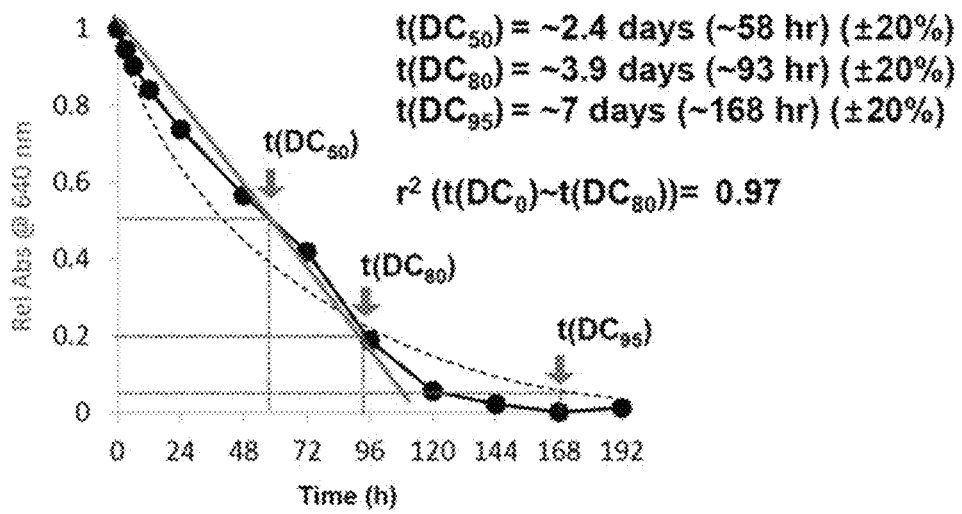

FIG. 11 is a graph illustrating results of absorbance reduction of the porous silica particles over time.

Figure 12:
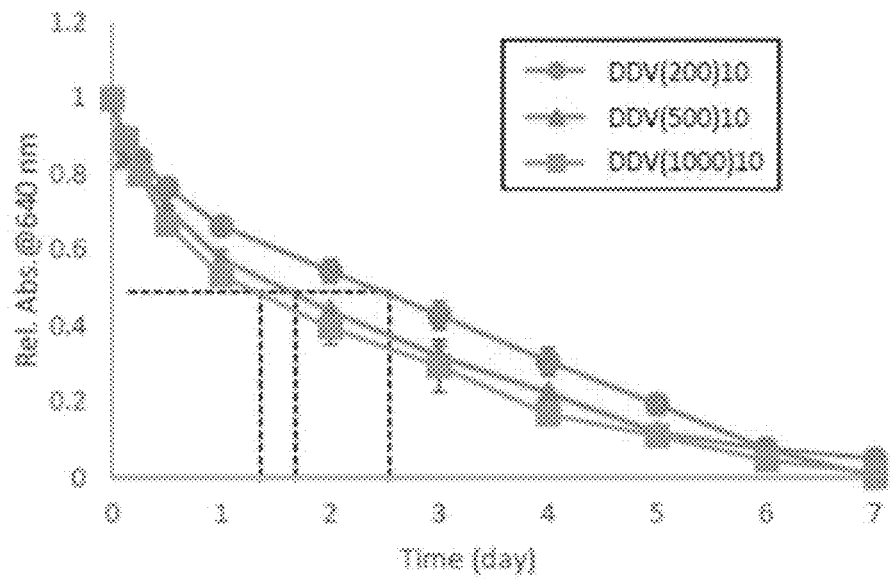

FIG. 12 is a graph and a table illustrating results of absorbance reduction by particle diameter of the porous silica particles over time.

Figure 13:
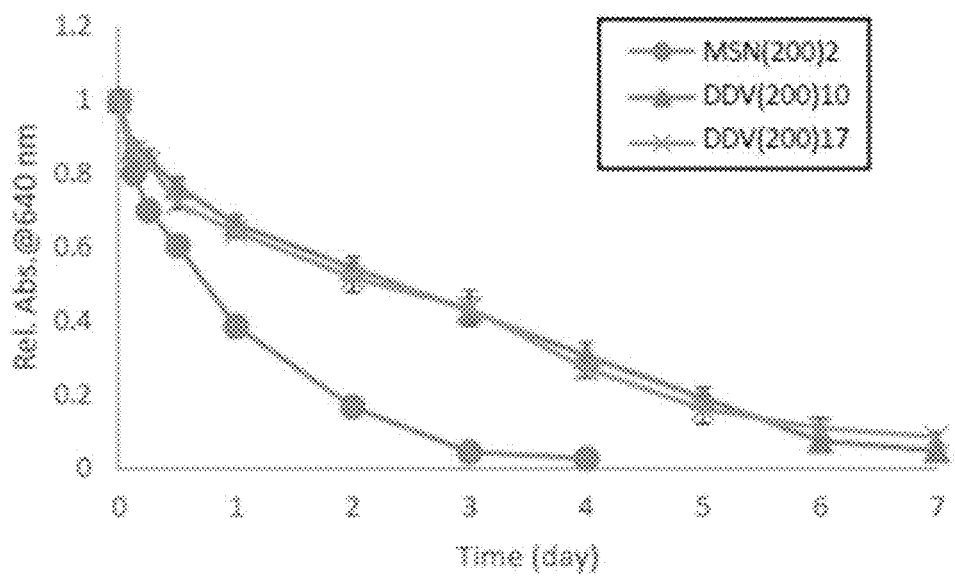

FIG. 13 is a graph and a table illustrating results of absorbance reduction by pore diameter of the porous silica particles over time.

Figure 14:
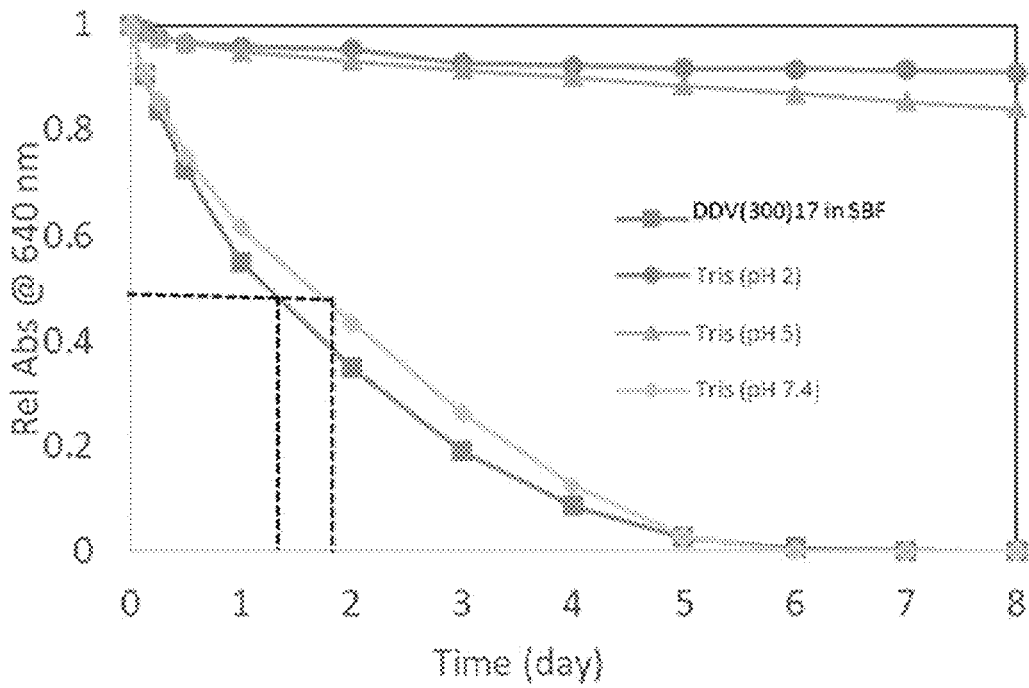

FIG. 14 is a graph illustrating results of absorbance reduction of the porous silica particles by pH in environments over time.

Figure 15:
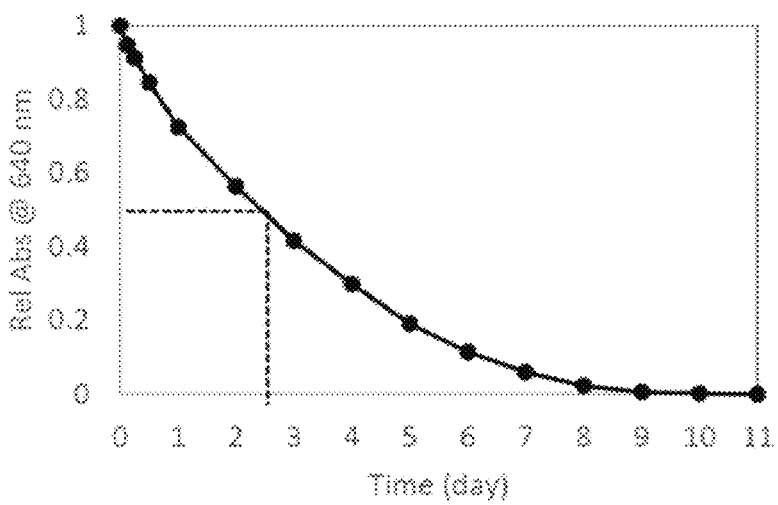

FIG. 15 is a graph illustrating results of absorbance reduction of the porous silica particles over time.

Figure 16:
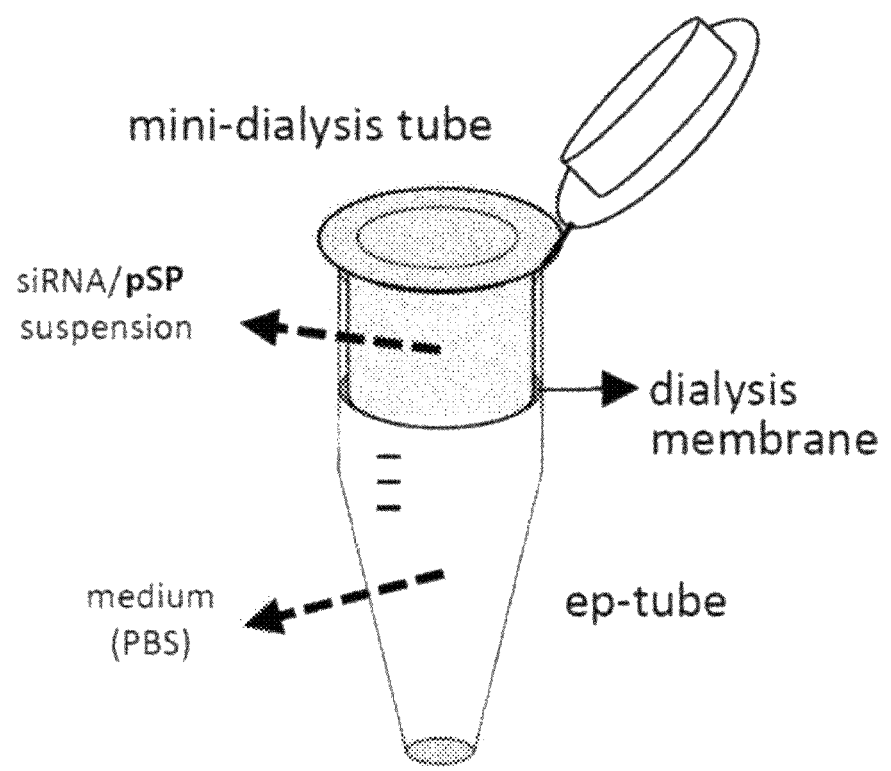

FIG. 16 is a view illustrating a tube for identifying release of bioactive material from the porous silica particles.

Figure 17:
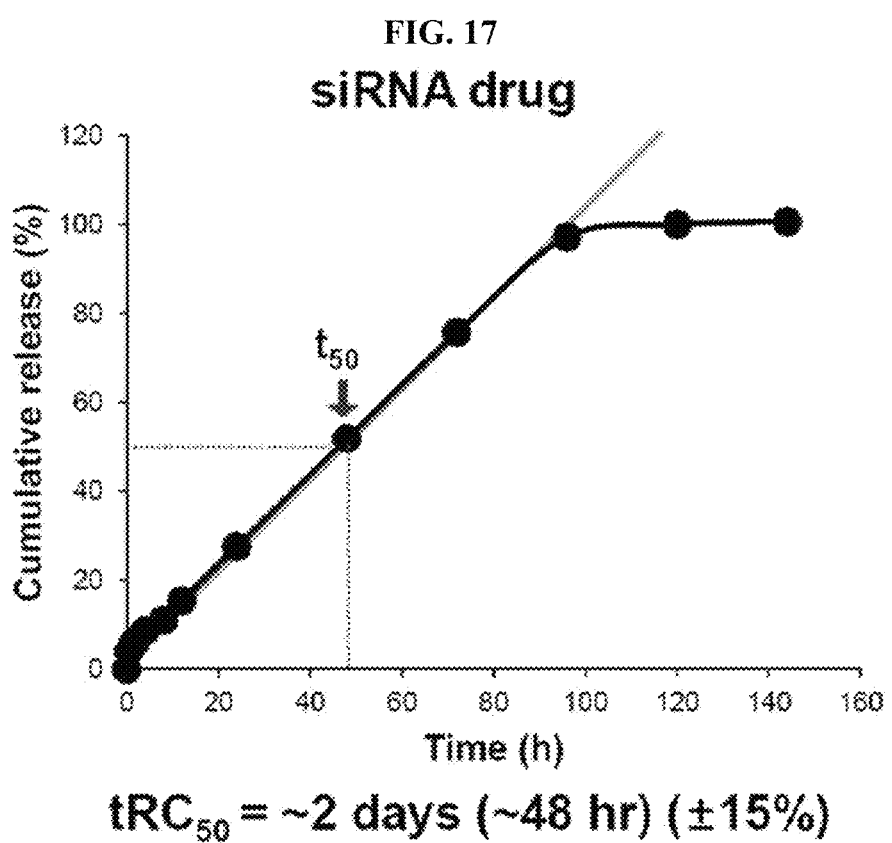

FIG. 17 is a graph illustrating release of bioactive material loaded on the porous silica particles over time.

FIG. 18 is micrographs demonstrating siRNA release in mice by loading the porous silica particles with siRNA.

DETAILED DESCRIPTION

The terms used in the present invention are defined as follows.

"siRNA" refers to a nucleic acid molecule capable of mediating RNA interference or gene silencing. siRNA can inhibit expression of a target gene and may be provided as an efficient gene knockdown method or as a gene therapy method. The siRNA molecule may have a structure in which a sense strand (a sequence corresponding to mRNA sequence of the target gene) and an antisense strand (a complementary sequence to mRNA sequence of the target gene) are located on sides opposite to each other to form a double chain. In addition, siRNA molecules may have a single stranded structure with self-complementary sense and antisense strands. The siRNA is not limited to a complete pair of double-stranded RNA modalities that are paired with each other, but may also include modalities that are not paired due to a mismatch (the corresponding base is not complementary), a bulge (no base corresponding to one chain) or the like. The siRNA terminal structure may include blunt or cohesive terminals as long as it can inhibit expression of a target gene by RNA interference (RNAi) effects. The cohesive terminal structure may be a 3'-terminal protruding structure and 5'-terminal protruding structure. Further, siRNA molecules may have a form in which a short nucleotide sequence (e.g., about 5-15 nt) is inserted between the self-complementary sense and the antisense strands. In this case, the siRNA molecule formed by expression of the nucleotide sequence may form a hairpin structure by intramolecular hybridization, which in turn forms a stem-and-loop structure on the whole. This stem-and-loop structure may be processed in vitro or in vivo to produce siRNA molecules capable of mediating RNAi.

"dsRNA" refers to a siRNA precursor molecule that meets a RISC complex containing DICER enzyme (Ribonuclease III) of a target cell and is cleaved into siRNA. In this process, RNAi is generated. dsRNA has a longer sequence by several nucleotides than siRNA and may have a structure wherein a sense strand (a sequence corresponding to mRNA sequence of the target gene) and an antisense strand (a sequence complementary to mRNA sequence of the target gene) are located on sides opposite to each other to form a double chain.

"Nucleic acid" may include any DNA or RNA, for example, chromosomes, mitochondria, viruses and/or bacterial nucleic acids present in a tissue sample. One or both strands of a double-stranded nucleic acid molecule may be included, and further any fragment or portion of an intact nucleic acid molecule.

"Gene" refers to any nucleic acid sequence or portion thereof that has a functional role at the time of protein coding or transcription, or in the control of other gene expressions. The gene may include only a portion of the nucleic acid encoding or expressing any nucleic acid or protein that encodes the functional protein. The nucleic acid sequence may involve gene abnormality in exon, intron, an initiation or termination region, a promoter sequence, another regulatory sequence or a specific sequence adjacent to the gene.

As used herein, the term "gene expression" generally refers to a cellular process in which a polypeptide having biological activity is produced from a DNA sequence and exhibits biological activity in the cell. In this sense, the gene expression may include not only transcription and translation processes but also post-transcription and post-translation processes that may affect the biological activity of the gene or gene product. Such processes may include polypeptide synthesis, transport and post-translational modification as well as RNA synthesis, processing and transport, but it is not limited thereto. In the case of a gene which does not encoding a protein product such as siRNA gene, the term "gene expression" refers to a process in which a precursor siRNA is produced from a gene. Normally, the above process is referred to as transcription, although a transcription product of siRNA gene is not translated to produce a protein, unlike the transcription induced by RNA polymerase II on a protein coding gene. Nevertheless, the formation of mature siRNAs from siRNA genes may be encompassed by the term "gene expression" as that term is used herein.

As used herein, the term "target gene" refers to a gene targeted for modulation using the method and composition in the subject matters disclosed herein. Therefore, the target gene includes a nucleic acid sequence with a specific expression level down-regulated by siRNA into mRNA or a polypeptide level. Similarly, the term "target RNA" or "target mRNA" refers to a transcript of the target gene that is bound to siRNA and induces modulation of expression in the target gene.

As used herein, the term "transcription" refers to a cellular process involving interaction between an expression-inducible gene, which is RNA of structural information present in a coding sequence of the gene, and RNA polymerase.

As used herein, the expression "down-regulation" refers to considerably decreasing the expression of a specific gene into mRNA or the expression level into a protein by gene transcription or gene translation in activated cells, as compared to normal tissue cells.

As used herein, the term "treatment" means an approach to obtain beneficial or desired clinical results. For the purposes of the present invention, the beneficial or desired clinical results may include, without limitation, alleviation of symptoms, reduction in an extent of disease, stabilization (i.e., not worsening) of disease state, delayed progression of disease or reduction in progress rate of disease, improvement, temporary mitigation and alleviation of disease state (partially or wholly), whether or not it is detectable. Further, the term "treatment" may also refer to increasing the survival rate compared to that expected survival when untreated. The treatment refers to both therapeutic treatment and prophylactic or preventative measures. Such treatments may include treatments required for disorders that have already occurred as well as disorders to be prevented.

As used herein, the term "prevention" means any action to inhibit or delay development of a related disease. It will be apparent to those skilled in the art that the composition mentioned herein may prevent initial symptoms, or related diseases in a case of administering before symptoms appear.

Hereinafter, the present invention will be described in detail.

The present invention provides a pharmaceutical composition for preventing or treating liver cancer, that is, hepatocellular carcinoma (HCC), which includes: siRNA which includes a sense RNA having at least one sequence selected from the group consisting of sequences of SEQ ID NOs: 5 to 157, as well as antisense RNA having a complementary sequence thereto; or dsRNA having at least one sequence selected from the group consisting of sequences of SEQ ID NOs: 158 to 310.

The siRNA or dsRNA of the present invention may be derived from animals including humans, such as monkeys, pigs, horses, cows, sheep, dogs, cats, mice, rabbits, and the like, and is preferably derived from humans.

The siRNA or dsRNA of the present invention may be modified by deletion, substitution or insertion of a functional equivalent of nucleic acid molecule constituting the siRNA or dsRNA, for example, a part of the base sequence in the siRNA or dsRNA of the present invention, however, may also be a concept including variants which are capable of functionally performing the same action as the siRNA or dsRNA of the present invention.

The siRNA or dsRNA of the present invention may be isolated or prepared using standard molecular biology techniques, such as chemical synthesis methods or recombinant methods, or may include commercially available ones. Further, the composition of the present invention may include not only siRNA or dsRNA itself of the present invention but also other substances, for example, compounds, natural products, novel proteins, etc. which are capable of increasing an expression rate of the siRNA or dsRNA of the present invention in cells.

Meanwhile, the siRNA or dsRNA of the present invention may be provided in a state of being included in a vector for intracellular expression.

The siRNA or dsRNA of the present invention may be introduced into cells by various transformation techniques such as a complex of DNA and DEAE-dextran, a complex of DNA and a nuclear protein, a complex of DNA and lipid and the like. To this end, the siRNA or dsRNA of the present invention may be provided in a form of being contained in a carrier enabling efficient introduction into a cell. The carrier is preferably a vector, and both viral vectors and non-viral vectors are usable. As the viral vector may include lentivirus, retrovirus, adenovirus, herpes virus and avipox virus vector, etc., preferably, is a lentivirus vector, but it is not limited thereto. Lentivirus is one type of retrovirus characterized by infecting a non-mitotic cell as well as a mitotic cell due to nucleophilic property of pre-integrated complex (a virus "shell") that allows active incorporation into nucleopores or a complete nuclear membrane.

In addition, the vector containing siRNA or dsRNA of the present invention preferably includes a selection marker. The "selection marker" is intended to facilitate selection or screening of cells into which siRNA or dsRNA of the present invention has been introduced. The selection marker used in the vector is not particularly limited as long as it is a gene capable of easily detecting or determining whether or not the vector was introduced. However, examples thereof may typically include markers endowing selectable phenotypes such as drug resistance, auxotrophy, tolerance to cytotoxic agents, expression of surface protein, etc., in particular, green fluorescent protein (GFP), puromycin, neomycin (Neo), hygromycin (Hyg), histidinol dehydrogenase gene (hisD), guanine phosphoribosyltransferase (Gpt) or the like. Preferably, the green fluorescent protein (GFP) and puromycin markers are used.

The composition of the present invention may include: siRNA which includes a sense RNA having at least one sequence selected from the group consisting of sequences of SEQ ID NOs: 5 to 28 in Table 1 below, and an antisense RNA having a complementary sequence thereto; and dsRNA having at least one sequence selected from the group consisting of sequences of SEQ ID NOs: 158 to 181 in Table 1 below.

In this regard, siRNA which includes a sense RNA having at least one sequence selected from the group consisting of sequences of SEQ ID NOs: 5 to 28 in Table 1 below, and an antisense RNA having a complementary sequence thereto; or dsRNA having at least one sequence selected from the group consisting of sequences of SEQ ID NOs: 158 to 181 in Table 1 below, may target variant 1 sequence (SEQ ID NO: 1) of human BANF1 gene to inhibit expression of the human BANF1 gene variant 1 through RNAi, thereby achieving effects of preventing or treating HCC.

TABLE 1

| | |
|---|---|
| Target sequence 5:<br>5'-CAA GAA GCT GGA<br>GGA AAG-3' (SEQ ID<br>NO: 482)<br>(Position in<br>gene sequence: 601) | GC content: 45.0%<br>SEQ ID NO: 5<br>Sense strand:<br>5'-CAA GAA GCU GGA GGA AAG<br>UU-3'<br>SEQ ID NO: 326<br>Antisense strand:<br>5'- CUU UCC UCC AGC UUC<br>UUG UU-3'<br>SEQ ID NO: 158<br>dsRNA:<br>5'- CAA GAA GCU GGA GGA AAG<br>UU UCU AAA G-3' |

TABLE 1-continued

| | |
|---|---|
| Target sequence 6:<br>5'-GAA AGA TGA AGA CCT CTT CC-3' (SEQ ID NO: 483) (Position in gene sequence: 667) | GC content: 40.9%<br>SEQ ID NO: 6<br>Sense strand:<br>5'-GAA AGA UGA AGA CCU CUU CCU U-3'<br>SEQ ID NO: 327<br>Antisense strand:<br>5'-GGA AGA GGU CUU CAU CU UCU U-3'<br>SEQ ID NO: 159<br>dsRNA:<br>5'- GAA AGA UGA AGA CCU CUU CCU UUC UAA AG-3' |
| Target sequence 7:<br>5'-GGA ATG GCT GAA AGA CAC TT-3' (SEQ ID NO: 484) (Position in gene sequence: 688) | GC content: 40.9%<br>SEQ ID NO: 7<br>Sense strand:<br>5'-GGA AUG GCU GAA AGA CAC UUU U-3'<br>SEQ ID NO: 328<br>Antisense strand:<br>5'-AAG UGU CUU UCA GCC AUU CCU U-3'<br>SEQ ID NO: 160<br>dsRNA:<br>5'- GGA AUG GCU GAA AGA CAC UUU UUC UAA AG-3' |
| Target sequence 8:<br>5'-CCA GTG TTC CCA GTT CCC-3' (SEQ ID NO: 485) (Position in gene sequence: 1) | GC content: 55.0%<br>SEQ ID NO: 8<br>Sense strand:<br>5'-CCA GUG UUC CCA GUU CCC UU-3'<br>SEQ ID NO: 329<br>Antisense strand:<br>5'-GGG AAC UGG GAA CAC UGG UU-3'<br>SEQ ID NO: 161<br>dsRNA:<br>5'- CCA GUG UUC CCA GUU CCC UU UCU AAA G-3' |
| Target sequence 9:<br>5'-CCA GTC AAC TGC GAG GGA-3' (SEQ ID NO: 486) (Position in gene sequence: 19) | GC content: 55.0%<br>SEQ ID NO: 9<br>Sense strand:<br>5'- CCA GUC AAC UGC GAG GGA UU-3'<br>SEQ ID NO: 330<br>Antisense strand:<br>5'-UCCUCGCAGUUGGACUGG UU-3'<br>SEQ ID NO: 162<br>dsRNA:<br>5'- CCAGUCCAACUGCGAGGA UU UCU AAA G-3' |
| Target sequence 10:<br>5'-CGA CGT GAG TCT GAG TCT-3' (SEQ ID NO: 487) (Position in gene sequence: 41) | GC content: 50.0%<br>SEQ ID NO: 10<br>Sense strand:<br>5'- CGA CGU GAG UCU GAG UCU UU-3'<br>SEQ ID NO: 331<br>Antisense strand:<br>5'-AGACUCAGACUCACGUCG UU-3'<br>SEQ ID NO: 163<br>dsRNA:<br>5'- CGACGUGAGUCUGAGUCU UU UCU AAA G-3' |
| Target sequence 11:<br>5'-GTC CGT CTT CTA ACT CTT-3' (SEQ ID NO: 488) (Position in gene sequence: 116) | GC content: 40.0%<br>SEQ ID NO: 11<br>Sense strand:<br>5'- GUC CGU CUU CUA ACU CUU UU-3'<br>SEQ ID NO: 332<br>Antisense strand:<br>5'- AAGAGUUAGAAGACGGAC UU-3'<br>SEQ ID NO: 164<br>dsRNA:<br>5'- GUCCGUCUUCUAACUCUU UU UCU AAA G-3' |
| Target sequence 12:<br>5'-CGT CAA GCC TAA GTC CTT-3' (SEQ ID NO: 489) (Position in gene sequence: 149) | GC content: 45.0%<br>SEQ ID NO: 12<br>Sense strand:<br>5'- CGUCAAGCCUAAGUCCUU UU-3'<br>SEQ ID NO: 333<br>Antisense strand:<br>5'- AAGGACUUAGGCUUGACG UU-3'<br>SEQ ID NO: 165<br>dsRNA:<br>5'- CGUCAAGCCUAAGUCCUU UU UCU AAA G-3' |
| Target sequence 13:<br>5'-GCA GAG AAA GGA AGT CCT-3' (SEQ ID NO: 490) (Position in gene sequence: 185) | GC content: 45.0%<br>SEQ ID NO: 13<br>Sense strand:<br>5'- GCAGAGAAAGGAAGUCCU UU-3'<br>SEQ ID NO: 334<br>Antisense strand:<br>5'- AGGACUUCCUUUCUCUGC UU-3'<br>SEQ ID NO: 166 dsRNA:<br>5'- GCAGAGAAAGGAAGUCCU UU UCU AAA G-3' |
| Target sequence 14:<br>5'-CGA GAA GCG AGA CCT TAG-3' (SEQ ID NO: 491) (Position in gene sequence: 234) | GC content: 50.0%<br>SEQ ID NO: 14<br>Sense strand:<br>5'- CGAGAAGCGAGACCUUAG UU-3'<br>SEQ ID NO: 335<br>Antisense strand:<br>5'-CUAAGGUCUCGCUUCUCG UU-3'<br>SEQ ID NO: 167<br>dsRNA:<br>5'- CGAGAAGCGAGACCUUAG UU UCU AAA G-3' |
| Target sequence 15:<br>5'-CCT CAA CTC TAT AGC TCT-3' (SEQ ID NO: 492) (Position in gene sequence: 319) | GC content: 40.0%<br>SEQ ID NO: 15<br>Sense strand:<br>5'- CCUCAACUCUAUAGCUCU UU-3'<br>SEQ ID NO: 336<br>Antisense strand:<br>5'-AGAGCUAUAGAGUUGAGG UU-3'<br>SEQ ID NO: 168<br>dsRNA:<br>5'- CCUCAACUCUAUAGCUCU UU UCU AAA G-3' |

TABLE 1-continued

Target sequence 16:
5'-CTA GTG GCT TGA GGT ATC-3' (SEQ ID NO: 493)
(Position in gene sequence: 423)

GC content: 45.0%
SEQ ID NO: 16
Sense strand:
5'- CUAGUGGCUUGAGGUAUC UU-3'
SEQ ID NO: 337
Antisense strand:
5'- GAUACCUCAAGCCACUAG UU-3'
SEQ ID NO: 169
dsRNA:
5'- CUAGUGGCUUGAGGUAUC UU UCU AAA G-3'

Target sequence 17:
5'-GGA TTA AGC CTG ATC A AG-3' (SEQ ID NO: 494)
(Position in gene sequence: 491)

GC content: 40.0%
SEQ ID NO: 17
Sense strand:
5'- GGAUUAAGCCUGAUCAAG UU-3'
SEQ ID NO. 338
Antisense strand:
5'-CUUGAUCAGGCUUAAUCC UU-3'
SEQ ID NO: 170
dsRNA:
5'- GGAUUAAGCCUGAUCAAG UU UCU AAA G-3'

Target sequence 18:
5'-GAC TGC TTC GGA TGC CTT-3' (SEQ ID NO: 495)
(Position in gene sequence: 734)

GC content: 50.0%
SEQ ID NO: 18
Sense strand:
5'- GACUGCUUCGGAUGCCUU UU-3'
SEQ ID NO: 339
Antisense strand:
5'-AAGGCAUCCGAAGCAGUC UU-3'
SEQ ID NO: 171
dsRNA:
5'- GACUGCUUCGGAUGCCUU UU UCU AAA G-3'

Target sequence 19:
5'-CCT TCT TGT GAT GCT CTC-3' (SEQ ID NO: 496)
(Position in gene sequence: 768)

GC content: 45.0%
SEQ ID NO: 19
Sense strand:
5'- CCUUCUUGUGAUGCUCUC UU-3'
SEQ ID NO: 340
Antisense strand:
5'- GAGAGCAUCACAAGAAGG UU-3'
SEQ ID NO: 172
dsRNA:
5'- CCUUCUUGUGAUGCUCUC UU UCU AAA G-3'

Target sequence 20:
5'-CCT CAT CCA GAG TTT GCA-3' (SEQ ID NO: 497)
(Position in gene sequence: 808)

GC content: 45.0%
SEQ ID NO: 20
Sense strand:
5'- CCUCAUCCAGAGUUUGCA UU-3'
SEQ ID NO: 341
Antisense strand:
5'-UGCAAACUCUGGAUGAGG UU-3'
SEQ ID NO: 173
dsRNA:
5'- CCUCAUCCAGAGUUUGCA UU UCU AAA G-3'

Target sequence 21:
5'-CCT GTC CTC TAC GAA GGA-3' (SEQ ID NO: 498)
(Position in gene sequence: 845)

GC content: 50.0%
SEQ ID NO: 21
Sense strand:
5'- CCUGUCCUCUACGAAGGA UU-3'
SEQ ID NO: 342
Antisense strand:
5'- UCCUUCGUAGAGGACAGG UU-3'
SEQ ID NO: 174
dsRNA:
5'- CCUGUCCUCUACGAAGGA UU UCU AAA G-3'

Target sequence 22:
5'-GAT TGC TAT TGT CGT ACT CA-3' (SEQ ID NO: 499)
(Position in gene sequence: 866)

GC content: 36.36%
SEQ ID NO: 22
Sense strand:
5'- GAUUGCUAUUGUCGUACUCA UU-3'
SEQ ID NO: 343
Antisense strand:
5'- UGAGUACGACAAUAGCAAUC UU-3'
SEQ ID NO: 175
dsRNA:
5'- sense UU UCU AAA G-3'

Target sequence 23:
5'-GGA TTC TCG CTC TTG CAT-3' (SEQ ID NO: 500)
(Position in gene sequence: 947)

GC content: 45.0%
SEQ ID NO: 23
Sense strand:
5'- GGAUUCUCGCUCUUGCAU UU-3'
SEQ ID NO: 344
Antisense strand:
5'-AUGCAAGAGCGAGAAUCC UU-3'
SEQ ID NO: 176
dsRNA:
5'- GGAUUCUCGCUCUUGCAU UU UCU AAA G-3'

Target sequence 24:
5'-GGT GAC AGT TAC CAG CTT-3' (SEQ ID NO: 501)
(Position in gene sequence: 999)

GC content: 45.0%
SEQ ID NO: 24
Sense strand:
5'- GGUGACAGUUACCAGCUU UU-3'
SEQ ID NO: 345
Antisense strand:
5'-AAGCUGGUAACUGUCACC UU-3'
SEQ ID NO: 177
dsRNA:
5'- GGUGACAGUUACCAGCUU UU UCU AAA G-3'

Target sequence 25:
5'-CCT CAC TTT CAA TCC GTT-3' (SEQ ID NO: 502)
(Position in gene sequence: 1054)

GC content: 40.0%
SEQ ID NO: 25
Sense strand:
5'- CCUCACUUUCAAUCCGUU UU-3'
SEQ ID NO: 346
Antisense strand:
5'- AACGGAUUGAAAGUGAGG UU-3'
SEQ ID NO: 178
dsRNA:
5'- CCUCACUUUCAAUCCGUU UU UCU AAA G-3'

Target sequence 26:
5'-GCA GAA CAG TCA CTG TCC-3' (SEQ ID NO: 503)
(Position in gene sequence: 1096)

GC content: 50.0%
SEQ ID NO: 26
Sense strand:
5'- GCAGAACAGUCACUGUCC UU-3'
SEQ ID NO: 347
Antisense strand:
5'- GGACAGUGACUGUUCUGC UU-3'
SEQ ID NO: 179
dsRNA:
5'- GCAGAACAGUCACUGUCC UU UCU AAA G-3'

Target sequence 27:
5'-GAT CAA TAA AGT CAG TGG CT-3' (SEQ ID NO: 504)
(Position in gene sequence: 1128)

GC content: 36.36%
SEQ ID NO: 27
Sense strand:
5'-GAUCAAUAAAGUCAGUGGCU UU-3'
SEQ ID NO: 348
Antisense strand:
5'-AGCCACUGACUUUAUUGAUC UU-3'

TABLE 1-continued

| | |
|---|---|
| | SEQ ID NO: 180<br>dsRNA:<br>5'- GAUCAAUAAAGUCAGUGGCU UU UCU AAA G-3' |
| Target sequence 28:<br>5'-AAG AAG CTG GAG GAA AGG GGT -3'<br>(SEQ IDNQ 505) | GC content: 47.83%<br>SEQ ID NO: 28<br>Sense strand:<br>5'-AAGAAGCUGGAGGAAAGGGGU UU-3'<br>SEQ ID NO: 349<br>Antisense strand:<br>5'-CCCCUUUCCUCCGCUUCUU UU-3'<br>SEQ ID NO: 181<br>dsRNA:<br>5'- AAGAAGCUGGAGGAAAGGGGU UU UCU AAA G-3' |

The composition of the present invention may include: siRNA which includes a sense RNA having at least one sequence selected from the group consisting of sequences of SEQ ID NOs: 29 to 55 in Table 2 below, and an antisense RNA having a complementary sequence thereto; or dsRNA having at least one sequence selected from the group consisting of sequences of SEQ ID NOs: 182 to 208 in Table 2 below.

In this regard, siRNA which includes a sense RNA having at least one sequence selected from the group consisting of sequences of SEQ ID NOs: 29 to 55 in Table 2 below, and an antisense RNA having a complementary sequence thereto; or dsRNA having at least one sequence selected from the group consisting of sequences of SEQ ID NOs: 182 to 208 in Table 2 below, may target variant 2 sequence (SEQ ID NO: 2) of human BANF1 gene to inhibit expression of the human BANF1 gene variant 2 through RNAi, thereby achieving effects of preventing or treating HCC.

TABLE 2

| | |
|---|---|
| Target sequence 29:<br>5'-ATG AC A ACC TCC CAA AAG CA-3' (SEQ ID NO: 506)<br>(Position in gene sequence: 452) | GC content: 40.9%<br>SEQ ID NO: 29<br>Sense strand:<br>5'-AUGACAACCUCCCAAAAGCA UU-3'<br>SEQ ID NO: 350<br>Antisense strand:<br>5'-UGCUUUUGGGAGGUUGUCAU UU-3'<br>SEQ ID NO: 182<br>dsRNA:<br>5'-AUGACAACCUCCCAAAAGCA UU UCU AAA G-3' |
| Target sequence 30:<br>5'-CCG AGA CTT CGT GGC AGA-3' (SEQ ID NO: 507)<br>(Position in gene sequence: 472) | GC content: 40.9%<br>SEQ ID NO: 30<br>Sense strand:<br>5'- CCGAGACUUCGUGGCAGA UU-3'<br>SEQ ID NO: 351<br>Antisense strand:<br>5'-UCUGCCACGAAGUCUCGG UU-3'<br>SEQ ID NO: 183<br>dsRNA<br>5'- CCGAGACUUCGUGGCAGA UU UCU AAA G-3' |
| Target sequence 31:<br>5'-AGC CTG GCT GGG ATT-3' (SEQ ID NO: 508) (Position in gene sequence: 515) | GC content: 52.94%<br>SEQ ID NO: 31<br>Sense strand:<br>5'- AGCCUGGCUGGGAUU UU-3'<br>SEQ ID NO: 352<br>Antisense strand:<br>5'- AAUCCCAGCCAGGCU UU-3'<br>SEQ ID NO: 184<br>dsRNA:<br>5'- AGCCUGGCUGGGAUU UU UCU AAA G-3' |
| Target sequence 32:5'-CAA GAA GCT GGA GGA AA-3' (SEQ ID NO: 509) (Position in gene sequence: 544) | GC content: 42.1%<br>SEQ ID NO: 32<br>Sense strand:<br>5'- CAAGAAGCUGGAGGAAA UU-3'<br>SEQ ID NO: 353<br>Antisense strand:<br>5'- UUUCCUCCAGCUUCUUG UU-3'<br>SEQ ID NO: 185<br>dsRNA:<br>5'- CAAGAAGCUGGAGGAAA UU UCU AAA G-3' |
| Target sequence 33:<br>5'-CCA GTT TCT GGT GCT AAA GA-3' (SEQ ID NO: 510) (Position in gene sequence: 592) | GC content: 40.9%<br>SEQ ID NO: 33<br>Sense strand:<br>5'-CCAGUUUCUGGUGCUAAAGA UU-3'<br>SEQ ID NO: 354<br>Antisense strand:<br>5'-UCUUUAGCACCAGAAACUGG UU-3'<br>SEQ ID NO: 186<br>dsRNA:<br>5'- CCAGUUUCUGGUGCUAAAGA UU UCU AAA G-3' |
| Target sequence 34:<br>5'-AAG ATG AAG ACC TCT TCC-3' (SEQ ID NO: 511)<br>(Position in gene sequence: 612) | GC content: 40.0%<br>SEQ ID NO: 34<br>Sense strand:<br>5'- AAGAUGAAGACCUCUUCC UU-3'<br>SEQ ID NO: 355<br>Antisense strand:<br>5'GGAAGAGGUCUUCAUCUU UU-3'<br>SEQ ID NO 187<br>dsRNA:<br>5'- AAGAUGAAGACCUCUUCC UU UCU AAA G-3' |
| Target sequence 35:<br>5'-GGA CTG CTT CGG ATG CCT T-3' (SEQ ID NO: 512)<br>(Position in gene sequence: 676) | GC content: 52.38%<br>SEQ ID NO: 35<br>Sense strand:5'-GGACUGCUUCGGAUGCCUU UU-3'<br>SEQ ID NO: 356<br>Antisense strand:<br>5'-AAGGCAUCCGAAGCAGUCC UU-3'<br>SEQ ID NO: 188<br>dsRNA:<br>5'- GGACUGCUUCGGAUGCCUU UU UCU AAA G-3' |
| Target sequence 36:<br>5'-AGT GGT GCG ACG CCT TCT T-3' (SEQ ID NO: 513)<br>(Position in gene sequence: 698) | GC content: 52.38%<br>SEQ ID NO: 36<br>Sense strand:<br>5'-AGUGGUGCGACGCCUUCUU UU-3'<br>SEQ ID NO: 357<br>Antisense strand:<br>5'-AAGAAGGCGUCGCACCACU UU-3' |

TABLE 2-continued

| | |
|---|---|
| | SEQ ID NO: 189<br>dsRNA:<br>5'- AGUGGUGCGACGCCUUCUU UU UU UCU AAA G-3' |
| Target sequence 37:<br>5'-CTC TCT GGG AAG CTC TCA AT-3'<br>(SEQ ID NO: 514)<br>(Position in gene sequence: 724) | GC content: 52.38%<br>SEQ ID NO: 37<br>Sense strand:<br>5'-AGUGGUGCGACGCCUUCUU UU-3'<br>SEQ ID NO: 358<br>Antisense strand:<br>5'-AAGAAGGCGUCGCACCACU UU-3'<br>SEQ ID NO: 190<br>dsRNA:<br>5'- AGUGGUGCGACGCCUUCUU UU UCU AAA G-3' |
| Target sequence 38: 5'-TTG CTA TTG TCG TAC TCA CC-3'<br>(SEQ ID NO: 515)<br>(Position in gene sequence: 811) | GC content: 40.9%<br>SEQ ID NO: 38<br>Sense strand:<br>5'-UUGCUAUUGUCGUACUCACC UU-3'<br>SEQ ID NO: 359<br>Antisense strand:<br>5'-GGUGAGUACGACAAUAGCAA UU-3'<br>SEQ ID NO: 191<br>dsRNA:<br>5'- UUGCUAUUGUCGUACUCACC UU UCU AAA G-3' |
| Target sequence 39:<br>5'-GAT TCT CGC TCT TGC ATG-3' (SEQ ID NO: 516)<br>(Position in gene sequence: 891) | GC content: 45.0%<br>SEQ ID NO: 39<br>Sense strand:<br>5'- GAUUCUCGCUCUUGCAUG UU-3'<br>SEQ ID NO: 360<br>Antisense strand:<br>5'-CAUGCAAGAGCGAGAAUC UU-3'<br>SEQ ID NO: 192<br>dsRNA:<br>5'- GAUUCUCGCUCUUGCAUG UU UCU AAA G-3' |
| Target sequence 40:<br>5'-CAG TTC CCT GGT GAC AGT TA-3' (SEQ ID NO: 517)<br>(Position in gene sequence: 933) | GC content: 45.45%<br>SEQ ID NO: 40<br>Sense strand:<br>5'-CAGUUCCCUGGUGACAGUUA UU-3'<br>SEQ ID NO: 361<br>Antisense strand:5'-UAACUGUCACCAGGGAACUG UU-3'<br>SEQ ID NO: 193<br>dsRNA:<br>5'- CAGUUCCCUGGUGACAGUUA UU UCU AAA G-3' |
| Target sequence 41:<br>5'-CCA GCT TTC CTG AAT GGA-3' (SEQ ID NO: 518)<br>(Position in gene sequence: 953) | GC content: 45.0%<br>SEQ ID NO: 41<br>Sense strand:<br>5'- CCAGCUUUCCUGAAUGGA UU-3'<br>SEQ ID NO: 362<br>Antisense strand: 5'-UCCAUUCAGGAAAGCUGG UU-3'<br>SEQ ID NO: 194<br>dsRNA:<br>5'- CCAGCUUUCCUGAAUGGA UU UCU AAA G-3' |
| Target sequence 42:<br>5'-CTC ACT TTC AAT CCG TTT GA-3' (SEQ ID NO: 519) | GC content: 36.36%<br>SEQ ID NO: 42<br>Sense strand:<br>5'-CUCACUUUCAAUCCGUUUGA UU-3'<br>SEQ ID NO: 363<br>Antisense strand:<br>5'-UCAAACGGAUUGAAAGGAG UU-3'<br>SEQ ID NO: 195<br>dsRNA:<br>5'- CUCACUUUCAAUCCGUUUGA UU UCU AAA G-3' |
| Target sequence 43:<br>5'-CAG AAC AGT CAC TGT CCT TG-3' (SEQ ID NO: 520)<br>(Position in gene sequence: 1039) | GC content: 45.45%<br>SEQ ID NO: 43<br>Sense strand:<br>5'-CAGAACAGUCACUGUCCUUG UU-3'<br>SEQ ID NO: 364<br>Antisense strand:<br>5'-CAAGGACAGUGACUGUUCUG UU-3'<br>SEQ ID NO 196<br>dsRNA:<br>5'- CAGAACAGUCACUGUCCUUG UU UCU AAA G-3' |
| Target sequence 44:<br>5'-CAC CAG TCC AAC TGC GAG-3' (SEQ ID NO: 521)<br>(Position in gene sequence: 8) | GC content: 55.0%<br>SEQ ID NO: 44<br>Sense strand:<br>5'- CACCAGUCCAACUGCGAG UU-3'<br>SEQ ID NO: 365<br>Antisense strand:<br>5'-CUCGCAGUUGGACUGGUG UU-3'<br>SEQ ID NO: 197<br>dsRNA:<br>5'- CACCAGUCCAACUGCGAG UU UCU AAA G-3' |
| Target sequence 45: 5'-TGC GAC GTG AGT CTG AGT CT-3' (SEQ ID NO: 522) (Position in gene sequence: 39) | GC content: 50.0%<br>SEQ ID NO: 45<br>Sense strand:<br>5'-UGCGACGUGAGUCUGAGUCU UU-3'<br>SEQ ID NO: 366<br>Antisense strand:<br>5'-AGACUCAGACUCACGUCGCA UU-3'<br>SEQ ID NO: 198<br>dsRNA:<br>5'- UGCGACGUGAGUCUGAGUCU UU UCU AAA G-3' |
| Target sequence 46: 5'-CCT CCG AAA ACC GTA CTT-3' (SEQ ID NO: 523) (Position in gene sequence: 63) | GC content: 45.0%<br>SEQ ID NO: 46<br>Sense strand:<br>5'- CCUCCGAAAACCGUACUU UU-3'<br>SEQ ID NO: 367<br>Antisense strand:<br>5'-AAGUACGGUUUUCGGAGG UU-3'<br>SEQ ID NO: 199<br>dsRNA:<br>5'- CCUCCGAAAACCGUACUU UU UCU AAA G-3' |
| Target sequence 47:<br>5'-CCT TGT CCG TCT TCT AAC TC-3' (SEQ ID NO: 524)<br>(Position in gene sequence: 113) | GC content: 45.45%<br>SEQ ID NO: 47<br>Sense strand:<br>5'-CCUUGUCCGUCUUCUAACUC UU-3'<br>SEQ ID NO: 368<br>Antisense strand:<br>5'-GAGUUAGAAGACGGACAAGG UU-3'<br>SEQ ID NO: 200<br>dsRNA:<br>5'- CCUUGUCCGUCUUCUAACUC UU UCU AAA G-3' |
| Target sequence 48:<br>5'-CCA GGT CCG TCA AGC CTA A-3' (SEQ ID NO: 525) | GC content: 52.38%<br>SEQ ID NO: 48<br>Sense strand:<br>5'-CCAGGUCCGUCAAGCCUAA |

TABLE 2-continued

| | |
|---|---|
| (Position in gene sequence: 142) | UU-3'<br>SEQ ID NO. 369<br>Antisense strand:<br>5'-UUAGGCUUGACGGACCUGG UU-3'<br>SEQ ID NO: 201<br>dsRNA:<br>5'- CCAGGUCCGUCAAGCCUAA UU UCU AAA G-3' |
| Target sequence 49:<br>5'-GCA GCA GAG AAA GGA AGT-3' (SEQ ID NO: 526)<br>(Position in gene sequence: 182) | GC content: 45.0%<br>SEQ ID NO 49<br>Sense strand:<br>5'- GCAGCAGAGAAAGGAAGU UU-3'<br>SEQ ID NO: 370<br>Antisense strand:<br>5'-UACUUCCUUUCUCUGCUGC UU-3'<br>SEQ ID NO: 202<br>dsRNA:<br>5'- GCAGCAGAGAAAGGAAGU UU UCU AAA G-3' |
| Target sequence 50:<br>5'-CCT ATC TCC CTC AGA ACT-3' (SEQ ID NO: 527)<br>(Position in gene sequence: 214) | GC content: 45.0%<br>SEQ ID NO: 50<br>Sense strand:<br>5'- CCUAUCUCCCUCAGAACU UU-3'<br>SEQ ID NO: 371<br>Antisense strand:<br>5'-AGUUCUGAGGGAGAUAGG UU-3'<br>SEQ ID NO: 203<br>dsRNA:<br>5'- CCUAUCUCCCUCAGAACU UU UCU AAA G-3' |
| Target sequence 51:<br>5'-GAG AAG CGA GAC CTT AGA AG-3' (SEQ ID NO: 528)<br>(Position in gene sequence: 236) | GC content: 45.45%<br>SEQ ID NO: 51<br>Sense strand:<br>5'-GAGAAGCGAGACCUUAGAAG UU-3'<br>SEQ ID NO: 372<br>Antisense strand:<br>5'-CUUCUAAGGUCUCGCUUCUC UU-3'<br>SEQ ID NO: 204<br>dsRNA:<br>5'- GAGAAGCGAGACCUUAGAAG UU UCU AAA G-3' |
| Target sequence 52:<br>5'-GCC TCA ACT CTA TAG CTC TA-3' (SEQ ID NO: 529)<br>(Position in gene sequence: 319) | GC content: 40.9%<br>SEQ ID NO: 52<br>Sense strand:<br>5'-GCCUCAACUCUAUAGCUCUA UU-3'<br>SEQ ID NO: 373<br>Antisense strand:<br>5'-UAGAGCUAUAGAGUUGAGGC UU-3'<br>SEQ ID NO: 205<br>dsRNA:<br>5'- GCCUCAACUCUAUAGCUCUA UU UCU AAA G-3' |
| Target sequence 53:<br>5'-CCA ACG TGG AAT GTT TCT-3' (SEQ ID NO: 530)<br>(Position in gene sequence: 354) | GC content: 40.0%<br>SEQ ID NO: 53<br>Sense strand:<br>5'- CCAACGUGGAAUGUUUCU UU-3'<br>SEQ ID NO: 374<br>Antisense strand:<br>5'-AGAAACAUUCCACGUUGG UU-3'<br>SEQ ID NO 206<br>dsRNA:<br>5'- CCAACGUGGAAUGUUUCU UU UCU AAA G-3' |
| Target sequence 54:<br>5'-GAA GCG GAA GTG GAA GAA AGT T-3' (SEQ ID NO: 531)<br>(Position in gene sequence: 401) | GC content: 41.67%<br>SEQ ID NO: 54<br>Sense strand:<br>5'-GAAGCGGAAGUGGAAGAAAGUU UU-3'<br>SEQ ID NO: 375<br>Antisense strand:<br>5'-AACUUUCUUCCACUUCCGCUUC UU-3'<br>SEQ ID NO: 207<br>dsRNA:<br>5'-GAAGCGGAAGUGGAAGAAAGUU UU UCU AAA G-3' |
| Target sequence 55:<br>5'-CTA GTG GCT TGA GAT TAA GC-3' (SEQ ID NO: 532)<br>(Position in gene sequence: 423) | GC content: 40.9%<br>SEQ ID NO: 55<br>Sense strand:<br>5'-CUAGUGGCUUGAGAUUAAGC UU-3'<br>SEQ ID NO: 376<br>Antisense strand:<br>5'-GCUUAAUCUCAAGCCACUAG UU-3'<br>SEQ ID NO: 208<br>dsRNA:<br>5'- CUAGUGGCUUGAGAUUAAGC UU UCU AAA G-3' |

The composition of the present invention may include: siRNA which includes a sense RNA having at least one sequence selected from the group consisting of sequences of SEQ ID NOs: 56 to 120 in Table 3 below, and an antisense RNA having a complementary sequence thereto; or dsRNA having at least one sequence selected from the group consisting of sequences of SEQ ID NOs: 209 to 273 in Table 3 below.

In this regard, siRNA which includes a sense RNA having at least one sequence selected from the group consisting of sequences of SEQ ID NOs: 56 to 120 in Table 3 below, and an antisense RNA having a complementary sequence thereto; or dsRNA having at least one sequence selected from the group consisting of sequences of SEQ ID NOs: 209 to 273 in Table 3 below, may target a sequence of human PLOD3 gene (SEQ ID NO: 3) to inhibit expression of the human PLOD3 gene through RNAi, thereby achieving effects of preventing or treating HCC.

TABLE 3

| | |
|---|---|
| Target sequence 56: 5'-CCA GAG AAG CTG CTG GTG AT-3' (SEQ ID NO: 533) (Position in gene sequence: 562) | GC content: 50.0%<br>SEQ ID NO: 56 Sense strand: 5'-CCAGAGAAGCUGCUGGUGAU UU-3'<br>SEQ ID NO: 377 Antisense strand: 5'-AUCACCAGCAGCUUCUCUGG UU-3'<br>SEQ ID NO: 209 dsRNA: 5'-CCAGAGAAGCUGCUGGUGAU UU UCU AAA G-3' |

TABLE 3-continued

| Target sequence 57: 5'-CCA CAG CTG AAA CCG AGG-3' (SEQ ID NO: 534) (Position in gene sequence: 590) | GC content: 55.0%<br>SEQ ID NO: 57 Sense strand: 5'-CCACAGCUGAAACCGAGG UU-3'<br>SEQ ID NO: 378 Antisense strand: 5'-CCUCGGUUUCAGCUGUGG UU-3'<br>SEQ ID NO: 210 dsRNA: 5'-CCACAGCUGAAACCGAGG UU UCU AAA G-3' |
|---|---|
| Target sequence 58: 5'-CTC TGC GGA GTT CTT C-3' (SEQ ID NO: 535) (Position in gene sequence: 627) | GC content: 50.0%<br>SEQ ID NO: 58 Sense strand: 5'-CUCUGCGGAGUUCUUC UU-3'<br>SEQ ID NO: 379 Antisense strand: 5'-GAAGAACUCCGCAGAG UU-3'<br>SEQ ID NO: 211 dsRNA: 5'-CUCUGCGGAGUUCUUC UU UCU AAA G-3' |
| Target sequence 59: 5'-AAC TAC ACT GTG CGG ACC-3' (SEQ ID NO: 536) (Position in gene sequence: 643) | GC content: 50.0%<br>SEQ ID NO: 59 Sense strand: 5'-AACUACACUGUGCGGACC UU-3'<br>SEQ ID NO: 380 Antisense strand: 5'-GGUCCGCACAGUGUAGUU UU-3'<br>SEQ ID NO: 212 dsRNA: 5'-AACUACACUGUGCGGACC UU UCU AAA G-3' |
| Target sequence 60: 5'-GTG ATG TGG CTC GAA CAG-3' (SEQ ID NO: 537) (Position in gene sequence: 689) | GC content: 50.0%<br>SEQ ID NO: 60 Sense strand: 5'-GUGAUGUGGCUCGAACAG UU-3'<br>SEQ ID NO: 381 Antisense strand:5'-CUGUUCGAGCCACAUCAC UU-3'<br>SEQ ID NO: 213 dsRNA: 5'-GUGAUGUGGCUCGAACAG UU UCU AAA G-3' |
| Target sequence 61: 5'-GGT TAA AGA AGG AAA TGG AG-3' (SEQ ID NO: 538) (Position in gene sequence: 731) | GC content: 36.36%<br>SEQ ID NO: 61 Sense strand: 5'-GGUUAAAGAAGGAAAUGGAG UU-3'<br>SEQ ID NO: 382 Antisense strand: 5'-CUCCAUUUCCUUCUUUAACC UU-3'<br>SEQ ID NO: 214 dsRNA: 5'-GGUUAAAGAAGGAAAUGGAG UU UCU AAA G-3' |
| Target sequence 62: 5'-GGA GGA TAT GAT CAT CAT GT-3' (SEQ ID NO: 539) (Position in gene sequence: 765) | GC content: 36.36%<br>SEQ ID NO: 62 Sense strand: 5'-GGAGGAUAUGAUCAUCAUGU UU-3'<br>SEQ ID NO: 383 Antisense strand: 5'-ACAUGAUGAUCAUAUCCUCC UU-3'<br>SEQ ID NO: 215 dsRNA: 5'-GGAGGAUAUGAUCAUCAUGU UU UCU AAA G-3' |
| Target sequence 63: 5'-GGA TAG CTA CGA CGT GAT-3' (SEQ ID NO: 540) (Position in gene sequence: 789) | GC content: 45.0%<br>SEQ ID NO: 63 Sense strand: 5'-GGAUAGCUACGACGUGAU UU-3'<br>SEQ ID NO: 384 Antisense strand: 5'-AUCACGUCGUAGCUAUCC UU-3'<br>SEQ ID NO: 216 dsRNA: 5'-GGAUAGCUACGACGUGAU UU UCU AAA G-3' |
| Target sequence 64: 5'-CAC AGA GCT GCT GAA GAA-3' (SEQ ID NO: 541) (Position in gene sequence: 822) | GC content: 45.0%<br>SEQ ID NO: 64 Sense strand: 5'-CACAGAGCUGCUGAAGAA UU-3'<br>SEQ ID NO: 385 Antisense strand: 5'-UUCUUCAGCAGCUCUGUG UU-3'<br>SEQ ID NO: 217 dsRNA: 5'-CACAGAGCUGCUGAAGAA UU UCU AAA G-3' |
| Target sequence 65: 5'-TGC TCT TCT CTG CAG AGA-3' (SEQ ID NO: 542) (Position in gene sequence: 863) | GC content: 45.0%<br>SEQ ID NO: 65 Sense strand: 5'-UGCUCUUCUCUGCAGAGA UU-3'<br>SEQ ID NO: 386 Antisense strand: 5'-UCUCUGCAGAGAAGAGCA UU-3'<br>SEQ ID NO: 218 dsRNA: 5'-UGCUCUUCUCUGCAGAGA UU UCU AAA G-3' |
| Target sequence 66: 5'-GCT TCC TCA ATT CTG GTG G-3' (SEQ ID NO: 543) (Position in gene sequence: 941) | GC content: 47.62%<br>SEQ ID NO: 66 Sense strand: 5'-GCUUCCUCAAUUCUGGUGG UU-3'<br>SEQ ID NO: 387 Antisense strand: 5'-CCACCAGAAUUGAGGAAGC UU-3'<br>SEQ ID NO: 219 dsRNA: 5'-GCUUCCUCAAUUCUGGUGG UU UCU AAA G-3' |

TABLE 3-continued

| | |
|---|---|
| Target sequence 67: 5'-ATT CAT CGG TTT TGC CAC CA-3' (SEQ ID NO: 544) (Position in gene sequence: 950) | GC content: 40.9%<br>SEQ ID NO: 67 Sense strand: 5'-AUUCAUCGGUUUUGCCACCA UU-3'<br>SEQ ID NO: 388 Antisense strand: 5'-UGGUGGCAAAACCGAUGAAU UU-3'<br>SEQ ID NO: 220 dsRNA: 5'-AUUCAUCGGUUUUGCCACCA UU UCU AAA G-3' |
| Target sequence 68: 5'-AGT GGA AGT ACA AGG ATG A-3' (SEQ ID NO: 545) (Position in gene sequence: 1001) | GC content: 38.1%<br>SEQ ID NO: 68 Sense strand: 5'-AGUGGAAGUACAAGGAUGA UU-3'<br>SEQ ID NO: 389 Antisense strand: 5'-UCAUCCUUGUACUUCCACU UU-3'<br>SEQ ID NO: 221 dsRNA: 5'-AGUGGAAGUACAAGGAUGA UU UCU AAA G-3' |
| Target sequence 69: 5'-CAG CCT TAA TCT GGA TCA-3' (SEQ ID NO: 546) (Position in gene sequence: 1080) | GC content: 40.0%<br>SEQ ID NO: 69 Sense strand: 5'-CAGCCUUAAUCUGGAUCA UU-3'<br>SEQ ID NO: 390 Antisense strand: 5'-UGAUCCAGAUUAAGGCUG UU-3'<br>SEQ ID NO: 222 dsRNA: 5'-CAGCCUUAAUCUGGAUCA UU UCU AAA G-3' |
| Target sequence 70: 5'-GTC TCG GAT CTT TCA GAA CC-3' (SEQ ID NO: 547) (Position in gene sequence: 1101) | GC content: 45.45%<br>SEQ ID NO: 70 Sense strand: 5'-GUCUCGGAUCUUUCAGAACC UU-3'<br>SEQ ID NO: 391 Antisense strand: 5'-GGUUCUGAAAGAUCCGAGAC UU-3'<br>SEQ ID NO: 223 dsRNA: 5'-GUCUCGGAUCUUUCAGAACC UU UCU AAA G-3' |
| Target sequence 71: 5'-GGC TTT AGA TGA AGT GGT-3' (SEQ ID NO: 548) (Position in gene sequence: 1128) | GC content: 40.0%<br>SEQ ID NO: 71 Sense strand: 5'-GGCUUUAGAUGAAGUGGU UU-3'<br>SEQ ID NO: 392 Antisense strand: 5'-ACCACUUCAUCUAAAGCC UU-3'<br>SEQ ID NO: 224 dsRNA: 5'-GGCUUUAGAUGAAGUGGU UU UCU AAA G-3' |
| Target sequence 72: 5'-GTT TGA TCG GAA CCG TGT-3' (SEQ ID NO: 549) (Position in gene sequence: 1152) | GC content: 45.0%<br>SEQ ID NO: 72 Sense strand: 5'-GUUUGAUCGGAACCGUGU UU-3'<br>SEQ ID NO: 393 Antisense strand: 5'-ACACGGUUCCGAUCAAAC UU-3'<br>SEQ ID NO: 225 dsRNA: 5'-GUUUGAUCGGAACCGUGU UU UCU AAA G-3' |
| Target sequence 73: 5'-TTG TGG TCC ATG GAA ACG-3' (SEQ ID NO: 550) (Position in gene sequence: 1205) | GC content: 45.0%<br>SEQ ID NO: 73 Sense strand: 5'-UUGUGGUCCAUGGAAACG UU-3'<br>SEQ ID NO: 394 Antisense strand: 5'-CGUUUCCAUGGACCACAA UU-3'<br>SEQ ID NO: 226 dsRNA: 5'-UUGUGGUCCAUGGAAACG UU UCU AAA G-3' |
| Target sequence 74: 5'-CCA CTA AGC TGC AGC TCA A-3' (SEQ ID NO: 551) (Position in gene sequence: 1223) | GC content: 47.62%<br>SEQ ID NO: 74 Sense strand: 5'-CCACUAAGCUGCAGCUCAA UU-3'<br>SEQ ID NO: 395 Antisense strand: 5'-UUGAGCUGCAGCUUAGUGG UU-3'<br>SEQ ID NO: 227 dsRNA: 5'-CCACUAAGCUGCAGCUCAA UU UCU AAA G-3' |
| Target sequence 75: 5'-CCA ATG GCT GGA CTC CTG A-3' (SEQ ID NO: 552) (Position in gene sequence: 1265) | GC content: 52.38%<br>SEQ ID NO: 75 Sense strand: 5'-CCAAUGGCUGGACUCCUGA UU-3'<br>SEQ ID NO: 396 Antisense strand: 5'-TCAGGAGTCCAGCCATTGG UU-3'<br>SEQ ID NO: 228 dsRNA: 5'-CCAAUGGCUGGACUCCUGA UU UCU AAA G-3' |
| Target sequence 76: 5'-GCT GTG GCT TCT GCA ACC A-3' (SEQ ID NO: 553) (Position in gene sequence: 1289) | GC content: 52.38%<br>SEQ ID NO: 76 Sense strand: 5'-GCUGUGGCUUCUGCAACCA UU-3'<br>SEQ ID NO: 397 Antisense strand: 5'-UGGUUGCAGAAGCCACAGC UU-3'<br>SEQ ID NO: 229 dsRNA: 5'-GCUGUGGCUUCUGCAACCA UU UCU AAA G-3' |

TABLE 3-continued

| | |
|---|---|
| Target sequence 77: 5'-GTG TTT GTG AAC AG CCT-3' (SEQ ID NO: 554) (Position in gene sequence: 1360) | GC content: 45.0%<br>SEQ ID NO: 77 Sense strand: 5'-GUGUUUGUGGAACAGCCU UU-3'<br>SEQ ID NO: 398 Antisense strand: 5'-AGGCUGUUCCACAAACAC UU-3'<br>SEQ ID NO: 230 dsRNA: 5'-GUGUUUGUGGAACAGCCU UU UCU AAA G-3' |
| Target sequence 78: 5'-GCT GCT ACT CCT GGA CTA T-3' (SEQ ID NO: 555) (Position in gene sequence: 1407) | GC content: 47.62%<br>SEQ ID NO: 78 Sense strand: 5'-GCUGCUACUCCUGGACUAU UU-3'<br>SEQ ID NO: 399 Antisense strand: 5'-AUAGUCCAGGAGUAGCAGC UU-3'<br>SEQ ID NO: 231 dsRNA: 5'-GCUGCUACUCCUGGACUAU UU UCU AAA G-3' |
| Target sequence 79: 5'-TTC CTG CAC AAC AAC GAG GT-3' (SEQ ID NO: 556) (Position in gene sequence: 1447) | GC content: 45.45%<br>SEQ ID NO: 79 Sense strand: 5'-UUCCUGCACAACAACGAGGU UU-3'<br>SEQ ID NO: 400 Antisense strand: 5'-ACCUCGUUGUUGUGCAGGAA UU-3'<br>SEQ ID NO: 232 dsRNA: 5'-UUCCUGCACAACAACGAGGU UU UCU AAA G-3' |
| Target sequence 80: 5'-CCA CAT CGC TGA CTC CTG-3' (SEQ ID NO: 557) (Position in gene sequence: 1479) | GC content: 55.0%<br>SEQ ID NO: 80 Sense strand: 5'-CCACAUCGCUGACUCCUG UU-3'<br>SEQ ID NO: 401 Antisense strand: 5'-CAGGAGUCAGCGAUGUGG UU-3'<br>SEQ ID NO: 233 dsRNA: 5'-CCACAUCGCUGACUCCUG UU UCU AAA G-3' |
| Target sequence 81: 5'-AGC TCC AGG ACC ACT TCT CA-3' (SEQ ID NO: 558) (Position in gene sequence: 1502) | GC content: 50.0%<br>SEQ ID NO: 81 Sense strand: 5'-AGCUCCAGGACCACUUCUCA UU-3'<br>SEQ ID NO: 402 Antisense strand: 5'-TGAGAAGTGGTCCTGGAGCT UU-3'<br>SEQ ID NO: 234 dsRNA: 5'-AGCUCCAGGACCACUUCUCA UU UCU AAA G-3' |
| Target sequence 82: 5'-ATG GCC ATG GAC CTG TGT-3' (SEQ ID NO: 559) (Position in gene sequence: 1576) | GC content: 50.0%<br>SEQ ID NO: 82 Sense strand: 5'-AUGGCCAUGGACCUGUGU UU-3'<br>SEQ ID NO: 403 Antisense strand: 5'-ACACAGGUCCAUGGCCAU UU-3'<br>SEQ ID NO: 235 dsRNA: 5'-AUGGCCAUGGACCUGUGU UU UCU AAA G-3' |
| Target sequence 83: 5'-CGA GTG TGA GTT CTA CTT CA-3' (SEQ ID NO: 560) (Position in gene sequence: 1605) | GC content: 40.9%<br>SEQ ID NO: 83 Sense strand: 5'-CGAGUGUGAGUUCUACUUCA UU-3'<br>SEQ ID NO: 404 Antisense strand:5'-UGAAGUAGAACUCACACUCG UU-3'<br>SEQ ID NO: 236 dsRNA: 5'-CGAGUGUGAGUUCUACUUCA UU UCU AAA G-3' |
| Target sequence 84: 5'-GCT GTC CTC ACC AAC CTG-3' (SEQ ID NO: 561) (Position in gene sequence: 1639) | GC content: 55.0%<br>SEQ ID NO: 84 Sense strand: 5'-GCUGUCCUCACCAACCUG UU-3'<br>SEQ ID NO: 405 Antisense strand: 5'-CAGGUUGGUGAGGACAGC UU-3'<br>SEQ ID NO: 237 dsRNA: 5'-GCUGUCCUCACCAACCUG UU UCU AAA G-3' |
| Target sequence 85: 5'-CTG CGT ATC CTC ATT GAG-3' (SEQ ID NO: 562) (Position in gene sequence: 1663) | GC content: 45.0%<br>SEQ ID NO: 85 Sense strand: 5'-CUGCGUAUCCUCAUUGAG UU-3'<br>SEQ ID NO: 406 Antisense strand: 5'-CUCAAUGAGGAUACGCAG UU-3'<br>SEQ ID NO: 238 dsRNA: 5'-CUGCGUAUCCUCAUUGAG UU UCU AAA G-3' |
| Target sequence 86: 5'-GAG AAC AGG AAG GTG ATC-3' (SEQ ID NO: 563) (Position in gene sequence: 1681) | GC content: 45.0%<br>SEQ ID NO: 86 Sense strand: 5'-GAGAACAGGAAGGUGAUC UU-3'<br>SEQ ID NO: 407 Antisense strand: 5'-GAUCACCUUCCUGUUCUC UU-3'<br>SEQ ID NO: 239 dsRNA: 5'-GAGAACAGGAAGGUGAUC UU UCU AAA G-3' |

TABLE 3-continued

| Target sequence 87: 5'-CAA GCT GTG GTC CAA CTT-3' (SEQ ID NO: 564) (Position in gene sequence: 1722) | GC content: 45.0%<br>SEQ ID NO: 87 Sense strand: 5'-CAAGCUGUGGUCCAACUU UU-3'<br>SEQ ID NO: 408 Antisense strand: 5'-AAGUUGGACCACAGCUUG UU-3'<br>SEQ ID NO: 240 dsRNA: 5'-CAAGCUGUGGUCCAACUU UU UCU AAA G-3' |
|---|---|
| Target sequence 88: 5'-GAG GAC TAC GTG GAG CTG-3' (SEQ ID NO: 565) (Position in gene sequence: 1780) | GC content: 55.0%<br>SEQ ID NO: 88 Sense strand: 5'-GAGGACUACGUGGAGCUG UU-3'<br>SEQ ID NO: 409 Antisense strand: 5'-CAGCUCCACGUAGUCCUC UU-3'<br>SEQ ID NO: 241 dsRNA: 5'-GAGGACUACGUGGAGCUG UU UCU AAA G-3' |
| Target sequence 89: 5'-GTG TGT GGA ATG TAC CAT AC-3' (SEQ ID NO: 566) (Position in gene sequence: 1817) | GC content: 40.9%<br>SEQ ID NO: 89 Sense strand: 5'-GUGUGUGGAAUGUACCAUAC UU-3'<br>SEQ ID NO: 410 Antisense strand: 5'-GUAUGGUACAUUCCACACAC UU-3'<br>SEQ ID NO: 242 dsRNA: 5'-GUGUGUGGAAUGUACCAUAC UU UCU AAA G-3' |
| Target sequence 90: 5'-AGA GGG ATG TGT TCT CGG G-3' (SEQ ID NO: 567) (Position in gene sequence: 1888) | GC content: 52.38%<br>SEQ ID NO: 90 Sense strand: 5'-AGAGGGAUGUGUUCUCGGG UU-3'<br>SEQ ID NO: 411 Antisense strand: 5'-CCCGAGAACACAUCCCUCU UU-3'<br>SEQ ID NO: 243 dsRNA: 5'-AGAGGGAUGUGUUCUCGGG UU UCU AAA G-3' |
| Target sequence 91: 5'-CCT TCT GTA AGA GCT TTC GA-3' (SEQ ID NO: 568) (Position in gene sequence: 1931) | GC content: 40.9%<br>SEQ ID NO: 91 Sense strand: 5'-CCUUCUGUAAGAGCUUUCGA UU-3'<br>SEQ ID NO: 412 Antisense strand: 5'-UCGAAAGCUCUUACAGAAGG UU-3'<br>SEQ ID NO: 244 dsRNA: 5'-CCUUCUGUAAGAGCUUUCGA UU UCU AAA G-3' |
| Target sequence 92: 5'-ACA AGG GCA TCT TCC TCC AT-3' (SEQ ID NO: 569) (Position in gene sequence: 1952) | GC content: 45.45%<br>SEQ ID NO: 92 Sense strand: 5'-ACAAGGGCAUCUUCCUCCAU UU-3'<br>SEQ ID NO: 413 Antisense strand: 5'-AUGGAGGAAGAUGCCCUUGU UU-3'<br>SEQ ID NO: 245 dsRNA: 5'-ACAAGGGCAUCUUCCUCCAU UU UCU AAA G-3' |
| Target sequence 93: 5'-CTG AGC AAT CAG CAT GAA-3' (SEQ ID NO: 570) (Position in gene sequence: 1972) | GC content: 40.0%<br>SEQ ID NO: 93 Sense strand: 5'-CUGAGCAAUCAGCAUGAA UU-3'<br>SEQ ID NO: 414 Antisense strand: 5'-UUCAUGCUGAUUGCUCAG UU-3'<br>SEQ ID NO: 246 dsRNA: 5'-CUGAGCAAUCAGCAUGAAUU UCU AAA G-3' |
| Target sequence 94: 5'-CCA CTT CCA GAT ACG ACA-3' (SEQ ID NO: 571) (Position in gene sequence: 2006) | GC content: 45.0%<br>SEQ ID NO: 94 Sense strand: 5'-CCACUUCCAGAUACGACA UU-3'<br>SEQ ID NO: 415 Antisense strand: 5'-UGUCGUAUCUGGAAGUGG UU-3'<br>SEQ ID NO: 247 dsRNA: 5'-CCACUUCCAGAUACGACA UU UCU AAA G-3' |
| Target sequence 95: 5'-ACC TCT GGC AGA TCT TCG A-3' (SEQ ID NO: 572) (Position in gene sequence: 2042) | GC content: 47.62%<br>SEQ ID NO: 95 Sense strand: 5'-ACCUCUGGCAGAUCUUCGA UU-3'<br>SEQ ID NO: 416 Antisense strand: 5'-UCGAAGAUCUGCCAGAGGU UU-3'<br>SEQ ID NO: 248 dsRNA: 5'-ACCUCUGGCAGAUCUUCGA UU UCU AAA G-3' |
| Target sequence 96: 5'-CGT CGA CTG GAA GGA GCA-3' (SEQ ID NO: 573) (Position in gene sequence: 2067) | GC content: 55.0%<br>SEQ ID NO: 96 Sense strand: 5'-CGUCGACUGGAAGGAGCA UU-3'<br>SEQ ID NO: 417 Antisense strand: 5'-UGCUCCUUCCAGUCGACG UU-3'<br>SEQ ID NO: 249 dsRNA: 5'-CGUCGACUGGAAGGAGCA UU UCU AAA G-3' |

TABLE 3-continued

| Target sequence 97: 5'-GTA CAT CCA CGA GAA CTA-3' (SEQ ID NO: 574) (Position in gene sequence: 2085) | GC content: 40.0%<br>SEQ ID NO: 97 Sense strand: 5'-GUACAUCCACGAGAACUA UU-3'<br>SEQ ID NO: 418 Antisense strand: 5'-UAGUUCUCGUGGAUGUAC UU-3'<br>SEQ ID NO: 250 dsRNA: 5'-GUACAUCCACGAGAACUA UU UCU AAA G-3' |
| --- | --- |
| Target sequence 98 5'-AAG GAA TCG TGG AGC AGC CA-3' (SEQ ID NO: 575) (Position in gene sequence: 2123) | GC content: 50.0%<br>SEQ ID NO: 98 Sense strand: 5'-AAGGAAUCGUGGAGCAGCCA UU-3'<br>SEQ ID NO: 419 Antisense strand: 5'-UGGCUGCUCCACGAUUCCUU UU-3'<br>SEQ ID NO: 251 dsRNA: 5'-AAGGAAUCGUGGAGCAGCCA UU UCU AAA G-3' |
| Target sequence 99 5'-CTG CTG TCA GAA CAA ATG-3' (SEQ ID NO: 576) (Position in gene sequence: 2167) | GC content: 40.0%<br>SEQ ID NO: 99 Sense strand: 5'-CUGCUGUCAGAACAAAUG UU-3'<br>SEQ ID NO: 420 Antisense strand: 5'-CAUUUGUUCUGACAGCAG UU-3'<br>SEQ ID NO: 252 dsRNA: 5'-CUGCUGUCAGAACAAAUG UU UCU AAA G-3' |
| Target sequence 100: 5'-TGT GAT GAG CTG GTG GCA GA-3' (SEQ ID NO: 577) (Position in gene sequence: 2185) | GC content: 50.0%<br>SEQ ID NO: 100 Sense strand: 5'-UGUGAUGAGCUGGUGGCAGA UU-3'<br>SEQ ID NO: 421 Antisense strand: 5'-UCUGCCACCAGCUCAUCACA UU-3'<br>SEQ ID NO: 253 dsRNA: 5'-UGUGAUGAGCUGGUGGCAGA UU UCU AAA G-3' |
| Target sequence 101: 5'-GCA TGA GGA TTC AAG GCT-3' (SEQ ID NO: 578) (Position in gene sequence: 2238) | GC content: 45.0%<br>SEQ ID NO: 101 Sense strand: 5'-GCAUGAGGAUUCAAGGCU UU-3'<br>SEQ ID NO: 422 Antisense strand: 5'-AGCCUUGAAUCCUCAUGC UU-3'<br>SEQ ID NO: 254 dsRNA: 5'-GCAUGAGGAUUCAAGGCU UU UCU AAA G-3' |
| Target sequence 102: 5'-CTG GAG GCT ACG AGA ATG T-3' (SEQ ID NO: 579) (Position in gene sequence: 2256) | GC content: 47.62%<br>SEQ ID NO: 102 Sense strand: 5'-CUGGAGGCUACGAGAAUGU UU-3'<br>SEQ ID NO: 423 Antisense strand: 5'-ACAUUCUCGUAGCCUCCAG UU-3'<br>SEQ ID NO: 255 dsRNA: 5'-CUGGAGGCUACGAGAAUGU UU UCU AAA G-3' |
| Target sequence 103: 5'-TGG ACA TCC ACA TGA AGC-3' (SEQ ID NO: 580) (Position in gene sequence: 2285) | GC content: 45.0%<br>SEQ ID NO: 103 Sense strand: 5'-UGGACAUCCACAUGAAGC UU-3'<br>SEQ ID NO: 424 Antisense strand: 5'-GCUUCAUGUGGAUGUCCA UU-3'<br>SEQ ID NO: 256 dsRNA: 5'-UGGACAUCCACAUGAAGC UU UCU AAA G-3' |
| Target sequence 104: 5'-TAC GAG GAC CAG TGG CTG CA-3' (SEQ ID NO: 581) (Position in gene sequence: 2311) | GC content: 54.54%<br>SEQ ID NO: 104 Sense strand: 5'-UACGAGGACCAGUGGCUGCA UU-3'<br>SEQ ID NO: 425 Antisense strand: 5'-TGCAGCCACTGGTCCTCGTA UU-3'<br>SEQ ID NO: 257 dsRNA: 5'-UACGAGGACCAGUGGCUGCA UU UCU AAA G-3' |
| Target sequence 105: 5'-CAT GAC CGA GAG CCT GTT T-3' (SEQ ID NO: 582) (Position in gene sequence: 2355) | GC content: 47.62%<br>SEQ ID NO: 105 Sense strand: 5'-CAUGACCGAGAGCCUGUUU UU-3'<br>SEQ ID NO: 426 Antisense strand:5'-AAACAGGCUCUCGGUCAUG UU-3'<br>SEQ ID NO: 258 dsRNA: 5'-CAUGACCGAGAGCCUGUUU UU UCU AAA G-3' |
| Target sequence 106: 5'-GTG ATG AAC TTT GTG GTT CG-3' 3' (SEQ ID NO: 583) (Position in gene sequence: 2401) | GC content: 40.9%<br>SEQ ID NO: 106 Sense strand: 5'-GUGAUGAACUUUGUGGUUCG UU-3'<br>SEQ ID NO: 427 Antisense strand: 5'-CGAACCACAAAGUUCAUCAC UU-3'<br>SEQ ID NO: 259 dsRNA: 5'-GUGAUGAACUUUGUGGUUCG UU UCU AAA G-3' |

TABLE 3-continued

| | |
|---|---|
| Target sequence 107: 5'-AGA CGA GCA GCC GTC TCT-3' (SEQ ID NO: 584) (Position in gene sequence: 2429) | GC content: 55.0%<br>SEQ ID NO: 107 Sense strand: 5'-AGACGAGCAGCCGUCUCU UU-3'<br>SEQ ID NO: 428 Antisense strand: 5'-AGAGACGGCUGCUCGUCU UU-3'<br>SEQ ID NO: 260 dsRNA: 5'-AGACGAGCAGCCGUCUCU UU UCU AAA G-3' |
| Target sequence 108: 5'-GAC TCA TCC ACC TTC ACC CT-3' (SEQ ID NO: 585) (Position in gene sequence: 2461) | GC content: 50.0%<br>SEQ ID NO: 108 Sense strand: 5'-GACUCAUCCACCUUCACCCU UU-3'<br>SEQ ID NO: 429 Antisense strand: 5'-AGGGUGAAGGUGGAUGAGUC UU-3'<br>SEQ ID NO: 261 dsRNA: 5'-GACUCAUCCACCUUCACCCUUU UCU AAA G-3' |
| Target sequence 109: 5'-TTC CTG CGC TAC GAC TGT GT-3' (SEQ ID NO: 586) (Position in gene sequence: 2533) | GC content: 50.0%<br>SEQ ID NO: 109 Sense strand: 5'-UUCCUGCGCUACGACUGUGU UU-3'<br>SEQ ID NO: 430 Antisense strand: 5'-ACACAGUCGUAGCGCAGGAA UU-3'<br>SEQ ID NO: 262 dsRNA: 5'-UUCCUGCGCUACGACUGUGU UU UCU AAA G-3' |
| Target sequence 110: 5'-CAC ACG CTA CAT CAT GGT GT-3' (SEQ ID NO: 587) (Position in gene sequence: 2637) | GC content: 45.45%<br>SEQ ID NO: 110 Sense strand: 5'-CACACGCUACAUCAUGGUGU UU-3'<br>SEQ ID NO: 431 Antisense strand: 5'-ACACCAUGAUGUAGCGUGUG UU-3'<br>SEQ ID NO: 263 dsRNA: 5'-CACACGCUACAUCAUGGUGU UU UCU AAA G-3' |
| Target sequence 111: 5'-TGC CAT TGT GCC TTT TTA GG-3' (SEQ ID NO: 588) (Position in gene sequence: 2701) | GC content: 40.9%<br>SEQ ID NO: 111 Sense strand: 5'-UGCCAUUGUGCCUUUUUAGG UU-3'<br>SEQ ID NO: 432 Antisense strand: 5'-CCUAAAAAGGCACAAUGGCA UU-3'<br>SEQ ID NO: 264 dsRNA: 5'-UGCCAUUGUGCCUUUUUAGG UU UCU AAA G-3' |
| Target sequence 112: 5'-CAC TTC CTG AGT TCA TGT TC-3' (SEQ ID NO: 589) (Position in gene sequence: 2769) | GC content: 40.9%<br>SEQ ID NO: 112 Sense strand: 5'-CACUUCCUGAGUUCAUGUUC UU-3'<br>SEQ ID NO: 433 Antisense strand: 5'-GAACAUGAACUCAGGAAGUG UU-3'<br>SEQ ID NO: 265 dsRNA: 5'-CACUUCCUGAGUUCAUGUUC UU UCU AAA G-3' |
| Target sequence 113: 5'-CCT GAA CTG AAT ATG TCA CC-3' (SEQ ID NO: 590) (Position in gene sequence: 2796) | GC content: 40.9%<br>SEQ ID NO: 113 Sense strand: 5'-CCUGAACUGAAUAUGUCACC UU-3'<br>SEQ ID NO: 434 Antisense strand: 5'-GGUGACAUAUUCAGUUCAGG UU-3'<br>SEQ ID NO: 266 dsRNA: 5'-CCUGAACUGAAUAUGUCACC UU UCU AAA G-3' |
| Target sequence 114: 5'-CGC AGT CTC ACT CTG AAT AAA-3' (SEQ ID NO: 591) (Position in gene sequence: 2937) | GC content: 40.9%<br>SEQ ID NO: 114 Sense strand: 5'-CGCAGUCUCACUCUGAAUAAA UU-3'<br>SEQ ID NO: 435 Antisense strand: 5'-UUUAUUCAGAGUGAGACUGCG UU-3'<br>SEQ ID NO: 267 dsRNA: 5'-CGCAGUCUCACUCUGAAUAAAUU UCU AAA G-3' |
| Target sequence 115: 5'-GGA CAG TTT GTA AGT CTT G-3' (SEQ ID NO: 592) (Position in gene sequence: 2958) | GC content: 38.06%<br>SEQ ID NO: 115 Sense strand: 5'-GGACAGUUUGUAAGUCUUG UU-3'<br>SEQ ID NO: 436 Antisense strand: 5'-CAAGACUUACAAACUGUCC UU-3'<br>SEQ ID NO: 268 dsRNA: 5'-GGACAGUUUGUAAGUCUUG UU UCU AAA G-3' |
| Target sequence 116: 5'-TCA CTT CCC CTG TCC AGG TT-3' (SEQ ID NO: 593) (Position in gene sequence: 121) | GC content: 50.0%<br>SEQ ID NO: 116 Sense strand: 5'-UCACUUCCCCUGUCCAGGUU UU-3'<br>SEQ ID NO: 437 Antisense strand: 5'-AACCUGGACAGGGGAAGUGA UU-3'<br>SEQ ID NO: 269 dsRNA: 5'-UCACUUCCCCUGUCCAGGUU UU UCU AAA G-3' |

TABLE 3-continued

| | |
|---|---|
| Target sequence 117: 5'-TCA GCT TCC ACA TGT GTC AA-3' (SEQ ID NO: 594) (Position in gene sequence: 141) | GC content: 40.9%<br>SEQ ID NO: 117 Sense strand: 5'-UCAGCUUCCACAUGUGUCAA UU-3'<br>SEQ ID NO: 438 Antisense strand: 5'-UUGACACAUGUGGAAGCUGA UU-3'<br>SEQ ID NO: 270 dsRNA: 5'-UCAGCUUCCACAUGUGUCAA UU UCU AAA G-3' |
| Target sequence 118: 5'-GAC AAT CCT CGC CTT GTC T-3' (SEQ ID NO: 595) (Position in gene sequence: 241) | GC content: 47.62%<br>SEQ ID NO: 118 Sense strand: 5'-GACAAUCCUCGCCUUGUCU UU-3'<br>SEQ ID NO: 439 Antisense strand: 5'-AGACAAGGCGAGGAUUGUC UU-3'<br>SEQ ID NO: 271 dsRNA: 5'-GACAAUCCUCGCCUUGUCU UU UCU AAA G-3' |
| Target sequence 119: 5'-CAT CTG GAG CTT TCT GTA GC-3' (SEQ ID NO: 596) (Position in gene sequence: 270) | GC content: 45.45%<br>SEQ ID NO: 119 Sense strand: 5'-GCAUCUGGAGCUUUCUGUA UU-3'<br>SEQ ID NO: 440 Antisense strand: 5'-UACAGAAAGCUCCAGAUGC UU-3'<br>SEQ ID NO: 272 dsRNA: 5'-GCAUCUGGAGCUUUCUGUA UU UCU AAA G-3' |
| Target sequence 120: 5'-GAG ATC CCA GGA TCC TGG-3' (SEQ ID NO: 597) (Position in gene sequence: 414) | GC content: 55.0%<br>SEQ ID NO: 120 Sense strand: 5'-GAGAUCCCAGGAUCCUGG UU-3'<br>SEQ ID NO: 441 Antisense strand: 5'-CCAGGAUCCUGGGAUCUC UU-3'<br>SEQ ID NO: 273 dsRNA: 5'-GAGAUCCCAGGAUCCUGG UU UCU AAA G-3' |

The composition of the present invention may include: siRNA which includes a sense RNA having at least one sequence selected from the group consisting of sequences of SEQ ID NOs: 121 to 157 in Table 4 below, and an antisense RNA having a complementary sequence thereto; or dsRNA having at least one sequence selected from the group consisting of sequences of SEQ ID NOs: 274 to 310 in Table 4 below.

In this regard, siRNA which includes a sense RNA having at least one sequence selected from the group consisting of sequences of SEQ ID NOs: 121 to 157 in Table 4 below, and an antisense RNA having a complementary sequence thereto; or dsRNA having at least one sequence selected from the group consisting of sequences of SEQ ID NOs: 274 to 310 in Table 4 below, may target a sequence of human SF3B4 gene (SEQ ID NO: 4) to inhibit expression of the human SF3B4 gene through RNAi, thereby achieving effects of preventing or treating HCC.

TABLE 4

| | |
|---|---|
| Target sequence 121: 5'-AAT CAG GAT GCC ACT GTG TA-3' (SEQ ID NO: 598) (Position in gene sequence: 521) | GC content: 40.9%<br>SEQ ID NO: 121 Sense strand: 5'-AAUCAGGAUGCCACUGUGUA UU-3'<br>SEQ ID NO: 442 Antisense strand: 5'-UACACAGUGGCAUCCUGAUU UU-3'<br>SEQ ID NO: 274 dsRNA: 5'-AAUCAGGAUGCCACUGUGUA UU UCU AAA G-3' |
| Target sequence 122: 5'-CTG GAT GAG AAG GTT AGT GA-3' (SEQ ID NO: 599) (Position in gene sequence: 551) | GC content: 40.9%<br>SEQ ID NO: 122 Sense strand: 5'-CUGGAUGAGAAGGUUAGUGA UU-3'<br>SEQ ID NO: 443 Antisense strand: 5'-UCACUAACCUUCUCAUCCAG UU-3'<br>SEQ ID NO: 275 dsRNA: 5'-CUGGAUGAGAAGGUUAGUGA UU UCU AAA G-3' |
| Target sequence 123: 5'-TGT GGG AAC TGT TTC TCC AG-3' (SEQ ID NO: 600) (Position in gene sequence: 579) | GC content: 45.45%<br>SEQ ID NO: 123 Sense strand: 5'-UGUGGGAACUGUUUCUCCAG UU-3'<br>SEQ ID NO: 444 Antisense strand: 5'-CUGGAGAAACAGUUCCCACA UU-3' |

TABLE 4-continued

| | |
|---|---|
| | SEQ ID NO: 276 dsRNA: 5'-UGUGGGAACUGUUUCUCCAG UU UCU AAA G-3' |
| Target sequence 124: 5'-CTG GAC CAG TAG TCA ACA-3' (SEQ ID NO: 601) (Position in gene sequence: 599) | GC content: 45.0%<br>SEQ ID NO: 124 Sense strand: 5'-CUGGACCAGUAGUCAACA UU-3'<br>SEQ ID NO: 445 Antisense strand: 5'-UGUUGACUACUGGUCCAG UU-3'<br>SEQ ID NO: 277 dsRNA: 5'-CUGGACCAGUAGUCAACA UU UCU AAA G-3' |
| Target sequence 125: 5'-CCA AAG GAT AGA GTC ACT G-3' (SEQ ID NO: 602) (Position in gene sequence: 626) | GC content: 42.86%<br>SEQ ID NO: 125 Sense strand: 5'-CCAAAGGAUAGAGUCACUG UU-3'<br>SEQ ID NO: 446 Antisense strand: 5'-CAGUGACUCUAUCCUUUGG UU-3'<br>SEQ ID NO: 278 dsRNA: 5'-CCAAAGGAUAGAGUCACUG UU UCU AAA G-3' |
| Target sequence 126: 5'-CAG CAC CAA GGC TAT GGC TTT-3' (SEQ ID NO: 603) (Position in gene sequence: 647) | GC content: 47.83%<br>SEQ ID NO: 126 Sense strand: 5'-CAGCACCAAGGCUAUGGCUUU UU-3'<br>SEQ ID NO: 447 Antisense strand: 5'-AAAGCCAUAGCCUUGGUGCUG UU-3'<br>SEQ ID NO: 279 dsRNA: 5'-CAGCACCAAGGCUAUGGCUUU UU UCU AAA G-3' |
| Target sequence 127: 5'-GTG GAA TTC TTG AGT GAG GA-3' (SEQ ID NO: 604) (Position in gene sequence: 668) | GC content: 40.9%<br>SEQ ID NO: 127 Sense strand: 5'-GUGGAAUUCUUGAGUGAGGA UU-3'<br>SEQ ID NO: 448 Antisense strand: 5'-UCCUCACUCAAGAAUUCCAC UU-3'<br>SEQ ID NO: 280 dsRNA: 5'-GUGGAAUUCUUGAGUGAGGA UU UCU AAA G-3' |
| Target sequence 128: 5'-GCT GAC TAT GCC ATT AAG AT-3' (SEQ ID NO: 605) (Position in gene sequence: 692) | GC content: 36.36%<br>SEQ ID NO: 128 Sense strand: 5'-GCUGACUAUGCCAUUAAGAU UU-3'<br>SEQ ID NO: 449 Antisense strand: 5'-AUCUUAAUGGCAUAGUCAGC UU-3'<br>SEQ ID NO: 281 dsRNA: 5'-GCUGACUAUGCCAUUAAGAU UU UCU AAA G-3' |
| Target sequence 129: 5'-ACA TGA TCA AAC TCT ATG G-3' (SEQ ID NO: 606) (Position in gene sequence: 717) | GC content: 33.33%<br>SEQ ID NO: 129 Sense strand: 5'-ACAUGAUCAAACUCUAUGG UU-3'<br>SEQ ID NO: 450 Antisense strand: 5'-CCAUAGAGUUUGAUCAUGU UU-3'<br>SEQ ID NO: 282 dsRNA: 5'-ACAUGAUCAAACUCUAUGG UU UCU AAA G-3' |
| Target sequence 130: 5'-GGT GAA CAA AGC ATC AGC-3' (SEQ ID NO: 607) (Position in gene sequence: 748) | GC content: 45.0%<br>SEQ ID NO: 130 Sense strand: 5'-GGUGAACAAAGCAUCAGC UU-3'<br>SEQ ID NO: 451 Antisense strand: 5'-GCUGAUGCUUUGUUCACC UU-3'<br>SEQ ID NO: 283 dsRNA: 5'-GGUGAACAAAGCAUCAGC UU UCU AAA G-3' |
| Target sequence 131: 5'-CCT GAG ATT GAT GAG AAG-3' (SEQ ID NO: 608) (Position in gene sequence: 818) | GC content: 40.0%<br>SEQ ID NO: 131 Sense strand: 5'-CCUGAGAUUGAUGAGAAG UU-3'<br>SEQ ID NO: 452 Antisense strand: 5'-CUUCUCAUCAAUCUCAGG UU-3'<br>SEQ ID NO: 284 dsRNA: 5'-CCUGAGAUUGAUGAGAAG UU UCU AAA G-3' |
| Target sequence 132: 5'-GGT CAT CTT ACA AAC CC-3' (SEQ ID NO: 609) (Position in gene sequence: 865) | GC content: 42.1%<br>SEQ ID NO: 132 Sense strand: 5'-GGUCAUCUUACAAACCC UU-3'<br>SEQ ID NO: 453 Antisense strand: 5'-GGGUUUGUAAGAUGACC UU-3'<br>SEQ ID NO: 285 dsRNA: 5'-GGUCAUCUUACAAACCC UU UCU AAA G-3' |
| Target sequence 133: 5'-CCT GAC ACA GGC AAC TCC-3' (SEQ ID NO: 610) (Position in gene sequence: 899) | GC content: 55.0%<br>SEQ ID NO: 133 Sense strand: 5'-CCUGACACAGGCAACUCC UU-3'<br>SEQ ID NO: 454 Antisense strand: 5'-GGAGUUGCCUGUGUCAGG UU-3' |

TABLE 4-continued

| | |
|---|---|
| | SEQ ID NO: 286 dsRNA: 5'-CCUGACACAGGCAACUCC UU UCU AAA G-3' |
| Target sequence 134: 5'-GCT TCA TTT GAT GCT TCG GA-3' (SEQ ID NO: 611) (Position in gene sequence: 941) | GC content: 40.9%<br>SEQ ID NO: 134 Sense strand: 5'-GCUUCAUUUGAUGCUUCGGA UU-3'<br>SEQ ID NO: 455 Antisense strand: 5'-UCCGAAGCAUCAAAUGAAGC UU-3'<br>SEQ ID NO: 287 dsRNA: 5'-GCUUCAUUUGAUGCUUCGGA UU UCU AAA G-3' |
| Target sequence 135: 5'-TGC AGC AAT TGA AGC CAT GA-3' (SEQ ID NO: 612) (Position in gene sequence: 961) | GC content: 40.9%<br>SEQ ID NO: 135 Sense strand: 5'-UGCAGCAAUUGAAGCCAUGA UU-3'<br>SEQ ID NO: 456 Antisense strand: 5'-UCAUGGCUUCAAUUGCUGCA UU-3'<br>SEQ ID NO: 288 dsRNA: 5'-UGCAGCAAUUGAAGCCAUGA UU UCU AAA G-3' |
| Target sequence 136: 5'-GCA GTA CCT CTG TAA CCG T-3' (SEQ ID NO: 613) (Position in gene sequence: 985) | GC content: 47.62%<br>SEQ ID NO: 136 Sense strand: 5'-GCAGUACCUCUGUAACCGU UU-3'<br>SEQ ID NO: 457 Antisense strand: 5'-ACGGUUACAGAGGUACUGC UU-3'<br>SEQ ID NO: 289 dsRNA: 5'-GCAGUACCUCUGUAACCGU UU UCU AAA G-3' |
| Target sequence 137: 5'-CAC CGT ATC TTA TGC CTT CA-3' (SEQ ID NO: 614) (Position in gene sequence: 1009) | GC content: 40.9%<br>SEQ ID NO: 137 Sense strand: 5'-CACCGUAUCUUAUGCCUUCA UU-3'<br>SEQ ID NO: 458 Antisense strand: 5'-UGAAGGCAUAAGAUACGGUG UU-3'<br>SEQ ID NO: 290 dsRNA: 5'-CACCGUAUCUUAUGCCUUCA UU UCU AAA G-3' |
| Target sequence 138: 5'-GAA CGA CTT CTG GCA GCT CA-3' (SEQ ID NO: 615) (Position in gene sequence: 1067) | GC content: 50.0%<br>SEQ ID NO: 138 Sense strand: 5'-GAACGACUUCUGGCAGCUCA UU-3'<br>SEQ ID NO: 459 Antisense strand: 5'-UGAGCUGCCAGAAGUCGUUC UU-3'<br>SEQ ID NO: 291 dsRNA: 5'-GAACGACUUCUGGCAGCUCA UU UCU AAA G-3' |
| Target sequence 139: 5'-CCT CAT CAG CTG TTT GCA GA-3' (SEQ ID NO: 616) (Position in gene sequence: 1112) | GC content: 45.45%<br>SEQ ID NO: 139 Sense strand: 5'-CCUCAUCAGCUGUUUGCAGA UU-3'<br>SEQ ID NO: 460 Antisense strand: 5'-UCUGCAAACAGCUGAUGAGG UU-3'<br>SEQ ID NO: 292 dsRNA: 5'-CCUCAUCAGCUGUUUGCAGA UU UCU AAA G-3' |
| Target sequence 140: 5'-TGG TCA TGG ACA CTC ACA TC-3' (SEQ ID NO: 617) (Position in gene sequence: 1351) | GC content: 45.45%<br>SEQ ID NO: 140 Sense strand: 5'-UGGUCAUGGACACUCACAUC UU-3'<br>SEQ ID NO: 461 Antisense strand: 5'-GAUGUGAGUGUCCAUGACCA UU-3'<br>SEQ ID NO: 293 dsRNA: 5'-UGGUCAUGGACACUCACAUC UU UCU AAA G-3' |
| Target sequence 141: 5'-GAT GTC TCA GAT GCA GCT-3' (SEQ ID NO: 618) (Position in gene sequence: 1408) | GC content: 45.0%<br>SEQ ID NO: 141 Sense strand: 5'-GAUGUCUCAGAUGCAGCU UU-3'<br>SEQ ID NO: 462 Antisense strand: 5'-AGCUGCAUCUGAGACAUC UU-3'<br>SEQ ID NO: 294 dsRNA: 5'-GAUGUCUCAGAUGCAGCU UU UCU AAA G-3' |
| Target sequence 142: 5'-CCT CAT GGC TTA GGA CAT-3' (SEQ ID NO: 619) (Position in gene sequence: 1439) | GC content: 45.0%<br>SEQ ID NO: 142 Sense strand: 5'-CCUCAUGGCUUAGGACAU UU-3'<br>SEQ ID NO: 463 Antisense strand: 5'-AUGUCCUAAGCCAUGAGG UU-3'<br>SEQ ID NO: 295 dsRNA: 5'-CCUCAUGGCUUAGGACAU UU UCU AAA G-3' |
| Target sequence 143: 5'-TCA CAT TTT CCT TCC TCC TG-3' (SEQ ID NO: 620) (Position in gene sequence: 1771) | GC content: 40.9%<br>SEQ ID NO: 143 Sense strand: 5'-UCACAUUUUCCUUCCUCCUG UU-3'<br>SEQ ID NO: 464 Antisense strand: 5'-CAGGAGGAAGGAAAAUGUGA UU-3' |

TABLE 4-continued

| | |
|---|---|
| | SEQ ID NO: 296 dsRNA: 5'-UCACAUUUCCUUCCUCCUG UU UCU AAA G-3' |
| Target sequence 144: 5'-CCT TGG ACC AAT CAG AGA TG-3' (SEQ ID NO: 621) (Position in gene sequence: 1818) | GC content: 45.45%<br>SEQ ID NO: 144 Sense strand: 5'-CCUUGGACCAAUCAGAGAUG UU-3'<br>SEQ ID NO: 465 Antisense strand: 5'-CAUCUCUGAUUGGUCCAAGG UU-3'<br>SEQ ID NO: 297 dsRNA: 5'-CCUUGGACCAAUCAGAGAUG UU UCU AAA G-3' |
| Target sequence 145: 5'-GGC AAA GGT ACT AAT CCC TT-3' (SEQ ID NO: 622) (Position in gene sequence: 1852) | GC content: 40.9%<br>SEQ ID NO: 145 Sense strand: 5'-GGCAAAGGUACUAAUCCCUU UU-3'<br>SEQ ID NO: 466 Antisense strand: 5'-AAGGGAUUAGUACCUUUGCC UU-3'<br>SEQ ID NO: 298 dsRNA: 5'-GGCAAAGGUACUAAUCCCUU UU UCU AAA G-3' |
| Target sequence 146: 5'-TTC CAC AGG AGG TAT TTC-3' (SEQ ID NO: 623) (Position in gene sequence: 1911) | GC content: 40.0%<br>SEQ ID NO: 146 Sense strand: 5'-UUCCACAGGAGGUAUUUC UU-3'<br>SEQ ID NO: 467 Antisense strand: 5'-GAAAUACCUCCUGUGGAA UU-3'<br>SEQ ID NO: 299 dsRNA: 5'-UUCCACAGGAGGUAUUUC UU UCU AAA G-3' |
| Target sequence 147: 5'-GGT CCT GAG TAT TTT GCA-3' (SEQ ID NO: 624) (Position in gene sequence: 1940) | GC content: 40.0%<br>SEQ ID NO: 147 Sense strand: 5'-GGUCCUGAGUAUUUUGCA UU-3'<br>SEQ ID NO: 468 Antisense strand: 5'-UGCAAAAUACUCAGGACC UU-3'<br>SEQ ID NO: 300 dsRNA: 5'-GGUCCUGAGUAUUUUGCA UU UCU AAA G-3' |
| Target sequence 148: 5'-CCA AAT CTG CAA GAA GGC T-3' (SEQ ID NO: 625) (Position in gene sequence: 18) | GC content: 42.86%<br>SEQ ID NO: 148 Sense strand: 5'-CCAAAUCUGCAAGAAGGCU UU-3'<br>SEQ ID NO: 469 Antisense strand: 5'-AGCCUUCUUGCAGAUUUGG UU-3'<br>SEQ ID NO: 301 dsRNA: 5'-CCAAAUCUGCAAGAAGGCU UU UCU AAA G-3' |
| Target sequence 149: 5'-GGA ACT CTT CAG CAC ATC CTT-3' (SEQ ID NO: 626) (Position in gene sequence: 95) | GC content: 43.48%<br>SEQ ID NO: 149 Sense strand: 5'-GGAACUCUUCAGCACAUCCUU UU-3'<br>SEQ ID NO: 470 Antisense strand: 5'-AAGGAUGUGCUGAAGAGUUCC UU-3'<br>SEQ ID NO: 302 dsRNA: 5'-GGAACUCUUCAGCACAUCCUU UU UCU AAA G-3' |
| Target sequence 150: 5'-CTC TGG ACA ACA GAA GAA GA-3' (SEQ ID NO: 627) (Position in gene sequence: 116) | GC content: 40.9%<br>SEQ ID NO: 150 Sense strand: 5'-CUCUGGACAACAGAAGAAGA UU-3'<br>SEQ ID NO: 471 Antisense strand: 5'-UCUUCUUCUGUUGUCCAGAG UU-3'<br>SEQ ID NO: 303 dsRNA: 5'-CUCUGGACAACAGAAGAAGA UU UCU AAA G-3' |
| Target sequence 151: 5'-TGA GAG CAG TGT GAT TCT-3' (SEQ ID NO: 628) (Position in gene sequence: 201) | GC content: 40.0%<br>SEQ ID NO: 151 Sense strand: 5'-UGAGAGCAGUGUGAUUCU UU-3'<br>SEQ ID NO: 472 Antisense strand: 5'-AGAAUCACACUGCUCUCA UU-3'<br>SEQ ID NO: 304 dsRNA: 5'-UGAGAGCAGUGUGAUUCU UU UCU AAA G-3' |
| Target sequence 152: 5'-CAA GTC TAG CAG TGC AT-3' (SEQ ID NO: 629) (Position in gene sequence: 221) | GC content: 42.1%<br>SEQ ID NO: 152 Sense strand: 5'-CAAGUCUAGCAGUGCAU UU-3'<br>SEQ ID NO: 473 Antisense strand: 5'-AUGCACUGCUAGACUUG UU-3'<br>SEQ ID NO: 305 dsRNA: 5'-CAAGUCUAGCAGUGCAU UU UCU AAA G-3' |
| Target sequence 153: 5'-CTC GCT AAG ACA ACT AGC A-3' (SEQ ID NO: 630) (Position in gene sequence: 270) | GC content: 42.86%<br>SEQ ID NO: 153 Sense strand: 5'-CUCGCUAAGACAACUAGCA UU-3'<br>SEQ ID NO: 474 Antisense strand: 5'-UGCUAGUUGUCUUAGCGAGA UU-3' |

TABLE 4-continued

| | |
|---|---|
| | SEQ ID NO: 306 dsRNA: 5'-CUCGCUAAGACAACUAGCA UU UCU AAA G-3' |
| Target sequence 154: 5'-CAG GTT AAG TTT CGG AGG CT-3' (SEQ ID NO: 631) (Position in gene sequence: 331) | GC content: 45.45%<br>SEQ ID NO: 154 Sense strand: 5'-CAGGUUAAGUUUCGGAGGCU UU-3'<br>SEQ ID NO: 475 Antisense strand: 5'-AGCCUCCGAAACUUAACCUG UU-3'<br>SEQ ID NO: 307 dsRNA: 5'-CAGGUUAAGUUUCGGAGGCU UU UCU AAA G-3' |
| Target sequence 155: 5'-GCT TCC AGG CAC CTC CTC TT-3' (SEQ ID NO: 632) (Position in gene sequence: 369) | GC content: 54.54%<br>SEQ ID NO: 155 Sense strand: 5'-GCUUCCAGGCACCUCCUCUU UU-3'<br>SEQ ID NO: 476 Antisense strand: 5'-AAGAGGAGGUGCCUGGAAGC UU-3'<br>SEQ ID NO: 308 dsRNA: 5'-GCUUCCAGGCACCUCCUCUU UU UCU AAA G-3' |
| Target sequence 156: 5'-GAA GTG GAA GTC GTG CTG AG-3' (SEQ ID NO: 633) (Position in gene sequence: 427) | GC content: 50.0%<br>SEQ ID NO: 156 Sense strand: 5'-GAAGUGGAAGUCGUGCUGAG UU-3'<br>SEQ ID NO: 477 Antisense strand: 5'-CUCAGCACGACUUCCACUUC UU-3'<br>SEQ ID NO: 309 dsRNA: 5'-GAAGUGGAAGUCGUGCUGAG UU UCU AAA G-3' |
| Target sequence 157: 5'-GAT CTC TTT CGC CAT GGC TG-3' (SEQ ID NO: 634) (Position in gene sequence: 481) | GC content: 50.0%<br>SEQ ID NO: 157 Sense strand: 5'-GAUCUCUUUCGCCAUGGCUG UU-3'<br>SEQ ID NO: 478 Antisense strand: 5'-CAGCCAUGGCGAAAGAGAUC UU-3'<br>SEQ ID NO: 310 dsRNA: 5'-GAUCUCUUUCGCCAUGGCUG UU UCU AAA G-3' |

The siRNA or dsRNA of the present invention may be one capable of being loaded on a carrier while carrying RNA molecules depending on types of the carrier, which is not particularly limited as long as it is known in the art, and may include, but is not limited to, at least one selected from the group consisting of, for example, liposomes, lipofectamines, dendrimers, micelles, porous silica particles, amino clay, gold nanoparticles, magnetic nanoparticles, graphene, oxidized graphene, chitosan, dextran, pectin, manganese dioxide two-dimensional sheet, PVA, gelatin, silica, glass particles, protamine, exosome, polyethyleneimine, N-butyl cyanoacrylate, gel foam, ethanol, nanocrystals, nanotubes, carbon nanoparticles, hyaluronic acid, iron oxide, polylactic acid, polybutyl cyanoacrylate, albumin, lipid particles, polyethylene glycol, poly-L-guluronic alginate, polyglycolic-polylactic acid, polydioxanone, polyglycolic acid-co-caprolactone, polypropylene and hydrogel, preferably, porous silica particles having advantages such as high RNA retention, sustained release, biodegradability, etc.

The siRNA or dsRNA of the present invention may be loaded on porous silica particles, wherein the particles are particles of silica material ($SiO_2$) and have a nano-sized particle diameter.

The porous silica particles may be porous particles having nano-sized pores and may carry physiologically active substances ("bioactive materials") such as siRNA or dsRNA of the present invention on the surfaces of the particles and/or insides of the pores.

The porous silica particles are biodegradable particles and, when the particles loaded with the bioactive material and is administered in a body, may release the bioactive material while being biodegraded in the body. That is, biodegradation of the porous silica particles results in release of the bioactive material. In this case, the porous silica particles according to the present invention may be slowly degraded in the body so that the loaded bioactive material can have sustained release properties. For example, t when a ratio of absorbance in the following Equation 1 becomes 1/2 may be 20 or more.

$$A_t/A_0 \qquad \text{[Equation 1]}$$

(wherein $A_0$ is absorbance of the porous silica particles measured by placing 5 ml of a suspension including 1 mg/ml of the porous silica particles into a cylindrical dialysis membrane having pores with a diameter of 50 kDa, 15 ml of the same solvent as the suspension is placed outside the dialysis membrane while being in contact with the dialysis membrane, followed by horizontal agitation at 60 rpm and 37° C. inside and outside the dialysis membrane, pH of the suspension is 7.4, and $A_t$ is absorbance of the porous silica particles measured after t hours elapses from the measurement of $A_0$).

Equation 1 indicates how fast the porous silica particles are degraded under environments similar to the body.

In Equation 1, the absorbance $A_0$ and $A_t$ may be measured, for example, after placing the porous silica particles and the suspension in a cylindrical dialysis membrane, and further placing the same suspension on the outside of the dialysis membrane.

The particles are biodegradable and may be slowly degraded in the suspension, wherein the diameter of 50 kDa corresponds to about 5 nm, the biodegraded particles can pass through a 50 kDa dialysis membrane, this cylindrical dialysis membrane is under horizontal agitation at 60 rpm such that the suspension is evenly admixed, and the degraded particles may come out of the dialysis membrane.

The absorbance in Equation 1 may be measured, for example, under an environment in which the suspension outside the dialysis membrane is replaced with a new suspension. The suspension may be one that is constantly replaced, one that is replaced at a constant period wherein the constant period may be periodic or irregular. For example, the replacement may be performed within a range of 1 hour to 1 week, in particular, at 1-, 2-, 3-, 6-, 12-, 24-hours intervals, or 2-, 3-, 4-, 7-days interval, etc., but it is not limited thereto.

A ratio of absorbance of 1/2 means that, after t hours, the absorbance becomes half of the initial absorbance, therefore, means that approximately half of the porous silica particles have been degraded.

The suspension may be a buffer solution and, for example, at least one selected from the group consisting of phosphate buffered saline (PBS) and simulated body fluid (SBF), and more specifically, PBS.

t when the ratio of absorbance in Equation 1 becomes 1/2 is 20 or more or 24 or more, for example, t may be 20 to 120, specifically, 20 to 96, 20 to 72, 30 to 70, 40 to 70, 50 to 65, etc. within the above range, but it is not limited thereto.

The particles are characterized in that t when the ratio of absorbance in Equation 1 becomes 1/5 may be, for example, 70 to 140, specifically, 80 to 140, 80 to 120, 80 to 110, 70 to 140, 70 to 120, 70 to 110, etc. within the above range, but it is not limited thereto.

The particles are characterized in that t when the ratio of absorbance in Equation 1 becomes 1/20 may be, for example, 130 to 220, specifically, 130 to 200, 140 to 200, 140 to 180, 150 to 180, etc. within the above range, but it is not limited thereto.

The particles are characterized in that t when the measured absorbance becomes 0.01 or less may be, for example, 250 or more, specifically, 300 or more, 350 or more, 400 or more, 500 or more, 1000 or more, etc. within the above range while having an upper limit of 2000, but it is not limited thereto.

The particles are characterized in that the absorbance ratio in Equation 1 has high positive correlation with t, specifically, Pearson correlation coefficient may be 0.8 or more, for example, 0.9 or more, 0.95 or more, etc.

t in Equation 1 means how fast the porous silica particles are degraded under environments similar to the body, for example, may be controlled by adjusting the surface area, particle diameter, pore diameter, substituent on the surface of the porous silica particle and/or inside the pore, compactness of the surface, etc.

More particularly, t may be reduced by increasing the surface area of the particle or may be increased by reducing the surface area thereof. The surface area may be regulated by adjusting the diameter of the particles and/or the diameter of the pores. In addition, placing a substituent on the surface of the particle and/or the inside of the pore may reduce direct exposure of the porous silica particles to the environment (such as a solvent), thereby increasing t. Further, loading the bioactive material on the porous silica particles and increasing affinity between the bioactive material and the porous silica particles may reduce direct exposure of the porous silica particles to the environment, thereby increasing t. In addition, the surface may be made more densely in the preparation of the particles so as to increase t. In the above, various examples of adjusting t in Equation 1 have been described, but it is not limited thereto.

The porous silica particles may be, for example, spherical particles, but it is not limited thereto.

The average diameter of the porous silica particles may be, for example, 100 to 1000 nm, specifically, 100 to 800 nm, 100 to 500 nm, 100 to 400 nm, 100 to 300 nm, 100 to 200 nm, etc. within the above range, but it is not limited thereto.

The average pore diameter of the particles may be, for example, 1 to 100 nm, specifically, 4 to 100 nm, 4 to 50 nm, 4 to 30 nm, 10 to 30 nm, etc. within the above range, but it is not limited thereto. Due to the large pore diameter, the particles may carry a large amount of the bioactive material and/or the bioactive material having a large size.

The porous silica particles may have a BET surface area of, for example, 200 to 700 $m^2/g$, specifically, 200 to 700 $m^2/g$, 200 to 650 $m^2/g$, 250 to 650 $m^2/g$, 300 to 700 $m^2/g$, 300 to 650 $m^2/g$, 300 to 600 $m^2/g$, 300 to 550 $m^2/g$, 300 to 500 $m^2/g$, 300 to 450 $m^2/g$, etc. within the above range, but it is not limited thereto.

The porous silica particles may have a volume per gram (g) of, for example, 0.7 to 2.2 ml, specifically, 0.7 to 2.0 ml, 0.8 to 2.2 ml, 0.8 to 2.0 ml, 0.9 to 2.0 ml, 1.0 to 2.0 ml, etc. within the above range, but it is not limited thereto. If the volume per gram (g) is too small, a degradation rate may be too high. Further, it may be difficult to manufacture excessively large particles or the particles may not have a complete shape.

The porous silica particles may have a hydrophilic substituent and/or a hydrophobic substituent on an outer surface thereof and/or inside the pore. For example, only hydrophilic substituents or only hydrophobic substituents may be present on both the surface of the particle and the inside of the pore, hydrophilic substituents or hydrophobic substituents may be present on either the surface of the particle or the inside of the pore, otherwise, a hydrophilic substituent may be present on the surface of the particle while a hydrophobic substituent may be present inside of the pore, and vice versa.

Release of the bioactive material loaded on the porous silica particles is mainly conducted by degradation of the particles. Specifically, interaction of the porous silica particles with respect to the release environment of the bioactive material is controlled by adjusting the substituent, thereby regulating a degradation rate of the particles thus to control a release rate of the bioactive material. Further, the bioactive material may be diffused and released from the particles wherein adjusting the substituent may regulate a binding force of the bioactive material with the particles, thereby controlling the release of the bioactive material.

Further, for improvement of the binding force between the particles and a poorly soluble (hydrophobic) bioactive material, an additional process may be further included so that a hydrophobic substituent is present inside the pore while a hydrophilic substituent is present on the surface of the particle, in consideration of easiness in use and formulation of the composition according to the present invention.

The hydrophilic substituent may include, for example, aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, ether, indene, sulfonyl, methylphosphonate, polyethylene glycol, substituted or unsubstituted $C_1$ to $C_{30}$ alkyl, substituted or unsubstituted $C_3$ to $C_{30}$ cycloalkyl, substituted or unsubstituted $C_6$ to $C_{30}$ aryl, and $C_1$ to $C_{30}$ ester groups, etc., while the hydrophobic substituent may include, for example, substituted or unsubstituted $C_1$ to $C_{30}$ alkyl, substituted or unsubstituted $C_3$ to $C_{30}$ cycloalkyl, substituted or unsubstituted $C_6$ to $C_{30}$ aryl, $C_2$ to $C_{30}$ heteroaryl, halogen, $C_1$ to $C_{30}$ ester, and halogen-containing groups, etc.

The "substituted" functional group in the "substituted or unsubstituted" mentioned above may include at least one selected from the group consisting of aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, ether, indene, sulfonyl, methylphosphonate and polyethylene glycol.

Further, the porous silica particles may be positively and/or negatively charged on the outer surface thereof and/or the inside of the pore. For example, both the surface of the particle and the inside of the pore may be positively or negatively charged. Alternatively, only the surface of the particle or the inside of the pore may be positively or negatively charged. Otherwise, the surface of the particle may be positively charged while the inside of the pore may be negatively charged, and vice versa.

The charging may be performed, for example, by the presence of a cationic substituent or an anionic substituent.

The cationic substituent may include, for example, an amino group or other nitrogen-containing group as a basic group, while the anionic substituent may include, for example, a carboxyl group (—COOH), a sulfonic acid group (—SO$_3$H), or a thiol group (—SH), etc., but it is not limited thereto.

Similarly, due to charging as described above, interaction between the porous silica particles with respect to the environment for releasing the bioactive material is controlled by adjusting the substituent so that a degradation rate of the particles may be regulated thus to control a release rate of the bioactive material. Further, the bioactive material may be diffused and released from the particles wherein adjusting the substituent may regulate a binding force of the bioactive material with the particles, thereby controlling the release of the bioactive material.

Other than the above substituents, the porous silica particles may further include another substituent, which is present on the surface of the particle and/or the inside of the pore, in order to carry a bioactive material, transfer the bioactive material to a target cell, carry a material used for other purposes or bind other additional substituents, etc., wherein the substituent may further include an antibody, a ligand, a cell permeable peptide, an aptamer, etc. coupled thereto.

The above-mentioned substituents, charges, coupled substances, etc. present on the surface of the particle and/or the inside of the pore may be added thereto, for example, by surface modification.

The surface modification may be performed, for example, by reacting a compound having a substituent to be introduced, with the particles. In this regard, the compound may include, for example, alkoxysilane having a C1 to C10 alkoxy group, but it is not limited thereto. The alkoxysilane may have at least one alkoxy group, specifically, 1 to 3 alkoxy groups, and may have a substituent to be introduced into a site in which the alkoxy group is not bonded or a substituent substituted with the alkoxy group.

The porous silica particles may be prepared by, for example, a small pore particle preparation and pore expansion process. If necessary, the particles may be prepared through further calcination, and surface modification processes, etc. If the particles are subjected to both the calcination and the surface modification processes, the particles may be surface-modified after the calcinations.

The small pore particles may be, for example, particles having an average pore diameter of 1 to 5 nm.

The small pore particles may be obtained by adding a surfactant and a silica precursor to a solvent and then agitating and homogenizing the solution.

Water and/or organic solvents may be used as the solvent, and the organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; carbon-based aromatics such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (CELLOSOLVE) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; and dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethyl phosphoamide, tetramethylurea, N-methylcarrolactam, tetrahydrofuran, m-dioxane, p-dioxane, 1,2-dimethoxyethan and the like. Specifically, alcohol, more specifically, methanol may be used, but it is not limited thereto.

When using a mixed solvent of water and an organic solvent as the solvent, a ratio of water and an organic solvent may be used in a volume ratio of, for example, 1:0.7 to 1.5, e.g., 1:0.8 to 1.3, but it is not limited thereto.

The surfactant may be, for example, cetyltrimethylammonium bromide (CTAB), hexadecyltrimethylammonium bromide (TMABr), hexadecyltrimethylpyridinium chloride (TMPrCl), tetramethylammonium chloride (TMACl), and the like, and specifically, CTAB may be used.

The surfactant may be added in an amount of, for example, 1 to 10 g per liter of solvent, specifically, 1 to 8 g, 2 to 8 g, 3 to 8 g, etc. within the above range, but it is not limited thereto.

The silica precursor may be added after the agitation with addition of the surfactant to the solvent. The silica precursor may be, for example, tetramethyl orthosilicate (TMOS), but it is not limited thereto.

The agitation may be performed, for example, for 10 to 30 minutes, but it is not limited thereto.

The silica precursor may be added thereto, for example, in an amount of 0.5 to 5 ml per liter of solvent, specifically, 0.5 to 4 ml, 0.5 to 3 ml, 0.5 to 2 ml, 1 to 2 ml, etc. within the above range, but it is not limited thereto. Rather, if necessary, sodium hydroxide as a catalyst may be further used, wherein the catalyst may be added while agitating after adding the surfactant to the solvent and before adding the silica precursor to the solvent.

Sodium hydroxide may be used in an amount of, for example, 0.5 to 8 ml per liter of solvent, specifically, 0.5 to 5 ml, 0.5 to 4 ml, 1 to 4 ml, 1 to 3 ml, 2 to 3 ml, etc. within the above range, based on 1 M aqueous sodium hydroxide solution, but is not limited thereto.

After the addition of the silica precursor, the solution may be reacted with agitation. The agitation may be performed, for example, for 2 to 15 hours, specifically, 3 to 15 hours, 4 to 15 hours, 4 to 13 hours, 5 to 12 hours, 6 to 12 hours, 6 to 10 hours, etc. within the above range, but it is not limited thereto. If an agitating time (reaction time) is too short, nucleation may be insufficient.

After the agitation, the solution may be aged. Aging may be performed, for example, for 8 to 24 hours, specifically, 8 to 20 hours, 8 to 18 hours, 8 to 16 hours, 8 to 14 hours, 10 to 16 hours, 10 to 14 hours, etc. within the above range, but it is not limited thereto.

Thereafter, the reaction product may be washed and dried to obtain porous silica particles and, if necessary, unreacted material may be isolated before washing, which may be performed, for example, by separating the supernatant through centrifugation.

The centrifugation may be implemented, for example, at 6,000 to 10,000 rpm, for example, for 3 to 60 minutes, specifically, 3 to 30 minutes, 5 to 30 minutes, etc. within the above range, but it is not limited thereto.

The washing may be carried out with water and/or an organic solvent. In particular, since different substances are soluble in different solvents, respectively, water and the organic solvent may be used once or several times by turns. Alternatively, water and/or the organic solvent may be used alone for washing once or several times. Such several times may include, for example, two or more, ten or less, specifically, three or more and ten or less, four or more and eight or less, four or more and six or less, etc.

The organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; carbon-based aromatics such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (CELLOSOLVE) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; and dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethyl phosphoamide, tetramethylurea, N-methylcarrolactam, tetrahydrofuran, m-dioxane, p-dioxane, 1,2-dimethoxyethane, etc., and, specifically, alcohol and, more specifically, ethanol may be used, but it is not limited thereto.

The washing may be performed under centrifugation, for example, at 6,000 to 10,000 rpm, for example, for 3 to 60 minutes, specifically, 3 to 30 minutes, 5 to 30 minutes, etc. within the above range, but it is not limited thereto.

The washing may be performed by filtering particles with a filter without centrifugation. The filter may include pores with a diameter of less than or equal to the diameter of the porous silica particles. If the reaction solution is filtered through such a filter, only particles remain on the filter and may be washed by pouring water and/or an organic solvent over the filter.

For washing, water and the organic solvent may be used once or several times by turns. Alternatively, the washing may be performed once or several times even with water or the organic solvent alone. The several times may include, for example, two or more and ten or less, specifically, three or more and ten or less, four or more and eight or less, four or more and six or less and the like.

The drying may be performed, for example, at 20 to 100° C., but it is not limited thereto. Alternatively, the drying may be performed in a vacuum state.

Thereafter, the pores of the obtained porous silica particles may be expanded using, for example, a pore swelling agent.

The pore swelling agent used herein may include, for example, trimethylbenzene, triethylbenzene, tripropylbenzene, tributylbenzene, tripentylbenzene, trihexylbenzene, toluene, benzene, etc. and, specifically, trimethylbenzene may be used, but it is not limited thereto.

Alternatively, the pore swelling agent used herein may be, for example, N,N-dimethylhexadecylamine (DMHA), but it is not limited thereto.

Pore expansion described above may be performed, for example, by mixing porous silica particles in a solvent with a pore swelling agent, and heating and reacting the mixture.

The solvent used herein may be, for example, water and/or an organic solvent. The organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; carbon-based aromatics such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; and, specifically, alcohol and, more specifically, ethanol may be used, but it is not limited thereto.

The porous silica particles may be added in a ratio of, for example, 10 to 200 g per liter of solvent, specifically, 10 to 150 g, 10 to 100 g, 30 to 100 g, 40 to 100 g, 50 to 100 g, 50 to 80 g, 60 to 80 g, etc. within the above range, but it is not limited thereto.

The porous silica particles may be evenly dispersed in a solvent, for example, the porous silica particles may be added to the solvent and ultrasonically dispersed therein. In the case of using a mixed solvent, the second solvent may be added after the porous silica particles are dispersed in the first solvent.

The pore swelling agent may be added in an amount of, for example, 10 to 200 parts by volume (vol. parts), specifically, 100 to 150 vol. parts, 10 to 100 vol. parts, 10 to 80 vol. parts, 30 to 80 vol. parts, 30 to 70 vol. parts based on 100 vol. parts of solvent within the above range, but it is not limited thereto.

The reaction may be performed, for example, at 120 to 180° C., specifically, 120 to 170° C., 120 to 160° C., 120 to 150° C., 130 to 180° C., 130 to 170° C., 130 to 160° C., 130 to 150° C., etc. within the above range, but it is not limited thereto.

The reaction may be performed, for example, for 24 to 96 hours, specifically, 30 to 96 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, etc. within the above range, but it is not limited thereto.

By adjusting the time and the temperature within the above ranges, respectively, the reaction may be performed sufficiently without being too much. For example, when the reaction temperature is lower, the reaction time may be increased, otherwise, when the reaction temperature is lower, the reaction time may be shortened. If the reaction is not sufficient, pore expansion may not be sufficient. On the other hand, if the reaction proceeds excessively, the particles may collapse due to the expansion of the pores.

The reaction may be performed, for example, while gradually increasing the temperature. Specifically, the reaction may be performed while gradually increasing the temperature at a rate of 0.5 to 15° C./min from the room temperature, specifically, 1 to 15° C./min, 3 to 15° C./min, 3 to 12° C./min, 3 to 10° C./min, etc. within the above range, but it is not limited thereto.

After the reaction, the reaction solution may be cooled slowly, for example, cooled by lowering the temperature step by step. Specifically, the reaction solution may be cooled by gradually decreasing the temperature at a rate of 0.5 to 20° C./min to room temperature, specifically, 1 to 20° C./min, 3 to 20° C./min, 3 to 12° C./min, 3 to 10° C./min, etc. within the above range, but it is not limited thereto.

After cooling, the reaction product may be washed and dried to obtain porous silica particles having expanded pores. If necessary, unreacted material may be isolated prior to washing, for example, by centrifugation to separate a supernatant.

The centrifugation may be performed, for example, at 6,000 to 10,000 rpm for 3 to 60 minutes, specifically, 3 to 30 minutes, 5 to 30 minutes, etc. within the above range, but it is not limited thereto.

The washing may be carried out with water and/or an organic solvent. In particular, since different substances are soluble in different solvents respectively, water and the organic solvent may be used once or several times by turns. Alternatively, water and/or the organic solvent may be used alone for washing once or several times. Such several times may include, for example, two or more, ten or less, specifically, three times, 4 times, 5 times, 6 times, 7 times, 8 times, etc.

The organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; carbon-based aromatics such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; specifically, alcohol, more specifically, ethanol may be used, but it is not limited thereto.

The washing may be carried out under centrifugation, for example at 6,000 to 10,000 rpm, for example, for 3 to 60 minutes, specifically, 3 to 30 minutes, 5 to 30 minutes, etc. within the above range, but it is not limited thereto.

The washing may be performed by filtering particles with a filter without centrifugation. The filter may have pores with a diameter of less than or equal to the diameter of the porous silica particles. If the reaction solution is filtered through such a filter, only particles remain on the filter and may be washed by pouring water and/or an organic solvent over the filter.

For washing, water and the organic solvent may be used once or several times by turns. Alternatively, the washing may be performed once or several times even with water or the organic solvent alone. The several times may include, for example, two or more and ten or less, specifically, three or more and ten or less, four or more and eight or less, four or more and six or less and the like.

The drying may be performed, for example, at 20 to 100° C., but it is not limited thereto. Alternatively, the drying may be performed in a vacuum state.

Thereafter, the pores of the obtained porous silica particles may be subjected to calcinations, which is a process of heating the particles to have a denser structure on the surface thereof and the inside of the pore, and removing organic materials filling the pores. For example, the calcinations may be performed at 400 to 700° C. for 3 to 8 hours, specifically, at 500 to 600° C. for 4 to 5 hours, but it is not limited thereto.

Then, the obtained porous silica particles may be modified on the surface and/or the inside of the pore as described above.

The surface modification may be performed on the surface of the particle and/or the inside of the pore. The surface of the particle and the inside of the pore may be surface-modified in the same manner or differently.

The particles may be charged or have hydrophilic and/or hydrophobic properties through surface modification. The surface modification may be performed, for example, by reacting a compound having a hydrophilic, hydrophobic, cationic or anionic substituent to be introduced, with the particles. In this regard, the compound may include, for example, alkoxysilane having a C1 to C10 alkoxy group, but it is not limited thereto. The alkoxysilane may have at least one alkoxy group, specifically, 1 to 3 alkoxy groups, and may have a substituent to be introduced into a site in which the alkoxy group is not bonded or a substituent substituted with the alkoxy group.

When the alkoxysilane is reacted with the porous silicon particles, an alkoxysilane can be bonded to the surface of the porous silica particle and/or the inside of pore through a covalent bond between a silicon atom and an oxygen atom. Further, since the alkoxysilane has a substituent to be introduced, this substituent may be introduced into the surface of the porous silica particle and/or the inside of the pore.

The above reaction may be performed by reacting the porous silica particles dispersed in a solvent with alkoxysilane.

Water and/or organic solvents may be used as the solvent, and the organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; carbon-based aromatics such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (CELLOSOLVE) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; and dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethyl phosphoamide, tetramethylurea, N-methylcarrolactam, tetrahydrofuran, m-dioxane, p-dioxane, 1,2-dimethoxyethan and the like. Specifically, alcohol, more specifically, methanol may be used, but it is not limited thereto.

The positively charging may be performed by reacting the particles with, for example, alkoxysilane having a basic group, that is, a nitrogen-containing group such as amino, aminoalkyl, etc. Specifically, N-[3-(trimethoxysilyl)propyl]ethylenediamine, N1-(3-trimethoxysilylpropyl)diethylenetriamine, (3-aminopropyl)trimethoxysilane, N-[3-(trimethoxysilyl)propyl]aniline, trimethoxy[3-(methylamino)propyl]silane, 3-(2-aminoethylamino)propyldimethoxymethylsilane, etc. may be used, but it is not limited thereto.

The negatively charging may be performed by reacting the particles with, for example, alkoxysilane having an acidic group such as carboxyl, sulfonic acid, thiol, etc. Specifically, (3-mercaptopropyl)trimethoxysilane may be used, but it is not limited thereto.

The hydrophilic property may be obtained by reacting the particles with, for example, alkoxysilane having a hydrophilic group such as hydroxyl, carboxyl, amino, carbonyl, sulfhydryl, phosphate, thiol, ammonium, ester, imide, thioimide, keto, ether, indene, sulfonyl, polyethyleneglycol, etc. Specifically, N-[3-(trimethoxysilyl) propyl]ethylenediamine, N1-(3-trimethoxysilylpropyl)diethylenetriamine, (3-aminopropyl)trimethoxysilane, (3-mercaptopropyl)trimethoxysilane, trimethoxy[3-(methylamino)propyl]silane, 3-(2-aminoethylamino)propyldimethoxymethylsilane, etc. may be used, but it is not limited thereto.

The hydrophobic property may be obtained by reacting the particles with, for example, alkoxysilane having a hydrophobic substituent such as substituted or unsubstituted $C_1$ to $C_{30}$ alkyl, substituted or unsubstituted $C_3$ to $C_{30}$ cycloalkyl, substituted or unsubstituted $C_6$ to $C_{30}$ aryl, substituted or unsubstituted $C_2$ to $C_{30}$ heteroaryl, halogen, $C_1$ to $C_{30}$ ester, and halogen-containing groups, etc. Specifically, trimethoxy(octadecyl)silane, trimethoxy-n-octylsilane, trimethoxy(propyl)silane, isobutyl(trimethoxy)silane, trimethoxy(7-octen-1-yl)silane, trimethoxy(2-phenylethyl)silane, vinyltrimethoxysilane, cyanomethyl, 3-[(trimethoxysilyl)propyl]trithiocarbonate and (3-bromopropyl)trimethoxysilane, etc. may be used, but it is not limited thereto.

For improvement of the binding force between the particles and a poorly soluble (hydrophobic) bioactive material through surface modification, an additional process may be further included so that a hydrophobic substituent is present inside the pore while a hydrophilic substituent is present on the surface of the particle, in consideration of easiness in use and formulation of the composition according to the present invention. Further, a substituent for binding another material other than the bioactive material to the surface of the particle may be further provided.

Further, the surface modification may be performed in combination. For example, two or more surface modification may be performed on the outer surface of the particle or inside the pore. As a specific example, a compound containing a carboxyl group may be bonded to an amide-introduced silica particle through amide bond to change positively charged particles to have different surface characteristics, but it is not limited thereto.

The reaction of the porous silica particles with alkoxysilane may be performed, for example, under heating.

The heating may be performed at 80 to 180° C., for example, in a range of 80 to 160° C., 80 to 150° C., 100 to 160° C., 100 to 150° C., 110 to 150° C., etc., but it is not limited thereto.

The reaction of the particles with alkoxysilane may be implemented for 4 to 20 hours, for example, in a range of 4 to 18 hours, 4 to 16 hours, 6 to 18 hours, 6 to 16 hours, 8 to 18 hours, 8 to 16 hours, 8 to 14 hours, 10 to 14 hours, etc., but it is not limited thereto.

A reaction temperature, time, and the amount of the compound used for surface modification may be selected depending on a desired extent of surface modification. Further, varying reaction conditions depending on hydrophilicity, hydrophobicity and a charge level of the bioactive material may regulate hydrophilicity, hydrophobicity and charge level of the silica particles, thereby controlling the release rate of the bioactive material. For example, if the bioactive material has strong negative charge at neutral pH, the reaction temperature may be increased, the reaction time may be extended, or an amount of the compound to be treated may also be increased so that the porous silica particles have strong positive charge, but it is not limited thereto.

Further, the porous silica particles may be manufactured by, for example, preparation of small pore particles, expansion of pores, surface modification, modification of inside of the pore and the like.

Preparation of the small pore particles and pore expansion may be performed by the processes described above, and the washing and drying processes may be performed after the preparation of the small pore particles and after the pore expansion.

If necessary, isolation of the unreacted material may be preceded by washing, for example, conducted by separating the supernatant through centrifugation.

The centrifugation may be performed at, for example, 6,000 to 10,000 rpm, for example, for 3 to 60 minutes, specifically, 3 to 30 minutes, 5 to 30 minutes, etc. within the above range, but it is not limited thereto.

The washing after the preparation of the small pore particles may be performed by any method under conditions within the above-illustrated range, but it is not limited thereto.

The washing after the pore expansion may be performed under more relaxed conditions than the above illustrative embodiments. For example, washing may be carried out three times or less, but it is not limited thereto.

The surface of the particle and/or the inside of the pore may be modified by the above-described method, wherein the modification may be performed in an order of the surface of the particle and then the inside of the pore, and particle washing may be further performed between the above two processes.

When the washing is carried out in more relaxed conditions after the preparation of small pore particles and pore expansion, the pores are filled with a reaction solution such as a surfactant used in the particle preparation and the pore expansion, such that the inside of the pore is not modified during surface modification, instead, only the surface of the particle may be modified. After then, washing the particles may remove the reaction solution in the pores.

Particle washing between surface modification and modification of the inside of the pore may be performed with water and/or an organic solvent. In particular, since different substances are soluble in different solvents respectively, water and the organic solvent may be used once or several times by turns. Alternatively, water and/or the organic solvent may be used alone for washing once or several times. Such several times may include, for example, two or more, ten or less, specifically, three or more and ten or less, four or more and eight or less, four or more and six or less, etc.

The washing may be performed under centrifugation, for example, at 6,000 to 10,000 rpm, for example, for 3 to 60 minutes, specifically, 3 to 30 minutes, 5 to 30 minutes, etc. within the above range, but it is not limited thereto.

The washing may be performed by filtering particles with a filter without centrifugation. The filter may include pores with a diameter of less than or equal to the diameter of the porous silica particles. If the reaction solution is filtered through such a filter, only particles remain on the filter and may be washed by pouring water and/or an organic solvent over the filter.

For washing, water and the organic solvent may be used once or several times by turns. Alternatively, the washing may be performed once or several times even with water or the organic solvent alone. The several times may include, for example, two or more and ten or less, specifically, three or more and ten or less, four or more and eight or less, four or more and six or less and the like.

The drying may be performed, for example, at 20 to 100° C., but it is not limited thereto. Alternatively, the drying may be performed in a vacuum state.

The bioactive material such as siRNA or dsRNA of the present invention may be loaded on the surface of the particle and/or the inside of the pore.

The loading may be implemented, for example, by mixing the porous silica particles and the bioactive material in a solvent.

Water and/or organic solvents may be used as the solvent, and the organic solvent used herein may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; carbon-based aromatics such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc. and the like.

Further, a phosphate buffered saline solution (PBS), simulated body fluid (SBF), borate-buffered saline, tris-buffered saline may be used as the solvent.

A ratio of the porous silica particles and the bioactive material is not particularly limited and, for example, the weight ratio may be 1:0.05 to 0.8, specifically, 1:0.05 to 0.7, 1:0.05 to 0.6, 1:0.1 to 0.8, 1:0.1 to 0.6, 1:0.2 to 0.8, 1:0.2 to 0.6, etc. within the above range.

The bioactive material such as siRNA or dsRNA of the present invention loaded on the porous silica particles may be gradually released over an extended period of time. Such slow release may be continuous or non-continuous, or linear or non-linear, and may vary due to the characteristics of the porous silica particles and/or interaction thereof with the bioactive material.

The bioactive material loaded on the porous silica particles is released while the porous silica particles are biodegraded. More particularly, the porous silica particles according to the present invention may be slowly degraded to release the loaded bioactive material in a sustained manner. Such release may be controlled by, for example, adjusting the surface area, particle diameter, pore diameter, substituents on the surface of the particle and/or the inside of pore, compactness of the porous silica particles, and the like, but it is not limited thereto.

In addition, the bioactive material loaded on the particles may be released while being separated from the porous silica particles and diffused, which is affected by the relationship between the porous silica particles, the bioactive material and the bioactive material releasing environment. Therefore, adjusting these conditions may control the release of bioactive material. For example, the release of bioactive material may be controlled by strengthening or weakening the binding force of the porous silica particles with the bioactive material by surface modification.

More particularly, if the loaded bioactive material is poorly water-soluble (hydrophobic), the surface of the particle and/or the inside of the pore may have a hydrophobic substituent to increase the binding force between the particles and the bioactive material, whereby the bioactive material may be released in a sustained manner. This may be achieved by, for example, surface modification of the particles with alkoxysilane having a hydrophobic substituent.

As used herein, "poorly soluble" means being insoluble (practically insoluble) or only slightly soluble (with respect to water), which is a terminology defined in "pharmaceutical Science" $18^{th}$ Edition (U.S.P, Remington, Mack Publishing Company).

The poorly water-soluble bioactive material may have, for example, water solubility of less than 10 g/L, specifically less than 5 g/L, more specifically less than 1 g/L at 1 atmosphere and 25° C., but it is not limited thereto.

When the loaded bioactive material is water-soluble (hydrophilic), the surface of the particle and/or the inside of the pore may have a hydrophilic substituent to increase the binding force between the porous silica particles and the bioactive material, whereby the bioactive materials may be released in a sustained manner. This may be achieved by, for example, surface modification of the porous silica particles with alkoxysilane having a hydrophilic substituent.

The water-soluble bioactive material may have, for example, water solubility of 10 g/L or more at 1 atmosphere and 25° C., but it is not limited thereto.

When the loaded bioactive material is charged, the surface of the particle and/or the inside of the pore may be charged with the opposite charge thus to increase the binding force between the porous silica particles and the bioactive material, whereby the bioactive material may be released in a sustained manner. This may be achieved by, for example, surface modification of the porous silica particles with alkoxysilane having an acidic group or a basic group.

Specifically, if the bioactive material is positively charged at neutral pH, the surface of the particle and/or the inside of the pore may be negatively charged at neutral pH thus to increase the binding force between the porous silica particles and the bioactive material, whereby the bioactive material may be released in a sustained manner. This may be achieved by, for example, surface modification of the porous silica particles with alkoxysilane having an acidic group such as a carboxyl group (—COOH), sulfonic acid group (—SO₃H), etc.

Further, if the bioactive material is negatively charged at neutral pH, the surface of the particle and/or the inside of the pore may be positively charged thus to increase the binding force between the porous silica particles and the bioactive material, whereby the bioactive material may be release in a sustained manner. This may be achieved by, for example, surface modification of the porous silica particles with alkoxysilane having a basic group such as an amino group, nitrogen-containing group, etc.

The loaded bioactive material may be released for a period of, for example, 7 days to 1 year or more depending on the type of treatment required, release environment, and porous silica particles to be used, etc.

Since the porous silica particles are biodegradable and may be degraded by 100%, the bioactive material loaded thereon can be released by 100%.

The pharmaceutical composition for preventing or treating liver cancer, which includes siRNA or dsRNA of the present invention, may further include pharmaceutically acceptable carrier and may be formulated together with the same. As used herein, the term "pharmaceutically acceptable carrier" refers to a carrier or diluent that does not irritate an organism and does not inhibit biological activities and properties of the administered compound. The pharmaceutically acceptable carrier in a composition formulated in a liquid solution is sterile and physiologically compatible, and may include saline, sterile water, Ringer's solution, buffered saline, albumin injectable solution, dextrose solution, maltodextrin solution, glycerol, ethanol, and a combination of one or more of these components. Further, if necessary, other conventional additives such as antioxidants, buffers and bacteriostatic agents may also be added thereto. In addition, diluents, dispersants, surfactants, binders and lubricants may also be added so as to formulate the composition into injectable formulations such as aqueous solution, suspension, emulsion, etc., pills, capsules, granules or tablets and the like.

The composition of the present invention is applicable in any type of formulation that contains the siRNA or dsRNA of the present invention as an active ingredient, and may be prepared in oral or parenteral formulations. Such pharmaceutical formulations of the invention may include any one suitable for oral, rectal, nasal, topical (including the cheek and sublingual), subcutaneous, vaginal or parenteral (intramuscular, subcutaneous) administration, or otherwise, may be suitable for administration through inhalation or insufflation.

The composition of the present invention may be administered in a pharmaceutically effective amount. An effective dose level may be determined in consideration of the type of disease, severity, activity of the drug, sensitivity to the drug, administration time, administration route and rate of release, duration of treatment, factors including concurrent drug use, and other factors well known in the medical field. The composition of the present invention may be administered as a separate therapeutic agent or in combination with other therapeutic agents, may be administered sequentially or simultaneously with conventional therapeutic agents, and may be administered in single or multiple doses. Taking all of the above factors into consideration, it is important to administer a minimum amount that can obtain maximum effects without side effects, which can be easily determined by those skilled in the art.

Dosage of the composition of the present invention may vary greatly depending on a weight, age, gender and/or health condition of a patient, diet, administration time, method of administration, excretion rate and severity of the disease. Specifically, an appropriate dosage may depend on the amount of drug accumulated in the body and/or specific efficacy of the siRNA or dsRNA of the present invention to be used. In general, the dosage may be estimated based on EC50 determined to be effective in in vivo animal models as well as in vitro. For example, the dosage may range from 0.01 μg to 1 g per kg of body weight, and the composition may be administered once or several times per unit period, in daily, weekly, monthly or yearly unit periods. Otherwise, the composition may be continuously administered for a long period of time via an infusion pump. The number of repeated doses is determined in consideration of a retention time of drug remaining in the body, a concentration of drug in the body and the like. Even after the treatment in the course of the disease treatment, the composition may be administered for preventing relapse.

The composition of the present invention may further include at least one active ingredient having the same or similar function in relation to treatment of liver cancer or a compound which maintains/increases solubility and/or absorbency of the active ingredient. Further, chemotherapeutic agents, anti-inflammatory agents, antiviral agents and/or immune-modulators, etc. may be optionally included.

In addition, the composition of the present invention may be formulated by any conventional method known in the art to provide rapid, sustained or delayed release of the active ingredient after the administration thereof to a mammal. The formulation may be in a form of powders, granules, tablets, emulsions, syrups, aerosols, soft or hard gelatin capsules, sterile injectable solutions, sterile powders.

Hereinafter, the present invention will be described in detail with reference to the following examples.

Example 1—Experimental Materials and Methods

1. Cell Culture

Human liver cancer cell line (SNU-449) and murine Hepa-1c1c7 liver cancer cell line were obtained from Korean Cell Line Bank (Seoul, Korea). All of the cell lines were cultured in EMEM (American Type Culture Collection, Manassas, VA), RPMI-1640 or DMEM medium (Lonza, Walkersville, MD) which is supplemented with 10% fetal bovine serum (FBS, Lonza) and 100 units/mL penicillin-streptomycin (Invitrogen, Carlsbad, CA), in a humidified incubator at 37° C. under 5% $CO_2$ condition.

2. Synthesis and Transfection of siRNA and dsRNA

The siRNA and dsRNA used in this experiment were synthesized by Lemonex (Seoul, Korea). Further, human BANF1, PLOD3 and SF3B4 expression plasmids subcloning gene ORF sequences (BANF1:NM_003860, PLOD3: NM_001084, SF3B4: NM_005850) in pcDNA3.1+/C-(K)-DYK plasmid, respectively, were purchased from Genscript™ (Piscataway, NJ, USA). Transfection was performed using Lipofectamine RNAiMAX or Lipofectamine 2000 reagent (Invitrogen) according to the manufacturer's manual.

3. Extraction of RNA and DNA, and Execution of RT-PCR and qRT-PCR

Total RNA was isolated from frozen tissue and cells using trizol reagent (Invitrogen). 1 μg of total RNA was reverse-transcribed with cDNA by Tetro cDNA synthesis kit (Bioline, London, UK) according to the manufacturer's manual. RT-PCR reactions were conducted with nTaq DNA polymerase (Enzynomics, Taejon, Korea), followed by detection using ethidium bromide in a Gel Doc XR imaging system (Bio-Rad, Hercules, Calif.). qRT-PCR was performed by SensiFAST SYBR No-ROX Kit (Bioline) and was monitored in real time by iQ™-5 (Bio-Rad). An average Ct (threshold cycle) acquired from three replicate experiments was used for the calculation. Normalized gene expression was determined using a relative quantification method. The results were expressed as an average value of three replicate experiments. Genomic DNA from tissues and cells was isolated using DNAzol reagent (Invitrogen) according to the manual. For analysis of replication number variation, the SF3B4 genomic DNA region was amplified from 20 pairs (non-tumor and tumor) HCC tissues using a primer set from exon-1 to intron-1 according to the genome sequence of Genbank accession No. NC_000001.11. qRT-PCR was performed as described above, and glyceraldehyde-3-phosphate dehydrogenase was used as an endogenous loading control. The primer sequences used for RT-PCR and qRT-PCR are shown in Table 5 below.

TABLE 5

| Gene | Accession No. | Primer | Nucleotide sequence | SEQ ID NO |
|---|---|---|---|---|
| BANF1 | NM_003860 | Forward | 5'-GAACCGTTACGGGAACTGAA-3' | SEQ ID NO: 316 |
|  |  | Reverse | 5'-CCCGGAAGAGGTCTTCATCT-3' | SEQ ID NO: 317 |
| PLOD3 | NM_001084 | Forward | 5'-CAGCTCCAGGACCACTTCTC-3' | SEQ ID NO: 318 |
|  |  | Reverse | 5'-GAGCGGGCGTAGTACTCATC-3' | SEQ ID NO: 319 |
| SF3B4 | NM_005850 | Forward | 5'-CTCAGATGCAGCTTGCACAC-3' | SEQ ID NO: 320 |
|  |  | Reverse | 5'-GGAGGGCCAGTGTATCCAT-3' | SEQ ID NO: 321 |
| GAPDH | NM_002046 | Forward | 5'-ACCAGGTGGTCTCCTCTGAC-3' | SEQ ID NO: 322 |
|  |  | Reverse | 5'-TGCTGTAGCCAAATTCGTTG-3' | SEQ ID NO: 323 |

4. Cell Growth and Proliferation Assay

Cell lines were seeded in 12-well plates at 30% confluence for cell growth assay. After transfection or inhibitor treatment, cells were incubated with 0.5 mg/mL of MTT (3-(4,5-dimethylthiazol-2-yl)-2,5-diphenyltetrazolium bromide) for 1 h at 37° C. every 24 hours. The formazan crystal was dissolved with dimethyl sulfoxide (DMSO), and absorbance was read at 570 nm using VICTOR3™ multilabel plate reader (PerkinElmer, Boston, MA).

Cell lines were seeded in 24-well plates at 30% confluence for cell proliferation assay. After transfection, cells were treated with 5-bromo-2'-deoxyuridine (BrdU) reagent for 2 h and fixed at room temperature for 30 min. Cells were incubated with anti-BrdU antibody for 1 h at room temperature. Unbound antibody was removed by washing buffer. Horseradish peroxidase-conjugated secondary antibody was added to each well. The substrate solution was added and the reaction was stopped with stop solution after 30 min. The final product was quantified at 490 nm by VICTOR3™ multilabel plate reader (PerkinElmer).

5. Cell Motility and Invasion Assay

For in vitro cell motility and invasion assays, Transwell plates and cell culture inserts (BD Biosciences) were used. For the coating of the invasion assay, Matrigel (BD Biosciences) was diluted to 0.3 mg/ml concentration with coating buffer (0.01 M Tris, 0.7% NaCl, pH 8.0) and 100 µl Matrigel was coated onto the upper compartment of the cell culture insert. After incubation for 1 h at 37° C., the cell culture insert was ready for seeding. After si-SF3B4 transfection, cells were appropriately seeded ($0.5 \times 10^5$ cells/well for the motility assay, $1 \times 10^5$ cells/well for the invasion assay) into the cell culture insert with serum-free medium in the presence of 5% FBS as chemoattractant. After incubation for 6 h (migration assay) or 12 h (invasion assay) at 37° C., migrated or invaded cells were stained using Diff-Quik staining kit (Sysmex, Japan). Cells were photographed using an Axiovert 200 inverted microscope (Zeiss, Jena, Germany) at ×200 magnification. Cells were enumerated in three random fields of view.

6. Wound Healing Assay

Transfected cells were seeded in wells of a 6-well plate. At 100% confluence, a scratch was made on a uniform layer using a micropipette tip. Photographs of the same area of the wound were taken after 0 and 24 h with IX70 fluorescence inverted microscope (Olympus, Tokyo, Japan).

7. Mouse Liver Cancer Model

For xenograft tumorigenesis assay, $1 \times 10^7$ cells of transfected cells were mixed with 0.2 ml PBS (pH 7.4) and 30% (v/v) Matrigel matrix (BD Biosciences). Cell suspensions were subcutaneously injected in 6-week-old male Balb/c-nude mice. Mice were examined twice per week for tumor formation at the injection sites. Tumor volumes were calculated using: $0.5 \times$length (L)$\times$width$^2$ (W$^2$). Each experimental group consisted of 10 mice and tumor growth was quantified by measuring tumor sizes in three orthogonal direction using calipers. Results are expressed as mean tumor volumes and 95% confidence interval. The H-ras12V activated homozygous transgenic mice were kindly provided by Dr. Dae-Yeoul Yu (Laboratory of Human Genomics, Korea Research Institute of Bioscience and Biotechnology, Daejeon, Korea). Transgenic mice were H-ras12V activated. Male mice spontaneously developed HCC beginning at 15-weeks-of-age. We surgically obtained the non-tumor region and HCC mass from five mice (35-weeks-old)

and pick out three pairs of HCC tissue by pathological scoring. Diethylnitrosamine (DEN) was used to induce HCC.

8. Porous Silica Particles (Mesoporous Nanoparticles) Transfection siRNA specific to BANF1, PLOD3, SF3B4 was loaded in 80 μl of 3 nmol InViVojection™ RNAi-nano reagent (the porous silica nanoparticles in Example 1-12(1)-2)-(ii), Cat. No. DHMSN-vivoRNA; Lemonex Inc., Seoul, Korea) and prepared in 200 μl of PBS. A mixture of siRNA or dsRNA and nanoparticles was intravenously injected into H-ras transgenic HCC mouse model through tail vein every week from week 9 to week 23. Sonograms (ultrasonic photographs) were taken at 17, 19, and 21 weeks by an ultrasonic machine (Affiniti 50, Philips, Seoul, Korea).

9. Western Blotting Analysis

Cells were dissolved in a protein extraction buffer (50 mM HEPES, 5 mM EDTA, 50 mM NaCl, 1% Triton X-100, 50 mM NaF, 10 mM $Na_2P_2O_7$, 1 mM $Na_3VO_4$, 100× Halt protease inhibitor cocktail). Lysate containing the same amount of protein was separated by SDS-PAGE and transferred onto a polyvinylidene fluoride (PVDF) membrane (Bio-Rad). The blots were blocked with 5% skim milk and incubated along with each antibody (Table 6).

TABLE 6

| Protein | Manufacturer | Catalog No. | Dilution |
|---|---|---|---|
| BANF1 | Santa Cruz | sc-33787 | 1:200 |
| PLOD3 | Proteintech | 11027-1-AP | 1:1000 |
| SF3B4 | Abcam | ab157117 | 1:1000 |
| E-cadherin | BD Biosciences | 610404 | 1:1000 |
| N-cadherin | BD Biosciences | 610920 | 1:1000 |
| Fibronectin | Santa Cruz | sc-9068 | 1:1000 |
| Snail | Abcam | ab78105 | 1:1000 |
| Slug | Cell Signaling | #9585 | 1:500 |
| GAPDH | Santa Cruz | sc-32233 | 1:1000 |

10. Statistical Analysis

Survival curves were plotted using the Kaplan-Meier product limit method, and significant differences between survival curves were determined using the log-rank test. All experiments were performed at least three times, and all samples were analyzed in triplicate. Results are presented as mean±standard deviation (SD) or standard error of the mean (SEM). The statistical significance of the difference between experimental groups was assessed by paired or unpaired student's t-tests using Graphpad™ 7.0 software. Statistical significance was determined for $p<0.05$. Chi-square test (2-sided) was used to determine associations between parameters 11. Preparation of Porous Silica Particles (Mesoporous Nanoparticles)

(1) Preparation of Particle 1

1) Preparation of Small Pore Particles

A 2 L round bottom flask was charged with 960 ml of distilled water (DW) and 810 ml of MeOH. 7.88 g of CTAB was added to the flask and 4.52 ml of 1 M NaOH was rapidly added with agitating. The mixture was agitated for 10 minutes to give a homogeneously mixed solution, and 2.6 ml of TMOS was added thereto. The mixture was homogenously mixed under agitation for 6 hours and then aged for 24 hours.

Then, the reaction solution was centrifuged at 8000 rpm and 25° C. for 10 minutes to remove the supernatant. During centrifugation at 8000 rpm and 25° C., the product was washed five times with ethanol and distilled water by turns.

Thereafter, the resultant product was dried in an oven at 70° C. to obtain 1.5 g of powdery small pore silica particles (average pore diameter: 2 nm, particle diameter: 200 nm).

2) Pore Expansion 1.5 g of small pore silica particle powders were added to 10 ml of ethanol, followed by ultrasonic dispersion.

Further, 10 ml of water and 10 ml of trimethyl benzene (TMB) were added thereto, followed by ultrasonic dispersion.

Thereafter, the dispersion was placed in an autoclave and reacted at 160° C. for 48 hours.

The reaction started at 25° C. and proceeded with heating at a rate of 10° C./min, followed by cooling down at a rate of 1 to 10° C./min in an autoclave.

The cooled reaction solution was centrifuged at 8000 rpm and 25° C. for 10 minutes to remove the supernatant. During centrifugation at 8000 rpm and 25° C. for 10 minutes, the product was washed five times with ethanol and distilled water by turns.

Thereafter, the resultant product was dried in an oven at 70° C. to obtain powdery porous silica particles (pore diameter: 10 to 15 nm, particle size: 200 nm).

3) Calcinations

The porous silica particles prepared in the above 2) were placed in a glass vial and heated at 550° C. for 5 hours. After the completion of the reaction, the particles were gradually cooled to room temperature, thereby preparing particles.

(2) Preparation of Particle 2

Porous silica particles were prepared in the same manner as in Example 1-11(1), except that the reaction conditions at the time of pore expansion were changed to 140° C. and 72 hours.

(3) Preparation of Particle 3 (10 L Scale)

Porous silica particles were prepared in the same manner as in Example 1-11(1), except that 5-fold larger vessels were used and all the materials were used in a 5-fold capacity.

(4) Preparation of Particle 4 (Particle Diameter: 300 nm)

Porous silica particles were prepared in the same manner as in Example 1-11(1), except that 920 ml of distilled water and 850 ml of methanol were used in the preparation of small pore particles.

(5) Preparation of Particle 5 (Particle Diameter: 500 nm)

Porous silica particles were prepared in the same manner as in Example 1-11(1), except that 800 ml of distilled water, 1010 ml of methanol and 10.6 g of CTAB were used in the preparation of small pore particles.

(6) Preparation of Particle 6 (Particle Diameter: 1000 nm)

Porous silica particles were prepared in the same manner as in Example 1-11(1), except that 620 ml of distilled water, 1380 ml of methanol and 7.88 g of CTAB were used in the preparation of small pore particles.

(7) Preparation of Particle 7 (Pore Diameter: 4 nm)

Porous silica particles were prepared in the same manner as in Example 1-11(1), except that 2.5 ml of TMB was used at the time of pore expansion.

(8) Production of Particle 8 (Pore Diameter: 7 nm)

Porous silica particles were prepared in the same manner as in Example 1-11(1), except that 4.5 ml of TMB was used at the time of pore expansion.

(9) Preparation of Particle 9 (Pore Diameter: 17 nm)

Porous silica particles were prepared in the same manner as in Example 1-11(1), except that 11 ml of TMB was used at the time of pore expansion.

(10) Preparation of Particle 10 (Pore Diameter: 23 nm)

Porous silica particles were prepared in the same manner as in Example 1-11(1), except that 12.5 ml of TMB was used at the time of pore expansion.

(11) Preparation of Particle 11 (Dual Modification)
1) Preparation of Small Pore Particles Small pore particles were prepared in the same manner as in Example 1-11(1).

2) Pore Expansion

The small pore particles were reacted with TMB in the same manner as in Example 1-11(1)-2), cooled, and centrifuged to remove the supernatant. Thereafter, the mixture was centrifuged under the same conditions as in Example 1-11(1)-2), washed three times with ethanol and distilled water by turns, and then dried under the same conditions as in Example 1-11(1)-2), thereby obtaining powdery silica particles (pore diameter: 10 to 15 nm, particle diameter: 200 nm).

3) Surface Modification 0.8 to 1 g of porous silica particles having expanded pores were dispersed in 50 ml of toluene, and then 5 ml of (3-aminopropyl)triethoxysilane was added thereto, followed by heating at 120° C. for 12 hours under reflux. The product was subjected to the washing and drying processes described above and then dispersed along with 1 ml of triethylenegly-col (PEG3, 2-[2-(2-methoxyethoxy)ethoxy]acetic acid), 100 mg of EDC (1-ethyl-3-(3-dimethylaminopropyl)carbodiimide) and 200 mg of N-Hydroxysuccinimide (NHS) in 30 ml of PBS. The dispersion was subjected to reaction with agitating at room temperature for 12 hours. Then, the resultant product was subjected to the above-described washing and drying processes.

Since the reaction solution in the previous step remained in the pores, the insides of the pores were not modified.

4) Washing Inside of Pore 800 mg of the surface-modified particle powders were dissolved in 40 ml of 2 M HCl/ethanol and refluxed with vigorous agitating for 12 hours.

Then, the cooled reaction solution was centrifuged at 8000 rpm for 10 minutes to remove the supernatant. During centrifugation at 8000 rpm and 25° C. for 10 minutes, the product was washed five times with ethanol and distilled water by turns.

Thereafter, the resultant product was dried in an oven at 70° C. to obtain powdery porous silica particles.

5) Modification of Inside of Pore (i) A propyl group was introduced into the pores in the same manner as in Example 1-12(2)-1) described below.

(ii) An octyl group was introduced into the pores in the same manner as in Example 1-12(2)-2) described below.

12. Surface Modification of Porous Silica Particles
(1) Positive Charging
1) Particles Having a Particle Diameter of 300 nm The porous silica particles in Example 1-11(4) were reacted with (3-aminopropyl)triethoxysilane (APTES) thus to be positively charged.

More particularly, 100 mg of porous silica particles were dispersed in 10 ml of toluene in a 100 ml round bottom flask provided with a bath sonicator. Then, 1 ml of APTES was added thereto, and the mixture was reacted for 12 hours with agitation at 400 rpm and 130° C.

After the reaction, the mixture was slowly cooled to room temperature, centrifuged at 8000 rpm for 10 minutes to remove the supernatant. During centrifugation at 8000 rpm and 25° C. for 10 minutes, the product was washed five times with ethanol and distilled water by turns.

Thereafter, the resultant product was dried in an oven at 70° C. to obtain powdery porous silica particles having an amino group on the surfaces of the particles and the insides of pores.

2) Particles Having a Particle Diameter of 200 nm (i) The porous silica particles in Example 1-11(1) were reacted with (3-aminopropyl)triethoxysilane (APTES) thus to be positively charged, and then were modified in the same manner as in Example 1-12(1)-1), except that 0.4 ml of APTES was added and the reaction time was changed to 3 hours.

(ii) The porous silica particles in Example 1-11(9) were reacted with (3-aminopropyl)triethoxysilane(APTES) thus to be positively charged, and then were modified in the same manner as in Example 1-12(1)-1), except that the particles prepared in Example 1-11(9) were used.

(iii) The porous silica particles in Example 1-11(10) were reacted with (3-aminopropyl)triethoxysilane (APTES) thus to be positively charged, and then were modified in the same manner as in Example 1-12(1)-1), except that the particles prepared in Example 1-11(10) were used.

(2) Introduction of Hydrophobic Group
1) Propyl Group

The porous silica particles in Example 1-11(1) were reacted with trimethoxy(propyl)silane to introduce a propyl group into the surfaces of the particles and the insides of the pores, and then were modified in the same manner as in Example 1-12(1), except that 0.35 ml of trimethoxy(propyl) silane was added instead of APTES and the reaction was conducted for 12 hours.

2) Octyl Group

The porous silica particles of Example 1-11(1) were reacted with trimethoxy-n-octylsilane to introduce a propyl group into the surfaces of the particles and the insides of the pores, and then were modified in the same manner as in Example 1-12(1), except that 0.5 ml of trimethoxy-n-octyl-silane was added instead of APTES and the reaction was conducted for 12 hours.

(3) Negative Charging
1) Carboxyl Group

The porous silica particles in Example 1-11(1) were reacted with succinic anhydride thus to be negatively charged, and then were modified in the same manner as in Example 1-12(1)-1), except that dimethyl sulfoxide (DMSO) was used instead of toluene, 80 mg of succinic anhydride was added instead of APTES, followed by agitation at room temperature for 24 hours to conduct the reaction, and DMSO was used instead of distilled water at the time of washing.

2) Thiol Group

Modification was implemented in the same manner as in Example 1-12(1)-1), except that 1.1 ml of MPTES was used instead of APTES.

3) Sulfonic Acid Group 100 mg of the porous silica nanoparticles in Example 1-12(3)-2) were dispersed in 1 ml of 1 M aqueous sulfuric acid solution and 20 ml of 30% aqueous hydrogen peroxide, followed by agitation at room temperature to induce oxidative reaction thus to oxidize a thiol group into a sulfonic acid group. Thereafter, the product was washed and dried in the same manner as in Example 1-12(1)-1).

13. Loading of siRNA or dsRNA on Porous Silica Particles 21 base pair duplex siRNA targeting green fluorescent protein (GFP) synthesized by Bionia Co. Ltd., on request was purchased from the same (Sequence: sense; 5'-GGC-UACGUCCAGGAGCGCACC-3' (SEQ ID NO: 324), antisense; 5'-UGCGCUCCUGGACGUAGCCUU-3' (SEQ ID NO: 325)).

After mixing 10 μg of the porous silica particles in Example 1-12(1)-2)-(ii) and 50 pmol of siRNA were mixed in 1×PBS condition and allowed to be loaded at room temperature for 30 minutes.

Example 2—Analysis of Inhibitory Rate of Indicator Gene Expression by siRNA or dsRNA of the Present Invention According to the experimental procedures in Example 1-1 to 3, indicator genes of siRNA and dsRNA of the present invention (BANF1 variant 1, BANF1 variant 2, PLOD3, and SF3B4) were analyzed, and the results are shown in Tables 7 to 10 below.

Referring to Tables 7 to 10 below, it can be seen that all the siRNAs and dsRNAs of the present invention could inhibited the expression of the indicator genes at high inhibitory rates.

TABLE 7

Verification of validity of siRNA, dsRNA for inhibition of human BANF1, transcript variant 1, mRNA (Gene Bank number: NM_003860.3) expression

| Base SEQ ID NO | Expression inhibitory rate (%) |
|---|---|
| 5 | 87.73 |
| 6 | 79.64 |
| 7 | 82.3 |
| 8 | 76.21 |
| 9 | 89.6 |
| 10 | 83.42 |
| 11 | 73.18 |
| 12 | 85.44 |
| 13 | 69.57 |
| 14 | 77.3 |
| 15 | 82.92 |
| 16 | 91.38 |
| 17 | 84.11 |
| 18 | 88.36 |
| 19 | 87.83 |
| 20 | 67.72 |
| 21 | 82.29 |
| 22 | 63.23 |
| 23 | 76.24 |
| 24 | 87.7 |
| 25 | 62.57 |
| 26 | 72.92 |
| 27 | 65.58 |
| 28 | 72.91 |

TABLE 8

Verification of validity of siRNA, dsRNA for inhibition of human BANF1, transcript variant 2, mRNA (Gene Bank number: NM_001143985.1) expression

| Base SEQ ID NO | Expression inhibitory rate (%) |
|---|---|
| 29 | 92.55 |
| 30 | 91.49 |
| 31 | 86.44 |
| 32 | 77.1 |
| 33 | 73.82 |
| 34 | 76.6 |
| 35 | 88.33 |
| 36 | 82.53 |
| 37 | 81.64 |
| 38 | 68.4 |
| 39 | 79.72 |
| 40 | 91.6 |
| 41 | 87.37 |
| 42 | 53.77 |
| 43 | 86.39 |

TABLE 8-continued

Verification of validity of siRNA, dsRNA for inhibition of human BANF1, transcript variant 2, mRNA (Gene Bank number: NM_001143985.1) expression

| Base SEQ ID NO | Expression inhibitory rate (%) |
|---|---|
| 44 | 68.63 |
| 45 | 83.22 |
| 46 | 78.16 |
| 47 | 73.48 |
| 48 | 68.3 |
| 49 | 85.27 |
| 50 | 88.74 |
| 51 | 92.32 |
| 52 | 74.8 |
| 53 | 84.31 |
| 54 | 64.9 |
| 55 | 74.72 |

TABLE 9

Verification of validity of siRNA, dsRNA for inhibition of human PLOD3 gene sequence (Gene Bank number: NM_001084.4) expression

| Base SEQ ID NO | Expression inhibitory rate (%) |
|---|---|
| 56 | 87.62 |
| 57 | 78.13 |
| 58 | 92.72 |
| 59 | 83.49 |
| 60 | 86.8 |
| 61 | 64.29 |
| 62 | 73.33 |
| 63 | 85.83 |
| 64 | 82.68 |
| 65 | 76.92 |
| 66 | 91.64 |
| 67 | 85.77 |
| 68 | 79.1 |
| 69 | 82.4 |
| 70 | 84.63 |
| 71 | 89.26 |
| 72 | 76.4 |
| 73 | 76.8 |
| 74 | 68.27 |
| 75 | 77.44 |
| 76 | 86.26 |
| 77 | 84.3 |
| 78 | 81.52 |
| 79 | 79.35 |
| 80 | 76.63 |
| 81 | 85.32 |
| 82 | 62.72 |
| 83 | 64.3 |
| 84 | 77.13 |
| 85 | 83.78 |
| 86 | 86.71 |
| 87 | 82.33 |
| 88 | 68.46 |
| 89 | 74.88 |
| 90 | 72.7 |
| 91 | 83.69 |
| 92 | 85.3 |
| 93 | 76.62 |
| 94 | 82.11 |
| 95 | 83.46 |
| 96 | 71.25 |
| 97 | 72.73 |
| 98 | 87.6 |
| 99 | 69.91 |
| 100 | 81.38 |
| 101 | 78.27 |
| 102 | 74.8 |
| 103 | 69.76 |
| 104 | 62.45 |
| 105 | 87.22 |

TABLE 9-continued

Verification of validity of siRNA, dsRNA for inhibition of human PLOD3 gene sequence (Gene Bank number: NM_001084.4) expression

| Base SEQ ID NO | Expression inhibitory rate (%) |
|---|---|
| 106 | 82.7 |
| 107 | 74.5 |
| 108 | 86.25 |
| 109 | 83.7 |
| 110 | 74.13 |
| 111 | 76.29 |
| 112 | 73.52 |
| 113 | 82.86 |
| 114 | 73.52 |
| 115 | 73.71 |
| 116 | 82.55 |
| 117 | 69.72 |
| 118 | 77.8 |
| 119 | 86.49 |
| 120 | 71.3 |

TABLE 10

Verification of validity of siRNA, dsRNA for inhibition of Human SF3B4 gene sequence (Gene Bank number: NM_005850.4) expression

| Base SEQ ID NO | Expression inhibitory rate (%) |
|---|---|
| 121 | 83.71 |
| 122 | 81.83 |
| 123 | 87.62 |
| 124 | 86.39 |
| 125 | 78.64 |
| 126 | 82.7 |
| 127 | 84.25 |
| 128 | 74.11 |
| 129 | 63.36 |
| 130 | 76.25 |
| 131 | 74.32 |
| 132 | 92.19 |
| 133 | 84.72 |
| 134 | 81.3 |
| 135 | 83.4 |
| 136 | 88.63 |
| 137 | 78.25 |
| 138 | 85.1 |
| 139 | 81.68 |
| 140 | 83.57 |
| 141 | 78.33 |
| 142 | 72.45 |
| 143 | 76.72 |
| 144 | 81.36 |
| 145 | 83.2 |
| 146 | 72.41 |
| 147 | 73.64 |
| 148 | 86.77 |
| 149 | 84.8 |
| 150 | 82.56 |
| 151 | 73.12 |
| 152 | 78.66 |
| 153 | 82.5 |
| 154 | 76.63 |
| 155 | 62.95 |
| 156 | 89.6 |
| 157 | 77.2 |

Example 3—Identification of Excellent RNA Delivery by Porous Silica Particles

With respect to Hepa-1c1c7 and SNU-449 cell lines in Example 1, siRNAs, each of which includes a sense RNA having a sequence shown in Table 11 below and an antisense RNA having a complementary sequence thereto, were subjected to in vitro transfection by the methods described in Example 1-2 or 1-8, respectively. Then, expression levels of the corresponding markers of the above siRNAs were measured by Western blotting, and the results are shown in FIG. 1.

Figure 1:
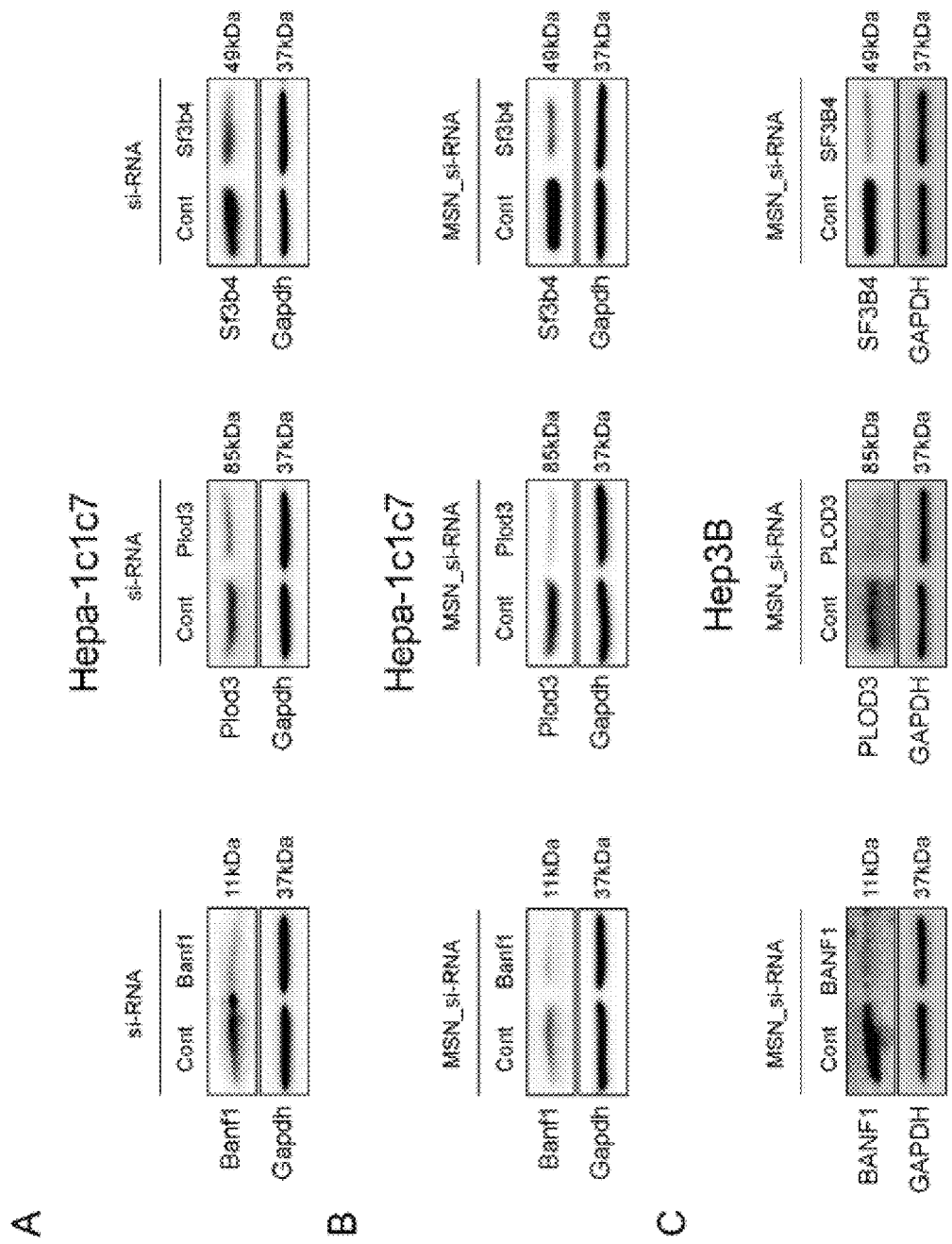
FIG. 1 is views illustrating results of measuring expression levels of indicator factors ("markers") corresponding to siRNAs by Western blotting, respectively, after in vitro transfection of siRNAs to Hepa-1c1c7 and SNU-449 cell lines in Example 1 by methods described in Example 1-2 or 1-8, wherein each siRNA includes a sense RNA having a sequence in Table 11 and an antisense RNA having a complementary sequence to that of the sense RNA.

Referring to FIG. 1, when the siRNAs shown in Table 11 were transfected, it can be seen that the markers were effectively inhibited. Specifically, when siRNA was loaded on the porous silica particles and then transfected, the expression inhibitory rate was demonstrated to be higher.

TABLE 111

| SEQ ID NO | Sense RNA sequence | Name in FIG. 1 | Target gene |
|---|---|---|---|
| SEQ ID NO: 311 | 5'-CCUCAGCGUUUCAAU CUUUUU-3' | Banf1 | Mouse BANF1 gene |
| SEQ ID NO: 312 | 5'-CGACUGCAGAAUCUC CUCUUU-3' | Plod3 | Mouse PLOD3 gene |
| SEQ ID NO: 313 | 5'-CUGCUUUACGAUACU UUCAUU-3' | Sf3b4 | Mouse SF3B4 gene |
| SEQ ID NO: 314 | 5'-CCUACGCCACCAAUU UCGU-3' | Control | — |
| SEQ ID NO: 28 | 5'-AAGAAGCUGGAGGAA AGGGUUU-3' | BANF1 | Human BANF1 gene |
| SEQ ID NO: 119 | 5'-GCAUCUGGAGCUUUC UGUA UU-3' | PLOD3 | Human PLOD3 gene |

TABLE 111-continued

| SEQ ID NO | Sense RNA sequence | Name in FIG. 1 | Target gene |
|---|---|---|---|
| SEQ ID NO: 136 | 5'-GCAGUACCUCUGUAACCGU UU-3' | SF3B4 | Human SF3B gene |

Example 4—Identification of Liver Cancer Cell Metastatic Potential Inhibition by siRNA or dsRNA of the Present Invention

1. Cell Motility and Invasion Assay and Wound Healing Assay

With respect to SNU-449 cell line in Example 1-1, siRNAs, each of which includes a sense RNA having a sequence shown in Table 12 below and an antisense RNA having a complementary sequence thereto, were subjected to in vitro transfection by the method described in Example 1-2. Migration and invasion of markers corresponding to the above siRNAs were analyzed by the method in Example 1-5, while a scratch wound healing ability was analyzed by the method in Example 1-6, and the analyzed results are shown in FIG. 2.

TABLE 12

| SEQ ID NO | Sense RNA sequence | Name in FIG. | Target gene |
|---|---|---|---|
| SEQ ID NO: 314 | 5'-CCUACGCCACCAAUUUC GU-3' | Control | — |
| SEQ ID NO: 28 | 5'-AAGAAGCUGGAGGAAAG GGGUUU-3' | BANF1 | Human BANF1 gene |
| SEQ ID NO: 119 | 5'-GCAUCUGGAGCUUUCUG UA UU-3' | PLOD3 | Human PLOD3 gene |
| SEQ ID NO: 136 | 5'-GCAGUACCUCUGUAACC GU UU-3' | SF3B4 | Human SF3B4 gene |

Figure 2:
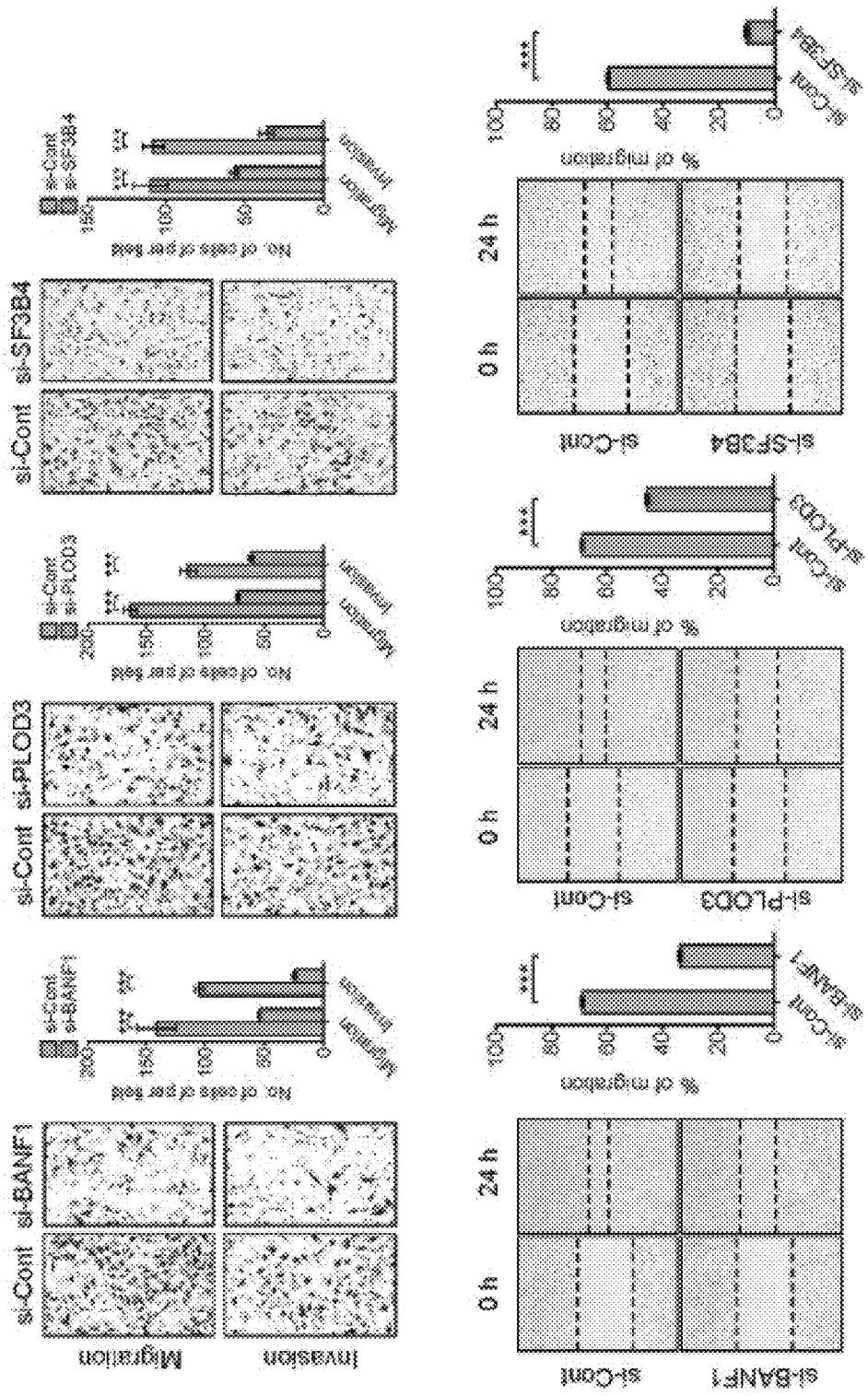
FIG. 2 is views illustrating results of analyzing migration and invasion of markers corresponding to siRNAs by a method described in Example 1-5 and analyzing scratch wound healing ability of the same by a method described in Example 1-6, respectively, after in vitro transfection of siRNAs to SNU-449 cell line in Example 1-1 by a method described in Example 1-2, wherein each siRNA includes a sense RNA having a sequence in Table 12 and an antisense RNA having a complementary sequence to the sequence of the sense RNA.

Referring to A of FIG. 2, it can be seen that, as compared to the control group, the cells with the markers, which were knockdown by transfection of siRNAs listed in Table 12, exhibited significantly reduced migration and invasion. Referring to B of FIG. 2, it was observed that, as compared to the control group, wound-healing ability was considerably decreased. These results demonstrate that the siRNA or dsRNA of the present invention can inhibit metastatic potential of liver cancer cells, while reducing malignant progression.

2. Identification of EMT Regulatory Proteins Inhibition

In order to identify whether siRNA or dsRNA of the present invention can inhibit indicator actors for expression of N-cadherin, Fibronectin, Snail and Slug, which are representative epithelial-mesenchymal transition (EMT) regulatory proteins in relation to the metastasis of liver cancer cells, which in turn can inhibit metastasis of liver cancer, siRNAs, each of which includes a sense RNA having the sequence shown in Table 12 above and an antisense RNA having the complementary sequence thereto, were subjected to in vitro transfection to the SNU-449 cell line in Example 1 by the method described in Example 1-2. Then, expression levels of the markers corresponding to the siRNAs and expression levels of the EMT regulatory proteins above were analyzed by the method in Example 1-9, and the analyzed results are shown in A of FIG. 3.

Referring to A of FIG. 3, it can be seen that, as compared to the control group, the cells with the markers, which were knockdown by transfection of siRNAs listed in Table 12, exhibited that the expression levels of N-cadherin, Fibronectin, Snail and Slug, which are epithelial-mesenchymal transition (EMT) regulatory proteins, as well as the expression levels of the markers are inhibited. These results demonstrate that the siRNA or dsRNA of the present invention may selectively inhibit the expression of the corresponding markers, thereby inhibiting metastatic potential of liver cancer cells.

Example 5—Identification of Tumor Growth Inhibition by siRNA or dsRNA of the Present Invention siRNAs, each of which includes a sense RNA having the sequence shown in Table 12 above and an antisense RNA having the complementary sequence thereto, were subjected to in vitro transfection to the SNU-449 cell line in Example 1 by the method described in Example 1-2. Thereafter, athymic nude mice were subjected to subcutaneous injection of the transfected cells, followed by analyzing sizes of hepatic tumors and survival rates of the mice, and the analyzed results are shown in B of FIG. 3.

Referring to the left image of B of FIG. 3, it can be seen that most of the experimental groups have a significantly smaller hepatic tumor size than the control group. Therefore, it is understood that knockdown of the markers by the siRNA or dsRNA of the present invention may reduce overall tumor growth rate and decrease the average tumor volume.

Referring to the right image of B of FIG. 3, it can be seen that the tumor-free survival rates of the experimental groups are significantly higher than that of the control group.

Specifically, when 50 days elapses after the subcutaneous injection of the transfected cells, the control group exhibited tumors in 6 mice of 10 mice whereas the experimental group exhibited tumors in 1 to 2 mice only among 10 mice, thereby indicating that the siRNA or dsRNA of the present invention may effectively inhibit the growth of hepatic tumors.

Example 6—Identification of Liver Cancer Prevention Efficacy of siRNA or dsRNA of the Present Invention siRNAs, each of which includes a sense RNA having a sequence shown in Table 13 below and an antisense RNA having a complementary sequence thereto, were subjected to in vivo transfection by the method described in Example 1-8, and processes thereof, ultrasonic images and the number of tumors over time are shown in A of FIG. 4. Further, expression inhibitory levels for the indicator genes by the siRNAs loaded on the porous nanoparticles were analyzed by the method in Example 1-9 and shown in B of FIG. 4.

Referring to A of FIG. 4, in the case of the control group injected with only porous nanoparticles, multiple large hepatic tumors were found in 3 to 4 mice 17 weeks after the injection whereas the experimental group injected with porous nanoparticles loaded with siRNA exhibited that only a relatively small hepatic tumor was found in 2 to 4 mice 19 weeks after the injection. Further, as shown in B of FIG. 4, it can be seen that, as compared to the control group, the experimental group could significantly reduce the expression levels of the indicator gens in vivo as a result of Western blotting. These results demonstrate that the siRNA or dsRNA of the present invention may effectively inhibit the expression of the markers in vivo, and exert excellent effects in inhibition of hepatic tumor formation and prevention of liver cancer.

TABLE 13

| SEQ ID NO | Sense RNA sequence | Name in FIG. 1 | Target gene |
|---|---|---|---|
| SEQ ID NO: 311 | 5'-CCUCAGCGUUUCAAUCUUUUU-3' | Banf1 | Mouse BANF1 gene |
| SEQ ID NO: 312 | 5'-CGACUGCAGAAUCUCCUCUUU-3' | Plod3 | Mouse PLOD3 gene |
| SEQ ID NO: 313 | 5'-CUGCUUUACGAUACUUUCAUU-3' | 5f3b4 | Mouse 5F3B4 gene |

Example 7—Identification of Formation of Porous Silica Particles and Pore Expansion The small pore particles and the prepared porous silica particles in Example 1-11(1) to (3) were observed with a microscope to identify whether the small pore particles were uniformly formed and the pores were sufficiently expanded thus to uniformly form the porous silica particle (FIGS. 5 to 8).

FIG. 5 is photographs illustrating the porous silica particles in Example 1-11(1) and FIG. 6 is photographs illustrating the porous silica particles in Example 1-11(2), demonstrating that the porous silica particles in a spherical shape with sufficiently expanded pores were uniformly formed. Further, FIG. 7 is photographs illustrating the small pore particles in Example 1-11(1), and FIG. 8 is comparative photographs illustrating the small pore particles in Examples 1-11(1) and 1-11(3), demonstrating that spherical small pore particles were uniformly formed.

Example 8—Identification of Biodegradability of Porous Silica Particles

In order to identify the biodegradability of the porous silica particles in Example 1-11(1), the degree of biodegradation at 37° C. under SBF (pH 7.4) was observed with a microscope at 0 hours, 120 hours and 360 hours, and the observed results are shown in FIG. 9.

Referring to FIG. 9, it can be seen that the porous silica particles were almost completely degraded after 360 hours elapse from the observation.

Example 9—Measurement of Absorbance Ratio of Porous Silica Particles

1. Measurement Method

The absorbance ratio according to the following Equation 1 was measured:

$$A_t/A_0 \quad \text{[Equation 1]}$$

(wherein $A_0$ is absorbance of the porous silica particles measured by placing 5 ml of a suspension including 1 mg/ml of the porous silica particles into a cylindrical dialysis membrane having pores with a diameter of 50 kDa, 15 ml of the same solvent as the suspension is placed outside the dialysis membrane while being in contact with the dialysis membrane, followed by horizontal agitation at 60 rpm and 37° C. inside and outside the dialysis membrane, and $A_t$ is absorbance of the porous silica particles measured after t hours elapses from the measurement of $A_0$).

Specifically, 5 mg of the porous silica particle powders were dissolved in 5 ml of SBF (pH 7.4). Thereafter, 5 ml of the porous silica particle solution was placed in a dialysis membrane having a pore diameter of 50 kDa shown in FIG. 10. 15 ml of SBF was added to an outer membrane, and SBF of the outer membrane was replaced every 12 hours. Degradation of the porous silica particles was performed while horizontally agitating at 37° C. and 60 rpm.

Thereafter, the absorbance was measured by UV-vis spectroscopy and analyzed at λ=640 nm.

2. Absorbance Ratio Measurement Results

The absorbance ratio of the porous silica particles in Example 1-11(1) was measured according to the above method, and the results are shown in FIG. 11.

Referring to FIG. 11, it can be seen that t when the absorbance ratio becomes 1/2 was about 58 hours, demonstrating very slow degradation.

3. Measurement Results by Particle Size

The absorbance of the porous silica particles in each of Examples 1-11(1), (5) and (6) was measured according to Equation 1 above and the results are shown in FIG. 12 (using SBF as a suspension and a solvent).

Referring to FIG. 12, it can be seen that t is decreased as the particle diameter is increased.

4. Measurement Results to Pore Diameter Average Diameter

The absorbance of the porous silica particles in each of Examples 1-11(1) and (9), and the small pore silica particles in Example 1-11(1) as a control group was measured according to the above Equation 1 (using SBF as suspension and solvent).

Referring to FIG. 13, it can be seen that the porous silica particles in the examples have significantly larger t than the control.

5. Measurement Results by pH

The absorbance of the porous silica particles in Example 1-11(4) was measured by pH. The absorbance was measured in SBF and in Tris at pH 2, 5 and 7.4, respectively, and the results are shown in FIG. 14.

Referring to FIG. 14, there was a difference in t by pH, but t when all absorbance ratios became 1/2 was 24 or more.

6. Charging

The absorbance of the porous silica particles in Example 1-12(1)-1) was measured, and the results are shown in FIG. 15 (using Tris (pH 7.4) as a suspension and a solvent).

Referring to FIG. 15, even the positively charged particles showed that t when the absorbance ratio of the absorbance became 1/2 was 24 or more.

Example 10—Release of siRNA or dsRNA Loaded on Porous Silica Particles

10 μl of the porous silica particles loaded with the siRNA in Example 1-13 was resuspended in SBF (pH 7.4, 37° C.) and placed in a dialysis membrane having a pore diameter of 20 kDa (the tube in FIG. 16). Then, the dialysis tube was immersed in 1.5 ml of SBF. The release of siRNA was performed while horizontally agitating at 37° C. and 60 rpm.

The release solvent was recovered at 0.5, 1, 2, 4, 8, 12, 24 hours prior to 24 hours and then, every 24 hours, 0.5 ml of the release solvent was recovered for fluorescence measurement and SBF was added thereto.

The fluorescence intensity of the siRNA was measured at a wavelength of 670 nm ($\lambda_{ex}$=647 nm) to determine the degree of siRNA release, and the results are shown in FIG. 17.

Referring to FIG. 17, it can be seen that the time at which 50% of the siRNA was released was about 40 hours or more.

Example 11—Identification of Target Delivery of siRNA or dsRNA Loaded on Porous Silica Particles In order to verify whether the siRNAs of the present invention can play a role of a transporter in a desired level for study of siRNA delivery in animal level, tumor inhibitory rates due to the release of bioactive material in mice (rats) were confirmed.

Specifically, Balb/c nude male mice (5 weeks old) were purchased from Orient Bio Inc., and 3 million HeLa cells (cervical cancer cells) were dispersed in sterilized 1×PBS to proliferate Xenograft tumors subcutaneously injected into the mice. When 70 mm³ size of solidified tumors were observed, PBS, FITC-porous silica particles (porous silica particles in Example 1-12(1)-2)-(ii)), and FITC-porous silica particles loaded with siRNA (porous silica particles in Example 1-12(1)-2)-(ii)) were injected into tumors in the mice, respectively. Then, fluorescence intensities and distribution thereof were measured immediately before, immediately after, and 48 hours after the administration, by means of FOBI fluorescence in vivo imaging system (Neo science, Korea).

FITC labeling were implemented by: dispersing 50 mg of silica particles in 1 ml of dimethyl sulfoxide (DMSO); adding 25 μg (10 μl) of FITC-NHS (N-hydroxysuccinimide) solution (2.5 mg/mL) thereto; reacting the mixture at room temperature for 18 hours while shielding light with aluminum foil; purifying the reaction product through centrifugation (8500 rpm, 10 minutes); discarding the supernatant while collecting settled particles; and evenly dispersing the particles in ethanol, wherein the above processes were repeated three and four times with ethanol and distilled water to purify until FITC color is invisible in the supernatant.

Referring to FIG. 18 demonstrating results of the above experiments, the control group refers to administration of PBS alone, Cy5-siRNA refers to administration of siRNA in Example 1-13 alone, FITC-DDV refers to administration of FITC-labeled porous silica particles alone, and the complex refers to administration of FITC-labeled porous silica particles loaded with the siRNA in Example 1-13. Referring to this figure, it can be seen that the siRNA loaded on the particles and delivered into the body has a longer duration of activity and stays longer at the injected site, thereby exhibiting strong fluorescence even after 48 hours.

A sequence listing electronically submitted with the present application on Nov. 29, 2021 as an ASCII text file named 20211129_Q25720LC02-V_TU_SEQ, created on Nov. 29, 2021 and having a size of 125,000 bytes, is incorporated herein by reference in its entirety.

What is claimed is:

1. A pharmaceutical composition for preventing or treating liver cancer, comprising:
    a porous silica particle; and
    at least one of siRNA and dsRNA loaded on the porous silica particle,
    wherein the siRNA includes a sense RNA having at least one sequence selected from the group consisting of sequences of SEQ ID NOs: 121 to 157 and 635, and an antisense RNA having a complementary sequence thereto; and
    the dsRNA has at least one sequence selected from the group consisting of sequences of SEQ ID NOs: 274 to 310,
    wherein the porous silica particle is characterized in that t when a ratio of absorbance in the following Equation 1 becomes 1/2 is 20 or more:

$$A_t/A_0 \quad \text{[Equation 1]}$$

wherein $A_0$ is absorbance of the porous silica particle measured by placing 5 ml of a suspension including 1 mg/ml of the porous silica particle into a cylindrical dialysis membrane having pores with a diameter of 50 kDa; 15 ml of the same solvent as the suspension is placed outside the dialysis membrane while being in contact with the dialysis membrane, followed by horizontal agitation at 60 rpm and 37° C. inside and outside the dialysis membrane; and
    $A_t$ is absorbance of the porous silica particle measured after t hours elapses from the measurement of $A_0$.

2. The composition according to claim 1, wherein
    the siRNA includes a sense RNA having at least one sequence selected from the group consisting of sequences of SEQ ID NOs: 121 to 128, 130 to 154, 156 to 157, 635, and an antisense RNA having a complementary sequence thereto; and/or
    the dsRNA has at least one sequence selected from the group consisting of sequences of SEQ ID NOs: 274 to 281, 283 to 307, 309 and 310.

3. The composition according to claim 1, wherein the t is 40 or more.

4. The composition according to claim 1, wherein the siRNA includes a sense RNA having at least one sequence selected from the group consisting of sequences of SEQ ID NO: 136, and an antisense RNA having a complementary sequence thereto; and
    the dsRNA has at least one sequence selected from the group consisting of sequences of SEQ ID NO: 289.

5. The composition according to claim 1, wherein the porous silica particle has a hydrophilic substituent or a hydrophobic substituent.

6. The composition according to claim 1, wherein the porous silica particle has at least one hydrophilic substituent selected from the group consisting of aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, ether, indene, sulfonyl, methylphosphonate, polyethylene glycol, substituted or unsubstituted $C_1$ to $C_{30}$ alkyl, substituted or unsubstituted $C_3$ to $C_{30}$ cycloalkyl, substituted or unsubstituted $C_6$ to $C_{30}$ aryl, and $C_1$ to $C_{30}$ ester groups.

7. The composition of claim 1, wherein the porous silica particle is positively or negatively charged on an outer surface of the particle or an inside of a pore thereof at neutral pH.

8. The composition of claim 1, wherein the porous silica particle is positively charged on an outer surface of the particle or an inside of a pore thereof at neutral pH.

9. The composition of claim 1, wherein the porous silica particle has an average particle diameter of 100 to 400 nm and a pore diameter of 4 to 30 nm.

* * * * *